United States Patent
Jankun et al.

(10) Patent No.: US 8,211,858 B2
(45) Date of Patent: *Jul. 3, 2012

(54) MODIFIED PLASMINOGEN ACTIVATOR INHIBITOR TYPE-1 MOLECULE AND METHODS BASED THEREON

(75) Inventors: Jerzy Jankun, Sylvania, OH (US); Ewa Skrzypczak-Jankun, Sylvania, OH (US); Steven H. Selman, Toledo, OH (US)

(73) Assignee: The University of Toledo, Toledo, OH (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/597,686

(22) PCT Filed: Apr. 24, 2008

(86) PCT No.: PCT/US2008/005272
§ 371 (c)(1),
(2), (4) Date: Mar. 18, 2010

(87) PCT Pub. No.: WO2009/014564
PCT Pub. Date: Jan. 29, 2009

(65) Prior Publication Data
US 2010/0184667 A1    Jul. 22, 2010

Related U.S. Application Data

(60) Provisional application No. 60/926,797, filed on Apr. 27, 2007.

(51) Int. Cl.
*A61K 38/00* (2006.01)
*C07K 1/00* (2006.01)

(52) U.S. Cl. .................................. 514/12.1; 530/350
(58) Field of Classification Search .................. 514/12; 530/350
See application file for complete search history.

(56) References Cited

U.S. PATENT DOCUMENTS

| | | | |
|---|---|---|---|
| 4,554,101 A | 11/1985 | Hopp | |
| 4,946,778 A | 8/1990 | Kushan | |
| 4,980,286 A | 12/1990 | Morgan | |
| 5,635,493 A | 6/1997 | Vournakis | |
| 5,639,726 A | 6/1997 | Lawrence et al. | |
| 5,679,350 A | 10/1997 | Jankun | |
| 6,303,338 B1 | 10/2001 | Ni et al. | |
| 7,592,422 B2 | 9/2009 | Swiercz et al. | |
| 2005/0158295 A1 | 7/2005 | Swiercz et al. | |
| 2006/0153798 A1 | 7/2006 | Mrsny | |
| 2010/0184667 A1 | 7/2010 | Jankun et al. | |

FOREIGN PATENT DOCUMENTS

| | | |
|---|---|---|
| WO | 9013678 | 11/1990 |
| WO | 9206180 | 4/1992 |
| WO | 9222635 | 12/1992 |
| WO | 9314188 | 7/1993 |
| WO | 9733899 | 9/1997 |
| WO | 9734911 | 9/1997 |
| WO | 9739028 | 10/1997 |
| WO | 9923105 | 5/1999 |
| WO | 03080646 | 2/2003 |
| WO | 2009014564 | 1/2009 |
| WO | 2009045412 | 4/2009 |

OTHER PUBLICATIONS

Schirrmacher, V., "Cancer Metastasis: Experimental Approaches, Theoretical Concepts, and Impacts for Treatment Strategies," Adv. Cancer Res., 1985, pp. 1-73, vol. 43, Abstract.
Seetharam, et al., "Purification and Characterization of Active and Latent Forms of Recombinatnt Plasminogen Activator Inhibitor 1 Produced in *Escerichia coli*," Biochemistry, Oct. 1992, pp. 9877-9882, vol. 31, No. 41.
Seffernick, J.L. et al., "Melamine Deaminase and Atrazine Chlorohydrolase: 98 Percent Identical but Functionally Different," Journal of Bacteriology, Apr. 2001, pp. 2405-2410, vol. 183, No. 8.
Seidman, A.D., "Gemcitabine as Single-Agent Therapy in the Management of Advanced Breast Cancer," Oncology, 2001, pp. 11-14, vol. 15, Abstract.
Seiffert, D. et al., "Kinetic Analysis of the Interaction Between Type 1 Plasminogen Activator Inhibitor and Vitronectin adn Evidence that the Bovine Inhibitor Binds to a Thrombin-Derived Amino-Terminal Fragment of Bovine Vitronectin," Biochim, Biophys. Acta., May 1991, pp. 23-30, vol. 1078, Abstract.
Simonovic, I. et al., "The Native Metastable Fold of C1-Inhibitor is Stabilized by Disulfide Bonds," Biochimica et Biophysica Acta, 2000, pp. 97-102, vol. 1481.
Sisson, T.H. et al., "The Plasminogen Activation System in Lung Disease," Current Drug Targets, 2007, pp. 1016-1029, vol. 8.
Sluipianek, A. et al., "Role of Phosphatidylinositol 3-Kinase-Akt Pathway in Nucleophosmin/Anaplastic Lymphoma Kinase-Mediated Lymphomagenesis," Cancer Research, 2001, pp. 2194-2199, vol. 61. Swiercz, R. et al., "Angiostatic Activity of Synthetic Inhibitors of Urokinase Type Plasminogen Activator," Oncology Reports, 1999, pp. 523-526, vol. 6.
Swiercz, R. et al., "Recombinant PAI-1 Inhibits Angiogenesis and Reduces Size of LNCaP Prostate Cancer Xenografts in SCID Mice," Oncology Reports, 2001, pp. 463-470, vol. 8.

(Continued)

*Primary Examiner* — Maryam Monshipouri
(74) *Attorney, Agent, or Firm* — MacMillan, Sobanski & Todd, LLC

(57) ABSTRACT

The present invention relates to a modified plasminogen activator inhibitor type-1 (PAI-1) molecule that displays an increased in vivo half-life of the active form of PAI-1, but is deficient in one or more functional activities as compared to the wild-type PAI-1 protein. The modified PAI-1 molecule that displays an increased half-life further displays at least one of the following functional characteristics: (i) decreased binding activity to at least one of the following molecules: urokinase plasminogen activator (uPA), tissue plasminogen activator (tPA) and vitronectin (Vn); and (ii) decreased specific activity against at least one of the following molecules: uPA, tPA and Vn. The invention further relates to pharmaceutical compositions comprising modified PAI-1 molecules and methods of using these pharmaceutical compositions for treatment.

12 Claims, 11 Drawing Sheets

OTHER PUBLICATIONS

Figure 2A:
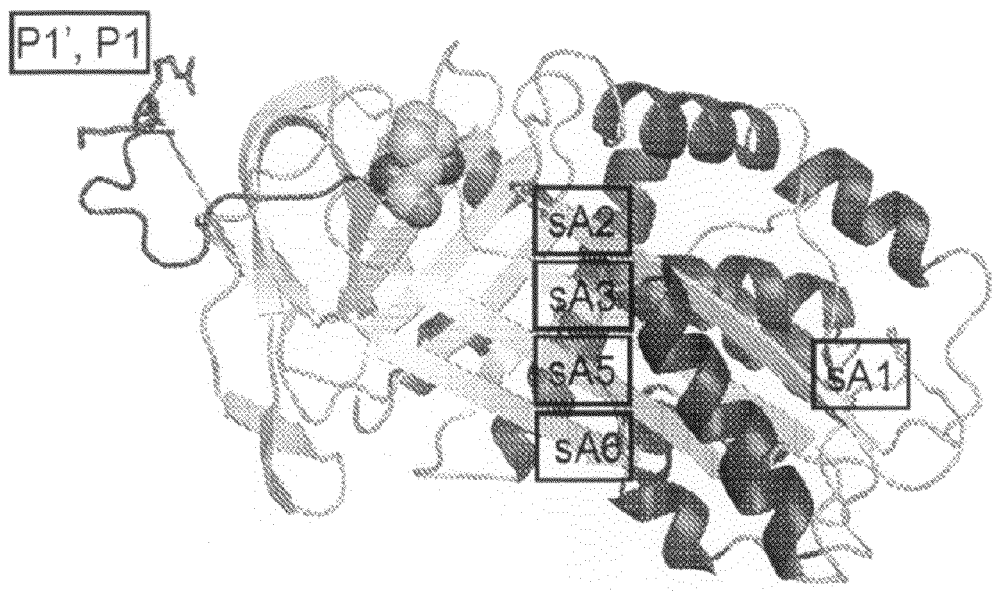

Takeda, S.-I. et al., "Construction fo Chimaeric Processed Immunoglobulin Genes Containing Mouse Variable and Human Constant Region Sequences," Nature, 1985, pp. 452-454, vol. 314, Issue 6010, Abstract.

Tolsma, S.S. et al., "Peptides Derived form Two Separate Domains of the Matrix Protein Thrombospondin-1 have Anti-Angiogenic Activity," J. Cell Biol., 1993, pp. 497-511, vol. 122.

Tolstoshev, P., "Gene Therapy, Concepts, Current Trials and Future Directions," Ann. Rev. Pharmacol. Toxicol., 1993, pp. 573-596, vol. 33, Abstract.

Tucker, H.M. et al., "Engineering of Plasminogen Activator Inhibitor-1 to Reduce the Rate of Latency Transition," Nature, Jun. 1995, pp. 442-445, vol. 2, No. 6.

Tuynder, M. et al., "Biological Models and Genes of Tumor Reversion: Cellular Reprogramming through tpt1/TCTP and SIAH-1," Proc. Natl. Acad. Sci., Nov. 2002, pp. 14976-14981, vol. 99, No. 23.

Tuynder, M. et al. "Translationally Controlled Tumor Protein is a Target of Tumor Reversion," Proc. Natl. Acad. Sci., Oct. 2004, pp. 15364-15369, vol. 101, No. 43.

Van Mourik, et al., "Purification of an Inhibitor of Plasminogen Activator (Antiactivator) Synthesized by Endothelial Cells," J. Biol. Chem., Dec. 1984, pp. 14914-14921, vol. 259, No. 23.

Van Hinsbergh, V. et al., "Pericellular Proteases in Angiogenesis and Vasculogenesis," Arteriosclerosis Thrombosis and Vascular Biology, 2006, pp. 716-728, vol. 26.

Vaughan, et al., "Studies of Recombinant Plasminogen Activator Inhibitor-1 in Rabbits. Pharmacokinetics and Evidence for Reactivation of Latent Plasminogen Activator Inhibitor-1 In Vivo," Circulation Research, Nov. 1990, pp. 1281-1286, vol. 67, No. 5.

Vihinen, P. et al., "Matrix Metalloproteinases as Therapeutic Targets in Cancer," Current Drug Targets, May 2005, pp. 203-220, vol. 5, No. 3, Abstract.

Wagner, M.J. et al., "Nucleotide Sequence of the Thymidine Kinase Gene of Herpes Simplex Virus Type 1," Proc. Natl. Acad. Sci., Mar. 1981, pp. 1441-1445, vol. 78, No. 3.

Walsh, C.E. et al., "Gene Therapy for Human Hemoglobinopathies," Proc. Soc. Exp. Biol. Med., Dec. 1993, pp. 289-300, vol. 204.

Wells, J.A. et al., "Additivity of Mutational Effects in Proteins," Biochemistry, Sep. 1990, pp. 8509-8517, vol. 29.

Wilson, et al., "Plasminogen Activator and Metalloprotease Activities of Du-145, PC-3, and I-LN-PC-3-1A Human Prostate Tumors Grown in Nude Mice: Correlation with Tumor Invasive Behaviour," Cell Mol. Biol. Res., 1993, pp. 751-760, vol. 39, No. 8.

Wiman, B. et al., "Invasion of Tissue Plasminogen Activator in P asma. Demonstration of a Complex with a New Rapid Inhibitor," J. Biol. Chem., Mar. 1984, pp. 3644-3647, vol. 259, No. 6.

Wiman, B. et al., "Plasminogen Activator Release During Venous Stasis and Exercise as Determined by a New Specific Assay," Clin. Chim. Acta., Jan. 1983, pp. 279-288, vol. 127, No. 2.

Wiman, B. et al., "The Role of the Fibrinolytic System in Deep Vein Thrombosis," J. Lab. Clin. Med., Feb. 1985, pp. 265-270, vol. 105, No. 2.

Wu, G.Y. et al., "Delivery Systems for Gene Therapy," Biotherapy, 1991, pp. 87-95, vol. 3, No. 1, Abstract.

Wu, J.-J. et al., "Sites of Stromelysin Cleavage in Collagen Types II, IX, X, and XI of Cartilage," J. Biol. Chem., Mar. 1991, pp. 5625-5628, vol. 266.

Wun, T.-C. et al., "Affinity Purification of Active Plasminogen Activator Inhibitor-1 (PAI-1) Using Immobolized Anhydrourokinase. Demonstration of the Binding, Stabilization, and Activation of PAI-1 by Vitronectin," J. Biol. Chem., May 1989, pp. 7862-7868, vol. 264, No. 14.

Xue, Y. et al., "Interfering with the Inhibitory Mechanism of Serpins: Crystal Structure of a Complex Formed Between Cleaved Plasminogen Activator Inhibitor Type 1 and a Reacive-Centre Loop Peptide," Structure, May 1998, pp. 627-636, vol. 6, No. 5.

Yamamoto, T. et al., "Identification of a Functional Promoter in the Long Terminal Repeat of Rous Sarcoma Virus," Cell, Dec. 1980, pp. 787-797, vol. 22, Abstract.

Yamanaka, N. et al., "Engraftment of Tonsillar Mononuclear Cells in Human Skin/SCID Mouse Chimera. Validation of a Novel Xenogeneic Transplantation Model for Autoimmune Diseases," Microbiol. Immunol., 2001, pp. 507-514, vol. 45, No. 7, Abstract.

Zhang, G. et al., "Mitogenic Signaling of Urokinase Receptor-Deficient Kidney Fibroblasts: Actions of an Alternative Urokinase Receptor and LDL Receptor-Related Protein," J. Am. Soc. Nephrol., 2004, pp. 2090-2102, vol. 15.

Zijlstra, M. et al., "Germ-Line Transmission of a Disrupted β2Microglobulin Gene Produced by Homologous Recombination in Embryonic Stem Cells," Nature, Nov. 1989, pp. 435-438, vol. 342, Abstract.

Zimmerman, L. et al., "A Triglycine Linker Improves Tumor Uptake and Biodistributions of 67-Cu-Labeled Anti-Neuroblastoma MAb chCE7 F(ab')2 Fragments," Nucl. Med. Biol., Nov. 1999, pp. 943-950, vol. 26, No. 8, Abstract.

European Search Report, Application No. 08826564.0 dated Oct. 15, 2010.

European Supplementary Search Report, Application No. 03745086.3 dated Apr. 13, 2006.

International Preliminary Report on Patentability, PCT/US2008/005272 filed Apr. 24, 2008, dated Feb. 2, 2010.

International Search Report and the Written Opinion, PCT/US08/05272 filed Apr. 24, 2008, dated May 1, 2009.

U.S. Appl. No. 60/361,670, filed Mar. 4, 2002.

Canadian Intellectual Property Office, Requisition by the Examiner, Application No. 2,481,556, dated Nov. 2, 2010, Corresponding to US Patent No. 7,592,422.

Jankun, J. et al., "Inhibitors of Urokinase Reduce Size of Prostate Cancer Xenografts in Severe Combined Immunodeficient Mice," Cancer Research, Feb. 1997, pp. 559-563, vol. 57.

Kohler G., et al., "Continuous Cultures of Fused Cell Secreting Antibody of Predefined Specificity," Nature, Aug. 1975, pp. 495-497, vol. 256, Abstract.

Koller, B.H. et al., "Inactivating the β2-Microglobulin Locus in Mouse Embryonic Stem Cells by Homologous Recombination," Proc. Natl. Acad. Sci., Nov. 1989, pp. 8932-8935, vol. 86.

Kozbor, D. et al., "The Production of Monoclonal Antibodies from Human Lymphocytes," Immunology Today, Mar. 1983, p. 72-79, vol. 4, Issue 3, Abstract.

Kwaan, H.C. et al., "Components of the Plasminogen-Plasmin System in Human Tumor Cell Lines," Semin. Thromb. Hemost., Jul. 1991, pp. 175-182, vol. 17, No. 3.

Kyte, J. et al., "A Simple Methods for Displaying the Hydropathic Character of a Protein," J. Mol. Biol., 1982, pp. 105-132, vol. 157.

Lah, T.T. et al., "Antiprotease Therapy in Cancer: Hot or Not?" Expert Opinion Biol. Ther., Mar. 2006, pp. 257-279, vol. 6, No. 3, Abstract.

Langer, R., "New Methods of Drug Delivery," Science, Sep. 1990, pp. 1527-1533, vol. 249, No. 4976, Abstract.

Lara, P.N, et al., "A Radomized Phase II Trial of the Matrix Metalloproteinase Inhibitor BMS-275291 in Hormone-Refractory Prostate Cancer Patients with Bone Metastases," Clinical Cancer Research, Mar. 2006, pp. 1556-1563, vol. 12.

Lambers, J.W. et al., "Activation of Human Endothelial Cell-Type Plasminogen Activator Inhibitor (PAI-1) by Negatively Charged Phospholipids," The Journal of Biological Chemistry, Dec. 1987, pp. 17492-17496, vol. 262.

Lawrence, D.A. et al., "Engineering Plasminogen Activator Inhibitor 1 Mutants with Increased Functional Stability," Biochemistry, 1994, pp. 3643-3648, vol. 33.

Lawrence, D.A. et al., "Purification of Active Human Plasminogen Activator Inhibitor 1 from *Escherichia coli*. Comparison with Natural and Recombinant Forms Purified from Eucaryotic Cells," Eur. J. Biochem., 1989, pp. 523-533, vol. 186, No. 3.

Levin, E.G. et al., "Conversion of the Active to Latent Plasminogen Activator Inhibitor From Human Endothelial Cells," Blood, 1987, pp. 1090-1098, vol. 70, No. 4.

Levy, R.J. et al., "Inhibition of Calcification of Bioprosthetic Heart Valves by Loyal Controlled-Release Diphosphonate," Science, Apr. 1985, p. 190-192, vol. 228, No. 4696, Abstract.

Ludwig, T., "Local Proteolytic Activity in Tumor Cell Invasion and Metastasis," Bioessays, 2005, pp. 1181-1191, vol. 27, Abstract.

Maione, T.E. et al., "Inhibition of Tumor Growth in Mice by an Analogue of Platelet Factor 4 That Lacks Affinity for Heparin and Retains Potent Angiostatic Activity," Cancer Research, Apr. 1991, p. 2077-2083, vol. 51.

Mayer, M. "Biochemical and Biological Aspects of the Plasminogen Activation System," Clin. Biochem., Jun. 1990, pp. 197-211, vol. 23, No. 3.

Mayer, M. "The Pharmacokinetics of Plasminogen Activator Inhibitor-1 in the Rabbit," Blood, Oct. 1990, pp. 1514-1520, vol. 76.

Mimuro, J. et al., "Binding of Type 1 Plasminogen Activator Inhibitor to Extracellular Matrix of Cultured Bovine Endothelial Cells," The Journal of Biological Chemistry, Mar. 1989, pp. 5058-5063, vol. 264, No. 9.

Mimuro, J. et al., "Extracellular Matrix of Cultured Bovine Aortic Endothelial Cells Contains Functionally Active Type 1 Plasminogen Activator Inhibitor," Blood, Sep. 1987, pp. 721-728, vol. 70, No. 3.

Min, H.Y. et al., "Urokinase Receptor Antagonists Inhibit Angiogenesis and Primary Tumor Growth in Syngeneic Mice," Cancer Research, May 1996, pp. 2428-2433, vol. 56.

Molina, J.R. et al., "A Phase and Pharmacokinetic Study of the Selective, Non-Peptidic Inhibitor of Matrix Metalloproteinase BAY 12-9566 in Combination with Etoposide and Carboplatin," Anticancer Drugs, Oct. 2005, pp. 997-1002, vol. 16, Abstract.

Morgan, R.A. et al., "Human Gene Therapy," Ann. Rev. Biochem., Jul. 1993, pp. 191-217, vol. 62, Abstract.

Morrison, S.L. et al., "Chimeric Human Antibody Molecules: Mouse Antigen-Binding Domains with Human Constant Region Domains," Proc. Natl. Acad. Sci., Nov. 1984, pp. 6851-6855, vol. 81.

Moscatelli, et al., "Membrane and Matrix Localization of Proteinases: A Common Theme in Tumor Cell Invasion and Angiogenesis," Biochim. Biophys. Acta., Aug. 1988, pp. 67-85, vol. 948, No. 1, Elsevier Science Publ. BV.

Mottonen, J. et al. "Structural Basis of Latency in Plasminogen Activator Inhibitor-1." Nature, Jan. 1992, pp. 270-273, vol. 355.

Mulligan, R.C., "The Basic Science of Gene Therapy," Science, 1993, pp. 926-932, vol. 260, No. 5110, Abstract.

Neuberger, M.S. et al., "Recombinant Antibodies Possessing Novel Effector Functions," Nature, 1984, pp. 604-608, vol. 312, Abstract.

Ny, T. et al., "Cloning and Sequence of a cDNA Coding for the Human β-Migrating Endothelial-Cell-Type Plasminogen Activator Inhibitor," Proc. Natl. Acad. Sci., Sep. 1986, pp. 6776-6780, vol. 83.

Ossowski, "In Vivo Invasion of Modified Chorioallantoic Membrane by Tumor Cells: The Role of Cell Surface-Bound Urokinase," J. Cell Biol., Dec. 1988, pp. 2437-2445, vol. 107.

Pawlak, R. et al., "The Role of the Thiol Group in the Antithrombotic Action of Captopril," Thromb. Haemost., 2000, pp. 919-920, vol. 84.

Pepper, et al., "Urokinase-Type Plasminogen Activator is Induced in Migrating Capillary Endothelial Cells," J. Cell Biol., Dec. 1987, pp. 2535-2541, vol. 105.

Pepper, et al., "Upregulation of Urokinase Receptor Expression on Migrating Endothelial Cells," J. Cell Biol., Aug. 1993, pp. 673-684, vol. 122, No. 3.

Plow, et al., "Cellular Regulation of Fibrinolysis," Thromb, Haemost., Jul. 1991, pp. 32-36, vol. 66, No. 1.

Pöllänen, et al., "Directed Plasminogen Activation at the Surface of Normal and Malignant Cells," Adv. Cancer Res., 1991, pp. 273-328, vol. 57.

Puli, S. et al., "Inhibition of Matrix Degrading Enzymes and Invasion in Human Glioblastoma (U87MG) Cells by Isoflavones," J. Neurooncol., 2006, pp. 135-142, vol. 79, Abstract.

Rånby, et al., "A Sensitive Assay for Tissue Plasminogen Activator," Thromb. Res., Sep. 1982, pp. 743-749, vol. 27, No. 6.

Renckens, R. et al., "Plasminogen Activator Inhibitor Type 1 is Protective During Severe Gram-Negative Pneumonia," Blood, Feb. 2007, pp. 1593-1601, vol. 109, No. 4.

Rosenfeld, M.A. et al., "Adenovirus-Mediated Transfer of a Recombinant Alpha 1-Antitrypsin Gene to the Lung Epithelium In Vivo," Science, Apr. 1991, pp. 431-434, vol. 252, Abstract.

Rosenfeld, M.A. et al., "In Vivo Transfer of the Human Cystic Fibrosis Transmembrane Conductance Regulator Gene to the Airway Epithelium," Cell, Jan. 1992, pp. 143-155, vol. 68, Issue 1, Abstract.

Saksela, et al., "Cell-Associated Plasminogen Activation: Regulation and Physiological Functions," Annu. Rev. Cell Biol., 1988, pp. 93-126, vol. 4.

Saksela, et al., "Plasminogen Activation and Regulation of Pericellular Proteolysis," Biochim. Biophys. Acta., Nov. 1985, pp. 35-65, vol. 823, No. 1.

Salonen, E.-M. et al., "Interaction of Plasminogen Activator Inhibitor (PAI-1) with Vitronectin," The Journal of Biological Chemistry, Apr. 1989, pp. 6339-6343, vol. 264, No. 11.

Sambrook, et al., Molecular Cloning, A Laboratory Manual, 1990, 2d Ed., Cold Spring Harbor Laboratory, Cold Spring Harbor, New York, Abstract.

Sarkar, G. et al., "The 'Megaprimer' Method of Site-Directed Mutagenesis," Biotechniques, Apr. 1990, pp. 404-407, vol. 8, Abstract.

Saudek, C.D. et al., "A Preliminary Trial of the Programmable Implantable Medication System for Insulin Delivery," N. Engl. J. Med., Aug. 1989, p. 574-579, vol. 321, Abstract.

Amagata, T. et al., "Exploring Sponge-Derived Terpenoids for Their Potency and Selectivity against 12-Human, 15-Human, and 15-Soybean Lipoxygenases," J. Nat. Prod., 2003, pp. 230-235, vol. 66.

Arlen, P.M. et al., "A Randomized Phase II Study of Cancurrent Docetaxel Plus Vaccine Versus Vaccine Alone in Metastatic Androgen-Independant Prostate Cancer," Clinical Cancer Research, Feb. 15, 2006, pp. 1260-1269, vol. 12, No. 4.

Balsara, R.D. et al., "A Novel Function of Plasminogen Activator Inhibitor-1 in Modulation of the AKT Pathway in Wild-Type and Plasminogen Activator Inhibitor-1 Deficient Endothelial Cells," J. Biol Chem., Aug. 11, 2006, pp. 22527-22536, vol. 281.

Basrur, V. et al., "Proteomic Analysis of Early Melanosomes: Identification of Novel Melanosomal Proteins," J. Proteome Res., 2003, pp. 69-79, vol. 2, Abstract.

Berkenpas, M.B. et al., "Molecular Evolution of Plasminogen Activator Inhibitor-1 Functional Stability," EMBO. J., 1995, pp. 2969-2977, vol. 14.

Bernoist, C. et al., "In Vivo Sequence Requirements of the SV40 Early Promotor Region," Nature, 1981, pp. 304-310, vol. 290, Abstract.

Boncela, J. et al., "Acute Phase Protein α1-Acid Glycoprotein Interacts with Plasminogen Activator Inhibitor Type 1 and Stabilizes Its Inhibitory Activity," The Journal of Biological Chemistry, Sep. 2001, pp. 35305-35311, vol. 276, No. 38.

Bout, A. et al., Lung Gene Therapy: In Vivo Adenovirus-Mediated Gene Transfer to Rhesus Monkey Airway Epithelium, Human Gene Therapy, Jan. 1994, pp. 3-10, vol. 5, Issue 1, Abstract.

Brinster, R.L. et al., "Regulation of Metallothionein-Thymidine Kinase Fusion Plasmids Injected into Mouse Eggs," Nature, Mar. 1982, pp. 39-42, vol. 296.

Brooks, P.C. et al., "Requirement of Vascular Integrin Alpha V Beta 3 for Angiogenesis," Science, 1994, p. 569-571, vol. 264, Abstract.

Buchwald, H., et al., "Long-Term, Continuous Intravenous Heparin Administration by an Implantable Infusion Pump in Ambulatory Patients with Recurrent Venous Thrombosis," Surgery, 1980, p. 507-516, vol. 88, Abstract.

Cale, J.M. et al., "Structure-Function Relationship of Plasminogen Activator Inhibitor-1 and Its Potential as a Therapeutic Agent," Current Drug Targets, 2007, pp. 971-981, vol. 8.

Chorostowska-Wynimko, J. et al., "A Novel Form of the Plasminogen Activator Inhibitor Created by Cystein Mutations Extends Its Half-Life: Relevance to Cancer and Angiogenesis," Molecular Cancer Therapeutics, Jan. 2003, pp. 19-28, vol. 2.

Chorostowska-Wynimko, J. et al., "Cysteine Mutations of Plasminogen Activator Inhibitor Type 1 Extend Its Half-Life. Implication for Inhibition of Cancer Angiogenesis," Proceedings American Association for Cancer Research, Mar. 2002, p. 141, vol. 43, Abstract #705.

Chou, P.Y. et al., "Prediction of Protein Conformation," Biochemistry, 1974, p. 222-245, vol. 13, Abstract.

Chuang, T.-H., et al., "Cloning of the Mink Plasminogen Activator Inhibitor Type-1 Messenger RNA: An mRNA with a Short Half Life," Gene, 1995, pp. 303-308, vol. 162.

Cohen, G.E., "ALIGN: A Program to Superimpose Protein Coordinates, Accounting for Insertions and Deletions," Journal of Applied Crystallography, 1997, pp. 1160-1161, vol. 30, Abstract.

Conese, M. et al., "The Urokinase/Urokinase Receptor System and Cancer Invasion," Bailliers Clin Haematol., Jun. 1995, pp. 365-389, vol. 8, No. 2.

Cote, R.J. et al., "Generation of Human Monoclonal Antibodies Reactive with Cellular Antigens," Proc. Natl. Acad. Sci., Apr. 1983, pp. 2026-2030, vol. 80.

Crowley, C.W. et al., "Prevention of Metastasis by Inhibition of the Urokinase Receptor," Proc. Natl. Acad. Sci., Jun. 1993, pp. 5021-5025, vol. 90.

Danø, K. et al., "Plasminogen Activators, Tissue Degradation, and Cancer," Adv. Cancer Res., 1985, pp. 139-266, vol. 44.

Declerck, P.J. et al., "Measurement of Plasminogen Activator Inhibitor 1 in Biologic Fluids with a Murine Monoclonal Antibody-Based Enzyme-Linked Immunosorbent Assay," Blood, Jan. 1988, pp. 220-225, vol. 71, No. 1.

Declerck, P.J. et al., "Purification and Characterization of a Plasminogen Activator Inhibitor 1 Binding Protein from Human Plasma. Identification as a Multimeric form of S Protein (Vitronectin)," J. Biol. Chem., Oct. 1988, pp. 15454-15461, vol. 263, No. 3.

Denardo, G.L. et al., "Comparison of 1,4,7,10-Tetraazacyclododecane-N,N',N'',N'''-tetraacetic acid (DOTA)-Peptide-ChL6, A Novel Immunoconjugate with Catabolizable Linker, to 2-Iminothiolane-2[p-(Bromoacetamido)benzyl]-DPTA-ChL6 in Breast Cancer Xenografts," Clinical Cancer Research, Oct. 1998, pp. 2483-2490, vol. 4, No. 10.

De Taeye, B. et al., "The Story of the Serpin Plasminogen Activator Inhibitor I: Is There Any Need for Another Mutant?" Thromb Haemost, 2004, pp. 898-924, vol. 92.

Dracopoli, N.C. et al., Current Protocols in Human Genetics, 1994, vol. 1, Ed. Willey, Abstract.

During, M.J. et al., "Controlled Release of Dopamine from a Polymeric Brain Implant: In Vivo Characterization," Annals of Neurology, Apr. 1989, p. 351-356, vol. 25, Abstract.

Ellis, V. et al., "Plasminogen Activation by Receptor-Bound Urokinase," Semin. Thromb. Haemost., Jul. 1991, pp. 194-200, vol. 17, No. 3.

Festuccia, C. et al., "Plasminogen Activator Activities in Short-Term Tissue Cultures of Benign Prostatic Hyperplasia and Prostatic Carcinoma," Oncology Research, 1995, pp. 131-138, vol. 7, Nos. 3-4.

Ginsburg, D. et al., "cDNA Cloning of Human Plasminogen Activator-Inhibitor from Endothelial Cells," J. Clin. Invest., 1986, pp. 1673-1680, vol. 78.

Goldspiel, B.R. et al., "Human Gene Therapy," Clinical Pharmacy, Jul. 1993, pp. 488-505, vol. 12, No. 7, Abstract.

Grisendi, S. et al., "Nucleophosmin and Cancer," Nature Reviews Cancer, Jul. 2006, pp. 493-505, vol. 6, Abstract.

Guex, N. et al., "SWISS-MODEL and the Swiss-Pbd Viewer: An Environment for Comparative Protein Modeling," Electroporesis, 1997, pp. 2714-2723, vol. 18, Issue 15, Abstract.

Hajjar, K.A. et al., "Identification and Characterization of Human Endothelial Cell Membrane Binding Sites for Tissue Plasminogen Activator and Urokinase," J. Biol. Chem., Feb. 1990, pp. 2908-2916, vol. 265, No. 5.

Hammes, H.-P. et al., "Subcutaneous Injection of a Cyclic Peptide Antagonist of Vitronectin Receptor-Type Integrins Inhibits Retinal Neovascularization," Nature Medicine, May 1996, p. 529, vol. 2, No. 5, Abstract.

Hann, B. et al., "Building 'Validated' Mouse Models of Human Cancer," Current Opinion in Cell Biology, Dec. 2001, pp. 778-784, vol. 13, Issue 6, Abstract.

Hekman, C.M. et al., "Bovine Plasminogen Activator Inhibitor 1: Specificity Determinations and Comparison of the Active, Latent, and Guanidine-Activated Forms," Biochemistry, Apr. 1988, pp. 2911-2918, vol. 27, No. 8.

Hekman, C.M. et al., "Endothelial Cells Produce a Latent Inhibitor of Plasminogen Activators that can be Activated by Denaturants," J. Biol. Chem., Sep. 1985, pp. 11581-11587, vol. 260, No. 21.

Ho, S.N. et al., "Site-Directed Mutagenesis by Overlap Extension Using the Polymerase Chain Reaction," Gene, 1989, pp. 51-59, vol. 77.

Hopp, T.P. et al., "Prediction of Protein Antigenic Determinants from Amino Acid Sequences," Proc. Natl. Acad. Sci., Jun. 1981, p. 3824-3828, vol. 78, No. 6.

Howard III, M.A. et al., "Acute Subdural Hematomas: An Age-Dependent Clinical Entity," J. Neurosurg., Dec. 1989, vol. 71, No. 6, Abstract.

Hoylaerts, M. et al., "Kinetics of the Activation of Plasminogen by Human Tissue Plasminogen Activator," J. Biol. Chem., Mar. 1982, pp. 2912-2919, vol. 257, No. 6.

Hsueh, et al., "Molecular Mechanisms in the Hormonal Regulation of Plasminogen Activator Activity in Ovarian Granulosa Cells and Cumulus-Oocyte Complexes," Melotic Inhibition: Molecular Control of Melosis, 1988, pp. 227-257, vol. 267, Ed. Alan R. Liss, Inc.

Huse, W.D. et al., "Generation of a Large Combinatorial Library of the Immunoglobulin Repertoire in Phage Lambda," Science, Dec. 1989, pp. 1275-1281, vol. 246, No. 4935, Abstract.

Hutchison, C.A. et al., "Mutagenesis at a Specific Position in a DNA Sequence," The Journal of Biological Chemistry, Sep. 1978, pp. 6551-6560, vol. 253, No. 18.

Ii, et al., "Role of Matrix Metalloproteinase-7 (Matrilysin) in Human Cancer Invasion, Apoptosis, Growth, and Angiogenesis," Exp. Biol. Med., 2006, pp. 20-27, vol. 231.

Im, H. et al., "Bypassing the Kinetic Trap of Serpin Protein Folding by Loop Extension," Protein Science, 2000, pp. 1497-1502, vol. 9.

Inoue, M. et al., "Plasminogen Activator Inhibitor-1 (PAI-1) Gene Transfection Inhibits the Liver Metastasis of Pancreatic Cancer by Preventing Angiogenesis," Oncology Reports, Dec. 2005, pp. 1445-1451, vol. 14.

| | | 10 | 20 | 30 | 40 | 50 | 60 | |
|---|---|---|---|---|---|---|---|---|
| 1B3K(wtPAI-1) | 1 | MQMSPALTCL | VLGLALVFGE | GSAVHHPPSY | VAHLASDFGV | RVFQQVAQAS | KDRNVVFSPY | 60 |
| VLHL | 1 | MQMSPALTCL | VLGLALVFGE | GSAVHHPPSY | VAHLASDFGV | RVFQQVAQAS | KDRNVVFSPY | 60 |
| VLHL<sub>NS</sub> | 1 | MQMSPALTCL | VLGLALVFGE | GSAVHHPPSY | VAHLASDFGV | RVFQQVAQAS | KDRNVVFSPY | 60 |
| VLHL<sub>NV</sub> | 1 | MQMSPALTCL | VLGLALVFGE | GSAVHHPPSY | VAHLASDFGV | RVFQQVAQAS | KDRNVVFSPY | 60 |
| VLHL<sub>NV,NS</sub> | 1 | MQMSPALTCL | VLGLALVFGE | GSAVHHPPSY | VAHLASDFGV | RVFQQVAQAS | KDRNVVFSPY | 60 |
| VLHL<sub>NT</sub> | 1 | MQMSPALTCL | VLGLALVFGE | GSAVHHPPSY | VAHLASDFGV | RVFQQVAQAS | KDRNVVFSPY | 60 |
| VLHL<sub>NT,NS</sub> | 1 | MQMSPALTCL | VLGLALVFGE | GSAVHHPPSY | VAHLASDFGV | RVFQQVAQAS | KDRNVVFSPY | 60 |
| mini-VLHL | 1 | MQMSPALTCL | VLGLALVFGE | GSAVHHPPSY | VAHLASDFGV | RVFQQVAQAS | KDRNVVFSPY | 60 |
| mini-VLHL<sub>NS</sub> | 1 | MQMSPALTCL | VLGLALVFGE | GSAVHHPPSY | VAHLASDFGV | RVFQQVAQAS | KDRNVVFSPY | 60 |
| mini-VLHL<sub>NT</sub> | 1 | MQMSPALTCL | VLGLALVFGE | GSAVHHPPSY | VAHLASDFGV | RVFQQVAQAS | KDRNVVFSPY | 60 |
| mini-VLHL<sub>NT,NS</sub> | 1 | MQMSPALTCL | VLGLALVFGE | GSAVHHPPSY | VAHLASDFGV | RVFQQVAQAS | KDRNVVFSPY | 60 |
| 1B3K(wtPAI-1) | 61 | GVASVLAMLQ | LTTGGETQQQ | IQAAMGFKID | VAHLASDFGV(DKGMAPALRH) | LYKELMGPWN | KDEISTTDAI | 120 |
| VLHL | 61 | GVASVLAMLQ | LTTGGETQQQ | IQAAMGFKID | DKGMAPALRH | LYKELMGPWN | KDEISTTDAI | 120 |
| VLHL<sub>NS</sub> | 61 | GVASVLAMLQ | LTTGGETQQQ | IQAAMGFKID | DKGMAPALRH | LYKELMGPWN | KDEISTTDAI | 120 |
| VLHL<sub>NV</sub> | 61 | GVASVLAMLQ | LTTGGETQQQ | IQAAMGFKID | DKGMAPALRH | LYKELMGPWN | KDEISTTDAI | 120 |
| VLHL<sub>NV,NS</sub> | 61 | GVASVLAMLQ | LTTGGETQQQ | IQAAMGFKID | DKGMAPALRH | LYKELMGPWN | KDEISTTDAI | 120 |
| VLHL<sub>NT</sub> | 61 | GVASVLAMLQ | LTTGGETQQQ | IQAAMGFKID | DKGMAPALRH | LYKELMGPWN | KDEISTTDAI | 120 |
| VLHL<sub>NT,NS</sub> | 61 | GVASVLAMLQ | LTTGGETQQQ | IQAAMGFKID | DKGMAPALRH | LYKELMGPWN | KDEISTTDAI | 120 |
| mini-VLHL | 61 | GVASVLAMLQ | LTTGGETQQQ | IQAAMGFKID | DKGMAPALRH | LYKELMGPWN | KDEISTTDAI | 120 |
| mini-VLHL<sub>NS</sub> | 61 | GVASVLAMLQ | LTTGGETQQQ | IQAAMGFKID | DKGMAPALRH | LYKELMGPWN | KDEISTTDAI | 120 |
| mini-VLHL<sub>NT</sub> | 61 | GVASVLAMLQ | LTTGGETQQQ | IQAAMGFKID | DKGMAPALRH | LYKELMGPWN | KDEISTTDAI | 120 |
| mini-VLHL<sub>NT,NS</sub> | 61 | GVASVLAMLQ | LTTGGETQQQ | IQAAMGFKID | DKGMAPALRH | LYKELMGPWN | KDEISTTDAI | 120 |
| 1B3K(wtPAI-1) | 121 | FVQRDLKLVQ | GFMPHFFRLF | RSTVKQVDFS | EVERARFIIN | DWVKTHTKGM | ISNLLGKGAV | 180 |
| VLHL | 121 | FVQRDLKLVQ | GFMPHFFRLF | RSTVKQVDFS | EVERARFIIN | DWVKTHTKGM | ISNLLGKGAV | 180 |
| VLHL<sub>NS</sub> | 121 | FVQRDLKLVQ | GFMPHFFRLF | RSTVKQVDFS | EVERARFIIN | DWVKTHTKGM | ISNLLGKGAV | 180 |
| VLHL<sub>NV</sub> | 121 | FVQRDLKLVQ | GFMPHFFRLF | RSTVKQVDFS | EVERARFIIN | DWVKTHTKGM | ISNLLGKGAV | 180 |
| VLHL<sub>NV,NS</sub> | 121 | FVQRDLKLVQ | GFYSHFFRLF | RSTVKQVDFS | EVERARFIIN | DWVKTHTKGM | ISNLLGKGAV | 180 |
| VLHL<sub>NT</sub> | 121 | FVQRDLKLVQ | GFMPHFFRLF | RSTVKQVDFS | EVERARFIIN | DWVKTHTKGM | ISNLLGKGAV | 180 |
| VLHL<sub>NT,NS</sub> | 121 | FVQRDLKLVQ | GFMPHFFRLF | RSTVKQVDFS | EVERARFIIN | DWVKTHTKGM | ISNLLGKGAV | 180 |
| mini-VLHL | 121 | FVQRDL | | | | | | |
| mini-VLHL<sub>NS</sub> | 121 | FVQRDL | | | | | | |
| mini-VLHL<sub>NT</sub> | 121 | FVQRDL | | | | | | |
| mini-VLHL<sub>NT,NS</sub> | 121 | FVQRDL | | | | | | |

FIG. 1A

```
1B3K(wtPAI-1)      181 DQLTRLVLVN ALYFNGQWKT PFPDSSTHRR LFHKSDGSTV SVPMMAQTNK FNYTEFTTPD 240
VLHL               181 DQLTRLVLVN ALYFNGQWKT PFPDSSTHRR LFHKSDGSTV SVPMMAQTNK FNYTEFTTPD 240
VLHL_NS            181 DQLTRLVLVN ALYFNGQWKT PFPDSSTHRR LFHKSDGSTV SVPMMAQTNK FNYTEFTTPD 240
VLHL_NV            181 DQLTRLVLVN ALYFNGQWKT PFPDSSTHRR LFHKSDGSTV SVPMMAQTNK FNYTEFTTPD 240
VLHL_NV,NS         181 DQLTRLVLVN ALYFNGQWKT PFPDSSTHRR LFHKSDGSTV SVPMMAQTNK FNYTEFTTPD 240
VLHL_NT            181 DQLTRLVLVN ALYFNGQWKT PFPDSSTHRR LFHKSDGSTV SVPMMAQTNK FNYTEFTTPD 240
VLHL_NT,NS         181 DQLTRLVLVN ALYFNGQWKT PFPDSSTHRR LFHKSDGSTV SVPMMAQTNK FNYTEFTTPD 240
mini-VLHL          181 -QLTRLVLVN ALYFNGQWKT PFPDSSTHRR LFHKSDGSTV SVPMMAQTNK FNYTEFTTPD 240
mini-VLHL_NS       181 -QLTRLVLVN ALYFNGQWKT PFPDSSTHRR LFHKSDGSTV SVPMMAQTNK FNYTEFTTPD 240
mini-VLHL_NT       181 -QLTRLVLVN ALYFNGQWKT PFPDSSTHRR LFHKSDGSTV SVPMMAQTNK FNYTEFTTPD 240
mini-VLHL_NT,NS    181 -QLTRLVLVN ALYFNGQWKT PFPDSSTHRR LFHKSDGSTV SVPMMAQTNK FNYTEFTTPD 240

1B3K(wtPAI-1)      241 GHYYDILELP YHGDTLSMFI AAPYEKEVPL SALTNILSAQ LISHWKGNMT RLPRLLVLPK 300
VLHL               241 GHYYDILELP YHGDTLSMFI AAPYEKEVPL SALTNILSAQ LISHWKGNMT RLPRLLVLPK 300
VLHL_NS            241 GHYYDILELP YHGDTLSMFI AAPYEKEVPL SALTNILSAQ LISHWKGNMT RLPRLLVLPK 300
VLHL_NV            241 GHYYDILELP YHGDTLSMFI AAPYEKEVPL SALTNILSAQ LISHWKGNMT RLPRLLVLPK 300
VLHL_NV,NS         241 GHYYDILELP YHGDTLSMFI AAPYEKEVPL SALTNILSAQ LISHWKGNMT RLPRLLVLPK 300
VLHL_NT            241 GHYYDILELP YHGDTLSMFI AAPYEKEVPL SALTNILSAQ LISHWKGNMT RLPRLLVLPK 300
VLHL_NT,NS         241 GHYYDILELP YHGDTLSMFI AAPYEKEVPL SALTNILSAQ LISHWKGNMT RLPRLLVLPK 300
mini-VLHL          241 GHYYDILELP YHGDTLSMFI AAPYEKEVPL SALTNILSAQ LISHWKGNMT RLPRLLVLPK 300
mini-VLHL_NS       241 GHYYDILELP YHGDTLSMFI AAPYEKEVPL SALTNILSAQ LISHWKGNMT RLPRLLVLPK 300
mini-VLHL_NT       241 GHYYDILELP YHGDTLSMFI AAPYEKEVPL SALTNILSAQ LISHWKGNMT RLPRLLVLPK 300
mini-VLHL_NT,NS    241 GHYYDILELP YHGDTLSMFI AAPYEKEVPL SALTNILSAQ LISHWKGNMT RLPRLLVLPK 300

1B3K(wtPAI-1)      301 FSLETEVDLR KPLENLGMTD MFRQFQADFT SLSDQEPLHV AQALQKVKIE VNESGTVASS 360
VLHL               301 FSLETEVDLR KPLENLGMTD MFRQFQADFT SLSDQEPLHV AQALQKVKIE VNESGTVASS 360
VLHL_NS            301 FSLETEVDLR KPLENLGMTD MFRQFQADFT SLSDQEPLHV AQALQKVKIE VNESCTVASS 360
VLHL_NV            301 FSLETEVDLR KPLENLGMTD MFRQFQADFT SLSDQEPLHV AQALQKVKIE VNESGTVASS 360
VLHL_NV,NS         301 FSLETEVDLR KPLENLGMTD MFRQFQADFT SLSDQEPLHV AQALQKVKIE VNESCTVASS 360
VLHL_NT            301 FSLETEVDLR KPLENLGMTD MFRQFQADFT SLSDQEPLHV AQALQKVKIE VPESGTVASS 360
VLHL_NT,NS         301 FSLETEVDLR KPLENLGMTD MFRQFQADFT SLSDQEPLHV AQALQKVKIE VPESCTVASS 360
mini-VLHL          301 FSLETEVDLR KPLENLGMTD MFRQFQADFT SLSDQEPLHV AQALQKVKIE VNESGTVASS 360
mini-VLHL_NS       301 FSLETEVDLR KPLENLGMTD MFRQFQADFT SLSDQEPLHV AQALQKVKIE VNESCTVASS 360
mini-VLHL_NT       301 FSLETEVDLR KPLENLGMTD MFRQFQADFT SLSDQEPLHV AQALQKVKIE VPESGTVASS 360
mini-VLHL_NT,NS    301 FSLETEVDLR KPLENLGMTD MFRQFQADFT SLSDQEPLHV AQALQKVKIE VPESCTVASS 360
```

FIG.1B

| | | |
|---|---|---|
| 1B3K(wtPAI-1) | 361 | STAVIVSARM APEEIIMDRP FLFVVRHNPT GTVLFMGQVM EP |
| VLHL | 361 | STAVIVSARM APEEIIMDRP FLFVVRHNPT GTVLFMGQVM EP |
| $VLHL_{NS}$ | 361 | STAVIVSAAM APEEIIMDRP FLFVVRHNPT GTVLFMGQVM EP |
| $VLHL_{NV}$ | 361 | STAVIVSARM APEEIIMDRP FLFVVRHNPT GTVLFMGQVM EP |
| $VLHL_{NV,\ NS}$ | 361 | STAVIVSAAM APEEIIMDRP FLFVVRHNPT GTVLFMGQVM EP |
| $VLHL_{NT}$ | 361 | STAVIVSARM APEEIIMDRP FLFVVRHNPT GTVLFMGQVM EP |
| $VLHL_{NT,\ NS}$ | 361 | STAVIVSAAM APEEIIMDRP FLFVVRHNPT GTVLFMGQVM EP |
| mini-VLHL | 361 | STAVIVSARM APEEIIMDRP FLFVVRHNPT GTVLFMGQVM EP |
| mini-$VLHL_{NS}$ | 361 | STAVIVSAAM APEEIIMDRP FLFVVRHNPT GTVLFMGQVM EP |
| mini-$VLHL_{NT}$ | 361 | STAVIVSARM APEEIIMDRP FLFVVRHNPT GTVLFMGQVM EP |
| mini-$VLHL_{NT,\ NS}$ | 361 | STAVIVSAAM APEEIIMDRP FLFVVRHNPT GTVLFMGQVM EP |

MODIFIED PLASMINOGEN ACTIVATOR INHIBITOR TYPE-1 MOLECULE AND METHODS BASED THEREON

CROSS-REFERENCE TO RELATED APPLICATIONS

This application is the National Stage application under 35 U.S.C. §371 of International Application No. PCT/US2008/005272, filed Apr. 24, 2008, which claims the benefit of priority of U.S. Provisional Application Ser. No. 60/926,797, filed Apr. 27, 2007.

The invention was made in part with government support under National Institutes of Health: CA90524 and CA109625. The government has certain rights in the invention.

1. FIELD OF THE INVENTION

Generally presented herein are modified plasminogen activator inhibitor type-1 (PAI-1) molecules that display an increased in vivo half-life of the active form of the PAI-1 molecules, but are deficient in one or more functional activities as compared to wild-type PAI-1 protein. For example, the modified PAI-1 molecule can display an increased half-life, and further display at least one of the following characteristics: (i) decreased binding activity to at least one of the following molecules: urokinase plasminogen activator (uPA), tissue plasminogen activator (IPA) and vitronectin (Vn); and (ii) decreased specific activity against at least one of the following molecules: uPA, tPA and Vn. Also presented herein are peptides of such modified molecules, antibodies that specifically bind the modified PAI-1 molecules, nucleic acid molecules, particularly DNA, encoding the modified PAI-1 molecules, host cells containing such nucleic acid molecules, and methods for producing modified PAI-1 molecules. Also presented herein are compositions comprising modified PAI-1 molecules and methods of using the modified PAI-1 molecules and compositions. The modified PAI-1 molecules may be used, for example, to inhibit angiogenesis in a subject, thereby treating diseases or conditions associated with undesired angiogenesis, to inhibit cell proliferation, and/or to promote blood clotting.

2. BACKGROUND OF THE INVENTION

During carcinogenesis, malignant cells with abnormally high proteolytic activity degrade extracellular matrix proteins facilitating invasion and metastasis. In cancer-related angiogenesis, proteolytic activity is high at the tip of the capillary vessels, which allows the formation of a dense network of neovasculature in the proximity of the tumor mass to support cancer growth (Lah et al., 2006, *Expert Opin Biol Ther* 6:257-279; Ludwig, 2005, *Bioessays* 27:1181-1191). Consequently, inhibition of proteolysis has been explored as a therapeutic option to limit invasion, metastasis and angiogenesis (Schirrmacher, 1985, *Adv Cancer Res* 43:1-73; Swiercz et al., 2001, *Oncol Rep* 8:463-470; Vihinen et al., 2005, *Curr Cancer Drug Targets* 5:203-220).

Attention has been concentrated on the inhibition of metalloproteinases. Certain metalloproteinase inhibitors are in the clinical studies (Arlen et al., 2006, *Clin Cancer Res* 12:1260-1269; Lara et al., 2006, *Clin Cancer Res* 12:1556-1563; Molina et al., 2005, *Anticancer Drugs* 16:997-1002).

Much less consideration has been paid to inhibition of enzymes leading to formation of plasmin, an enzyme that can either directly or indirectly hydrolyze many extracellular domain proteins. Plasmin is produced from plasminogen by the plasminogen activators, urokinase plasminogen activator (uPA) and tissue plasminogen activator (tPA). Certain plasmin inhibitors have also shown strong anticancer activity in preclinical studies (Chorostowska-Wynimko et al., 2003, *Mol Cancer Ther* 2:19-28; Jedinak et al., 2005, *Neoplasma* 52:185-192; Puli et al., 2006, *J Neurooncol*).

For example, inhibitors of uPA prevent plasmin formation and consequently limit cancer growth by blocking angiogenesis (Swiercz et al., 2001, *Oncol Rep* 8:463-470; Inoue et al., 2005, *Oncol. Rep.* 14:1445-1451; van Hinsbergh et al., 2006, *Arterioscler Thromb Vasc Biol* 26:716-728). Inhibitors or uPA, however, are generally considered toxic or labile.

In addition, modified PAI-1 molecules have been identified that exhibit an increased half-life of the active form (US2005/0158295A1). PAI-1 is a member of the super-class of Serine Protease Inhibitors (serpin) that inhibits uPA and tPA activity, increasing the half-life of the active (versus latent) form of PAI-1 is useful in cancer therapy.

Given the importance of proteases and proteolytic cascades in the cancer process, a need continues to exist for the identification and development of appropriate modulators thereof.

3. SUMMARY OF THE INVENTION

The present invention relates to the modified PAI-1 molecules that have an increased half-life of the active form, but are deficient in one or more functional activities as compared to a wild-type PAI-1 protein.

For example, the modified PAI-1 molecules of the present invention can exhibit an increased half-life of the active form and can exhibit at least one of the following characteristics: (i) decreased binding to at least one of the following molecules: uPA, tPA and Vn; and (ii) decreased specific activity against at least one of the following molecules: uPA, tPA and Vn.

The modified PAI-1 molecule comprises one or more amino acid substitutions, deletions, or insertions that abolish or decrease one or more functional activities as compared to wild-type PAI-1 protein. In certain embodiments, the modified PAI-1 molecules have decreased binding to uPA, tPA or Vn. In certain embodiments, the modified PAI-1 molecules have decreased specific activity against uPA, tPA or vitronectin. In certain embodiments, the modified PAI-1 molecules have decreased serpin activity.

In one embodiment wherein a modified PAI-1 molecule exhibits an increased half-life of the active form, the modified PAI-1 molecule comprises or forms one or more intramolecular bonds that contribute to this increased half-life. These intramolecular bonds may include, for example, non-covalent bonds, covalent bonds, disulfide bonds, salt bridge, hydrogen bonds, pi-pi interaction. In one aspect, the modified PAI-1 molecule that comprises two or more amino acid residues that do not contain a sulfhydryl group that have been replaced with amino acid residues that contain sulfhydryl groups such as, but not limited to, cysteine residues, such that one or more intramolecule disulfide bonds form within the modified PAI-1 molecule. Such modified PAI-1 molecules have a longer in vivo half-life of the active form than a wild-type PAI-1 protein, in which there is no such disulfide bond(s). In one embodiment, these modified PAI-1 molecules are generated, for example, by amino acid substitutions of certain amino acid residues with cysteine residues to produce disulfide bridges linking the A3 strand and the A5 strand of the β-sheet of the PAI-1 protein.

In one embodiment, the modified PAI-1 molecules are generated, for example, by insertions of amino acid residues that contain a sulfhydryl group.

The present invention further provides compositions, including pharmaceutical compositions comprising the modified PAI-1 protein molecules of the invention.

The present invention further provides methods of therapeutic use of modified PAI-1 molecules in psoriasis, inflammatory disorders, diseases and disorders associated with excess angiogenesis, and primary and metastatic neoplastic diseases (e.g., cancer) and cardiovascular disease, particularly diseases and disorders associated with excess fibrinolysis. The modified PAI-1 molecules may be used for inhibition of angiogenesis or inhibition of other functions mediated or influenced by PAI-1, uPA, tPA or Vn, including but not limited to cell proliferation, cell migration, granulation tissue development, and/or inflammation.

In specific embodiments, modified PAI-1 molecules that have decreased binding and specific activity against uPA, and/or tPA, can be used as therapeutic agents to reduce cancer cell growth, and to inhibit primary and metastatic neoplastic diseases.

In other embodiments, modified PAI-1 molecules that display a decrease in binding to or a decrease in specific activity against Vn, such molecules can be used to limit cancer cell motility, invasion, and reduce incidence or severity of metastasis.

In an embodiment the modified PAI-1 molecule comprises an active form, said modified PAI-1 molecule comprises a helix D region, an A3 strand, an A4 strand and an A5 strand, said molecule comprising an amino acid sequence which has at least about 90%-95% identity to SEQ ID NO:2, said molecule comprises: (a) one or more pairs of amino acid residues not present in a corresponding wild-type PAI-1 protein wherein such one or more pairs of amino acid residues contain sulfhydryl groups, such that one or more disulfide bridges form between or within said helix D region, A3 strand, A4 strand and/or A5 strand of said modified PAI-1 molecule; and (b) one or more amino acid substitutions relative to the amino acid sequence of SEQ ID NO:2, wherein the active form of said modified PAI-1 molecule displays: (i) a longer in vivo half-life; and (ii) one or more decreased functional activities, as compared to the active form of a corresponding wild-type PAI-1 protein.

In an embodiment, the modified PAI-1 molecule comprises one or more pairs of amino acid substitution at positions: 31 and 97; (ii) 192 and 347; and (iii) 197 and 355 of the amino acid sequence of a wild-type PAI-1 protein using SEQ ID NO:2 for numbering.

In an embodiment, the modified PAI-1 molecule comprises one or more amino acid substitutions at amino acid positions of a wild-type PAI-1 protein using SEQ ID NO:2 for numbering, such amino acid substitutions are: (i) Gln 146 substituted with amino acid residue Asn, Lys, Arg or His; (ii) Asn 352 substituted with amino acid residue Ala, Pro, Gly or Ser; and (iii) Arg 369 substituted with amino acid residue Ala, Pro, Gly or Ser.

In an embodiment, the modified PAI-1 molecule comprises one or more amino acid substitutions at amino acid positions of a wild-type PAI-1 protein using SEQ ID NO:2 for numbering, such amino acid substitutions are: (i) Gln 78 substituted with amino acid residue Asn, Lys, Arg, His, Ala, Pro, Gly, or Ser; (ii) Phe 132 substituted with amino acid residue Ala, Pro, Gly or Ser; (iii) Met 133 substituted with amino acid residue Thr, Ala, Pro, Gly or Ser; (iv) Leu 139 substituted with amino acid residue Ala, Pro, Gly or Ser; (v) Gln 146 substituted with amino acid residue Asn, Lys, Arg, His, Ala, Pro, Gly, or Ser; and (vi) Thr 167 substituted with amino acid residue Ala, Pro, Gly or Ser.

In an embodiment, the modified PAI-1 molecule comprises an amino acid substitution at Val 364 of the amino acid sequence of a wild-type PAI-1 protein using SEQ ID NO:2 for numbering, the amino acid is substituted with amino acid residue Pro, Ala, Gly or Ser.

In an embodiment, the modified PAI-1 molecule comprises an amino acid substitution at Asn 352 of the amino acid sequence of a wild-type PAI-1 protein using SEQ ID NO:2 for numbering, the amino acid is substituted with amino acid residue Pro, Ala, Gly or Ser.

In an embodiment, the modified PAI-1 molecule comprises one or more amino acid substitutions at amino acid positions of a wild-type PAI-1 protein using SEQ ID NO:2 for numbering, said amino acid substitutions are: (i) Asp 204 substituted with amino acid residue Arg, His, Lys; (ii) Ser 205 substituted with amino acid residue Phe, Tyr, Trp; (iii) Ser 206 substituted with amino acid residue Phe, Tyr, Trp; (iv) Thr 207 substituted with amino acid residue Phe, Tyr, Trp; (v) His 208 substituted with amino acid residue Asn, Gln, Glu; (vi) Arg 209 substituted with amino acid residue Asp, Glu, Gln, or Asn; and (vii) Arg 210 substituted with amino acid residue Asp, Glu, Gln, or Asn.

In certain embodiments, the modified has an in vivo half-life of over 3 hours, 6 hours, 10 hours, 20 hours, 50 hours, 60 hours, 70 hours, 90 hours, 100 hours, 150 hours, 200 hours, 10 days, 12 days, 16 days, 30 days, or 60 days.

In certain embodiments, the modified PAI-1 molecules are $VLHL_{NS}$, $VLHL_{NV}$, $VLHL_{NT}$, $VLHL_{NS,\,NV}$, $VLHL_{NS,\,NT}$, $VLHL_{NV,\,NT}$, or $VLHL_{NS,\,NV,\,NT}$.

In certain embodiments, modified PAI-1 molecule comprises an active form, the modified PAI-1 molecule comprises a helix D region, an A3 strand, an A4 strand and an A5 strand, said molecule comprises an amino acid sequence which has at least about 90% to 95% identity to SEQ ID NO:2, the molecule comprises: (a) one or more pairs of amino acid residues not present in a corresponding wild-type PAI-1 protein wherein such one or more pairs of amino acid residue contain sulfhydryl groups, such that one or more disulfide bridges form between or within said helix D region, A3 strand, A4 strand and/or A5 strand of said modified PAI-1 molecule; and (b) one or more amino acid deletions relative to the amino acid sequence of SEQ ID NO:2, wherein the active form of said modified PAI-1 molecule displays: (i) a longer in vivo half-life; and (ii) one or more decreased functional activities, as compared to an active form of said wild-type PAI-1 protein.

4. DESCRIPTION OF THE FIGURES

FIGS. 1A-1C. Amino acid sequences of wild-type PAI-1 (1B3K/wtPAI-1); VLHL; $VLHL_{NS}$; $VLHL_{NV}$; $VLHL_{NV,NS}$; $VLHL_{NT}$; $VLHL_{NT,NS}$; mini-VLHL; mini $VLHL_{NS}$; mini $VLHL_{NT}$; mini $VLHL_{NT,NS}$. The first 23 amino acid residues are truncated and replaced with His residues tag and linker. Amino acid substitutions are indicated in grey and dark grey.

Figure 2B:
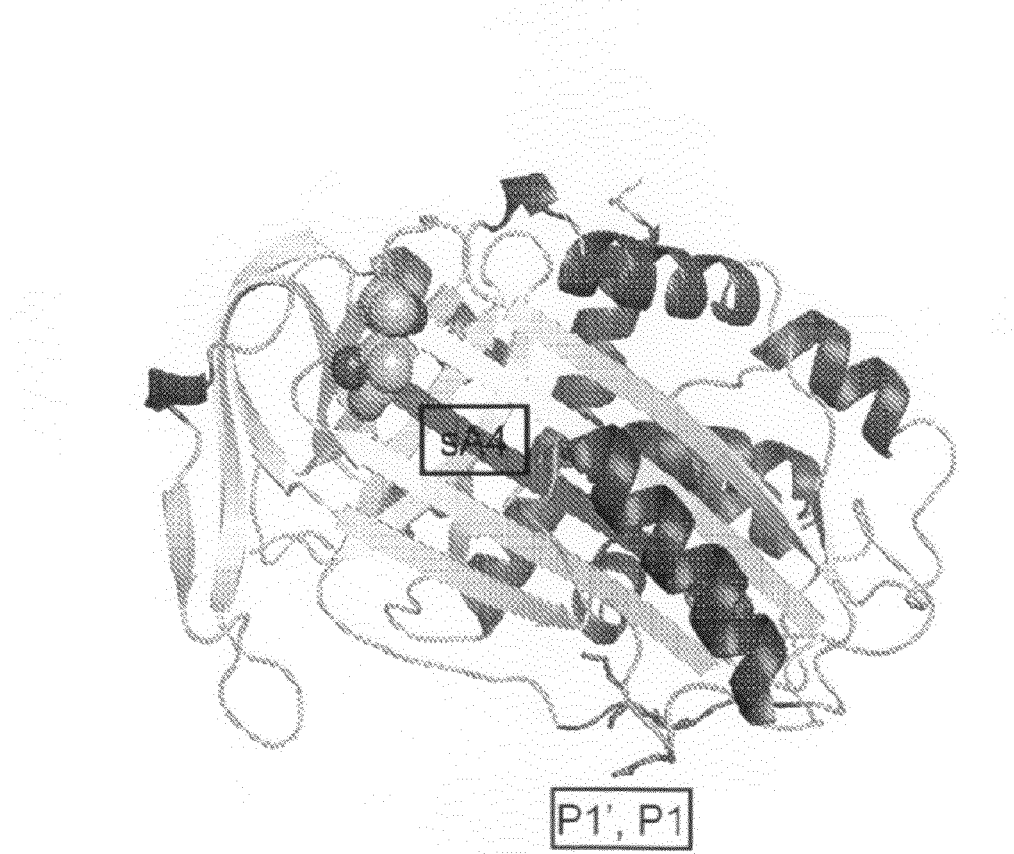

FIGS. 2A & 2B. Ribbon model of PAI-1. (A) In active conformation, PAI-1's reactive center loop is extended from the main body of protein molecule. (B) In latent conformation the reactive center loop is inserted between A3 and A5 strands of PAI-1, turning into strand A4 and is not available for reaction with PAI-1 substrates. P1', P1 (Arg369, Met370) of active site as indicated. Cysteines (shown as spheres) were able to form disulfide bridge and to "freeze" PAI-1 in active conformation. Reduction of the disulfide bridge permits VLHL PAI-1 to convert into latent form as wtPAI-1 does. Models of active PAI-1 and latent form were acquired from X-ray analysis, PAI-1 VHLH was built using CHAIN program. All amino acids are numbered as in notation commonly accepted for thrombin, while some publications and other public database may use a different amino acid numbering system.

Figure 3:
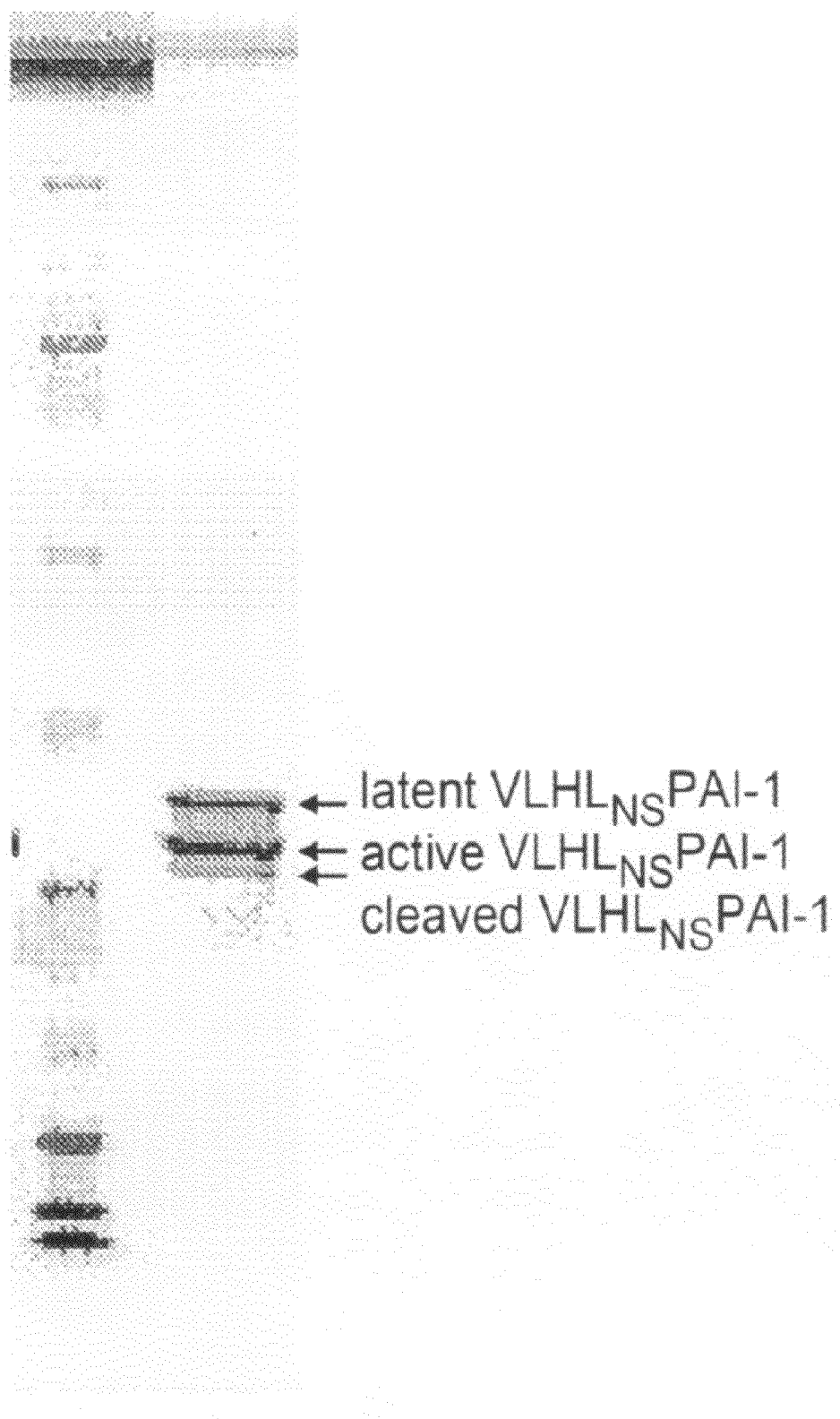

FIG. 3. PAGE gel of purified VLHL$_{NS}$ PAI-1 (no protease inhibitors used). Three different forms of PAI-1 are detected (latent, active and cleaved forms). Similarly, PAGE gel of purified VLHL PAI-1 also shows different forms.

Figure 4:
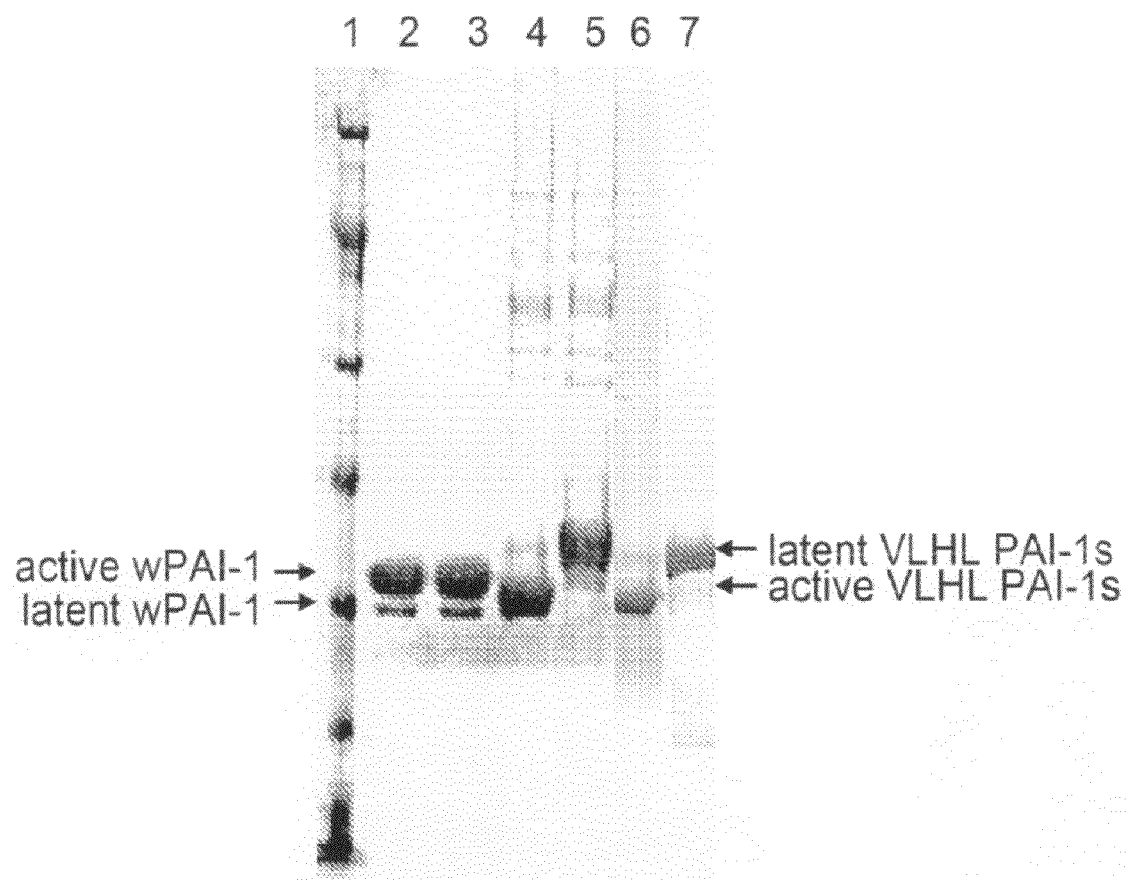

FIG. 4. PAGE electrophoresis of: lane 1—molecular weight standards (from the top 191, 97, 64, 51, 39, 28, 19 and 14 kDa; lane 2—wtPAI-1; lane 3—wtPAI-1 treated with DTT; lane 4—VLHL PAI-1 (active conformation); lane 5—VLHL PAI-1 treated with DTT (latent conformation); lane 6—VLHLNS PAI-1 (in active conformation); lane 7, VLHLNS PAI-1 treated with DTT (latent conformation).

Figure 5:
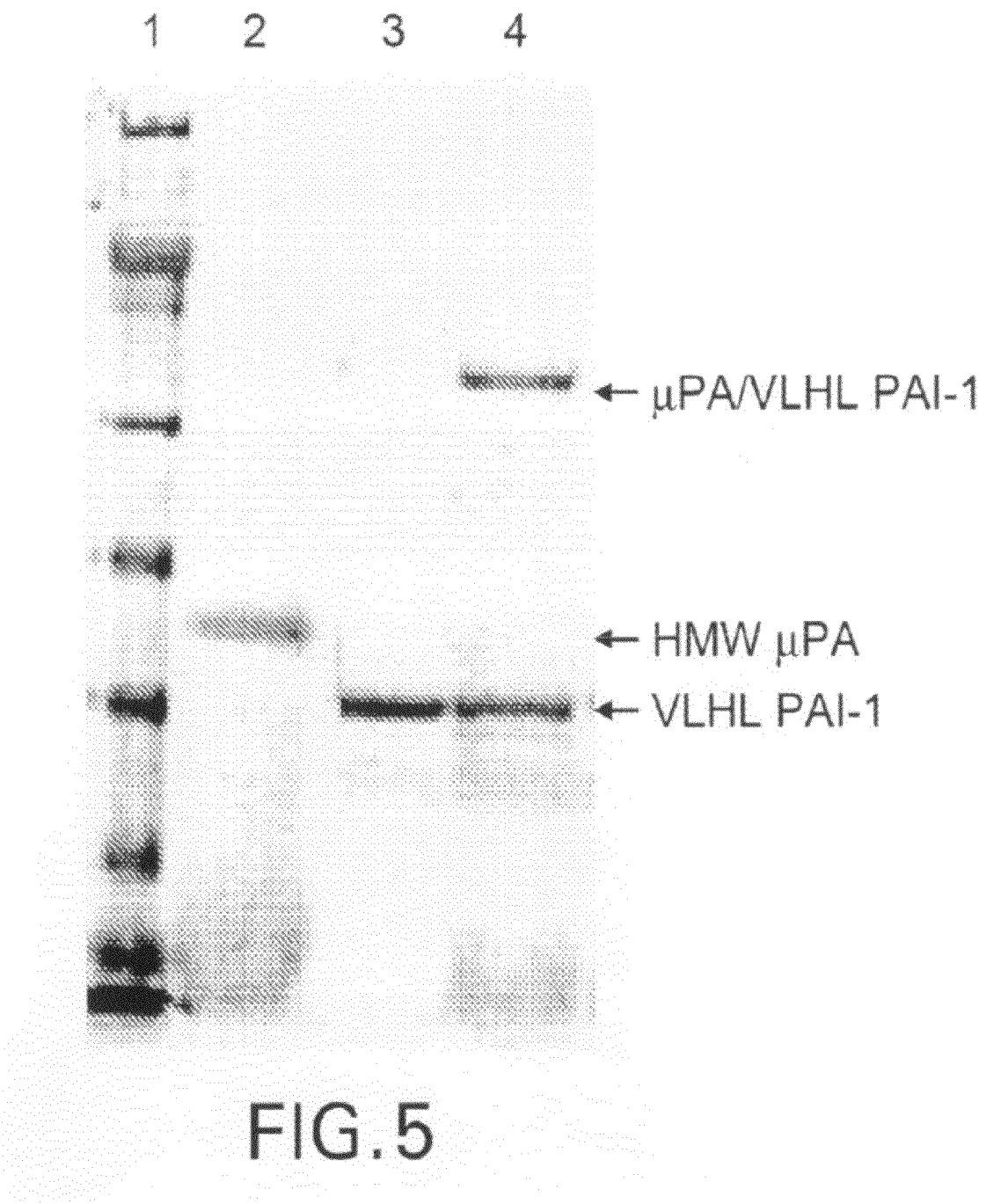

FIG. 5. VLHL PAI-1/uPA complex formation. PAGE electrophoresis of: lane 1—molecular weight standards (from the top 191, 97, 64, 51, 39, 28, 19 and 14 kDa; lane 2—high molecular weight (HMW) uPA (American Diagnostica Inc.); lane 3—VLHL PAI-1; lane 4—mixture of uPA and VLHL PAI-1 and complex of uPA with VLHL PAI-1.

Figure 6:
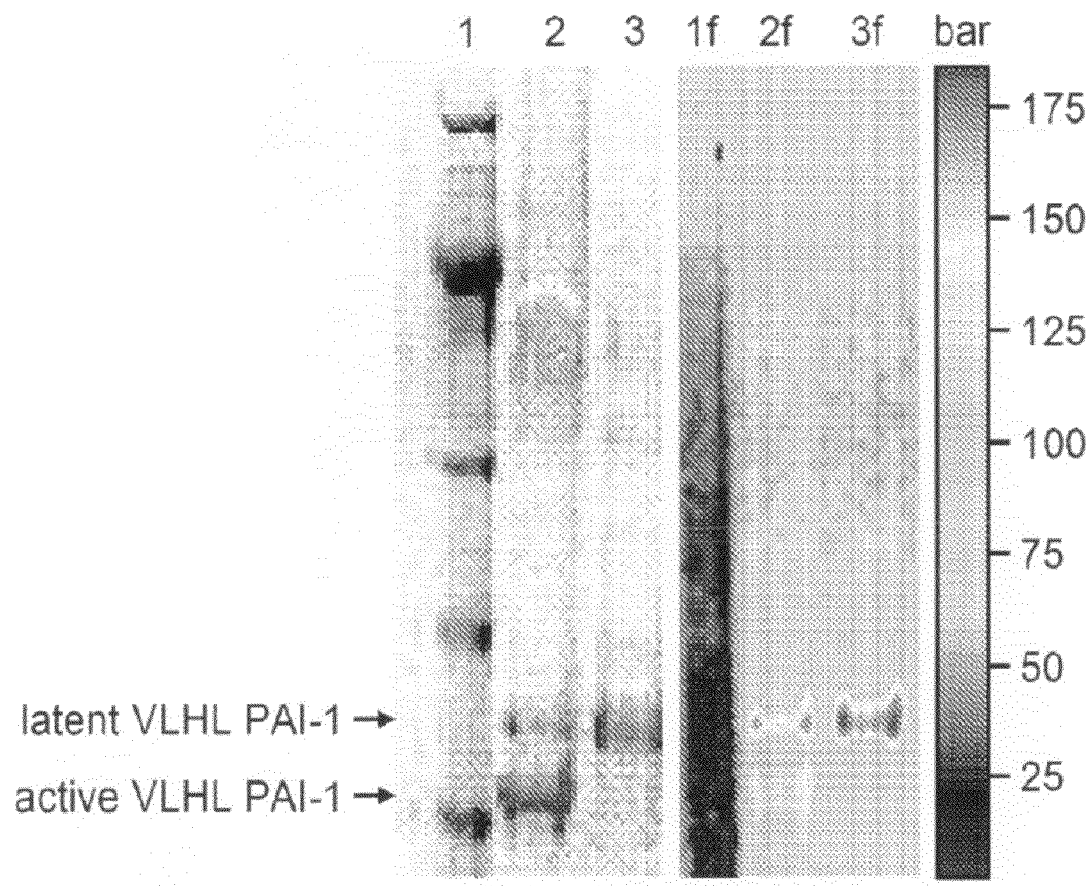

FIG. 6. PAGE electrophoresis of: lane 1, molecular weight standards; lane 2—VLHL PAI-1 in active conformation; lane 3—VLHL PAI-1 treated with DTT (in latent conformation); lane f—fluorescence in grey, UV illuminated; lane 1f—molecular weight standards; lane 2f—VLHL PAI-1 in active conformation; lane 3—VLHL PAI-1-treated with TCEP; bar, grey scale.

Figure 7:
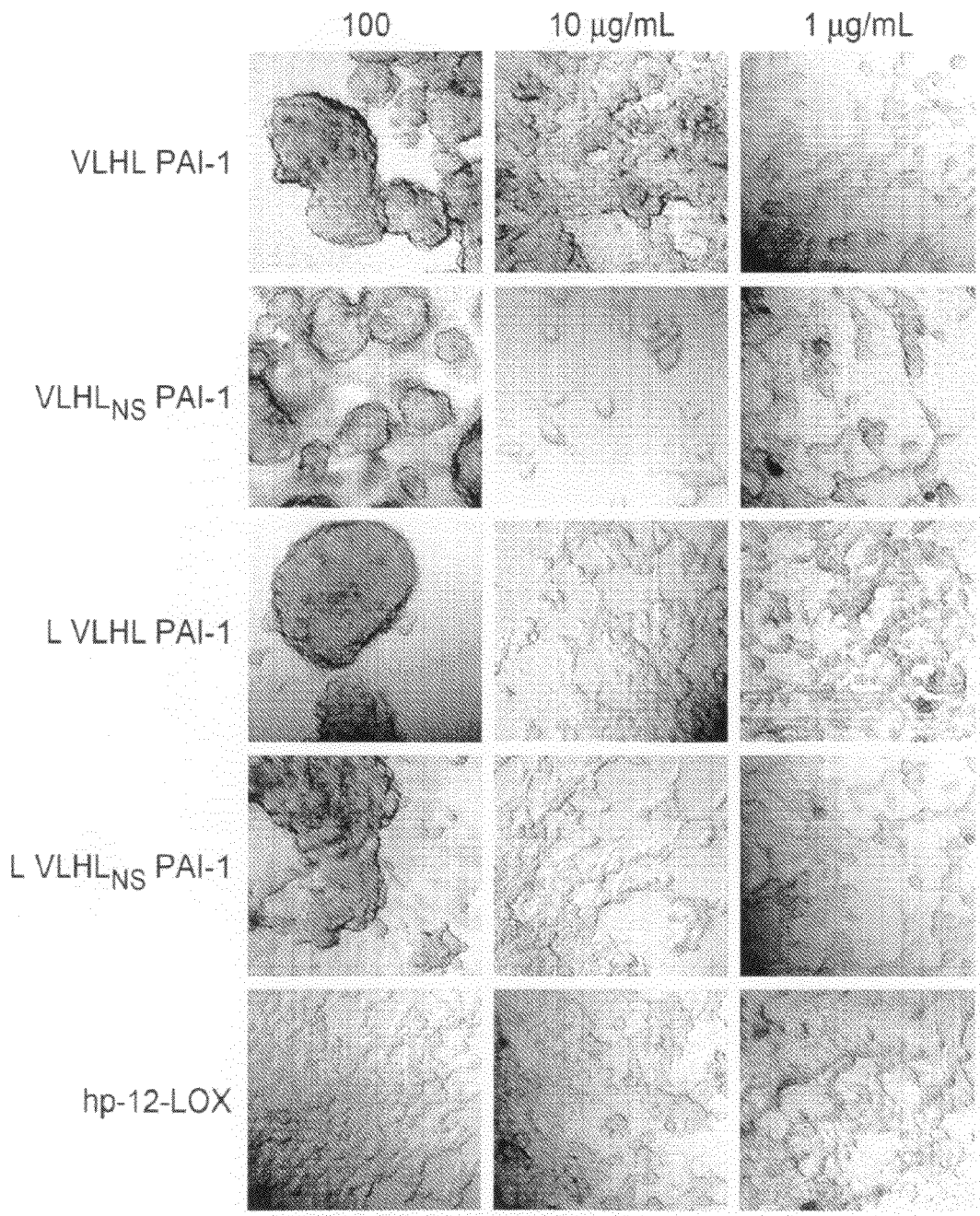

FIG. 7. LnCAP cells treated with VLHL PAI-1s in different conformation and in different concentrations in comparison with control. No differences were seen between non-treated cells and treated with buffer only and insert protein.

Figure 8:
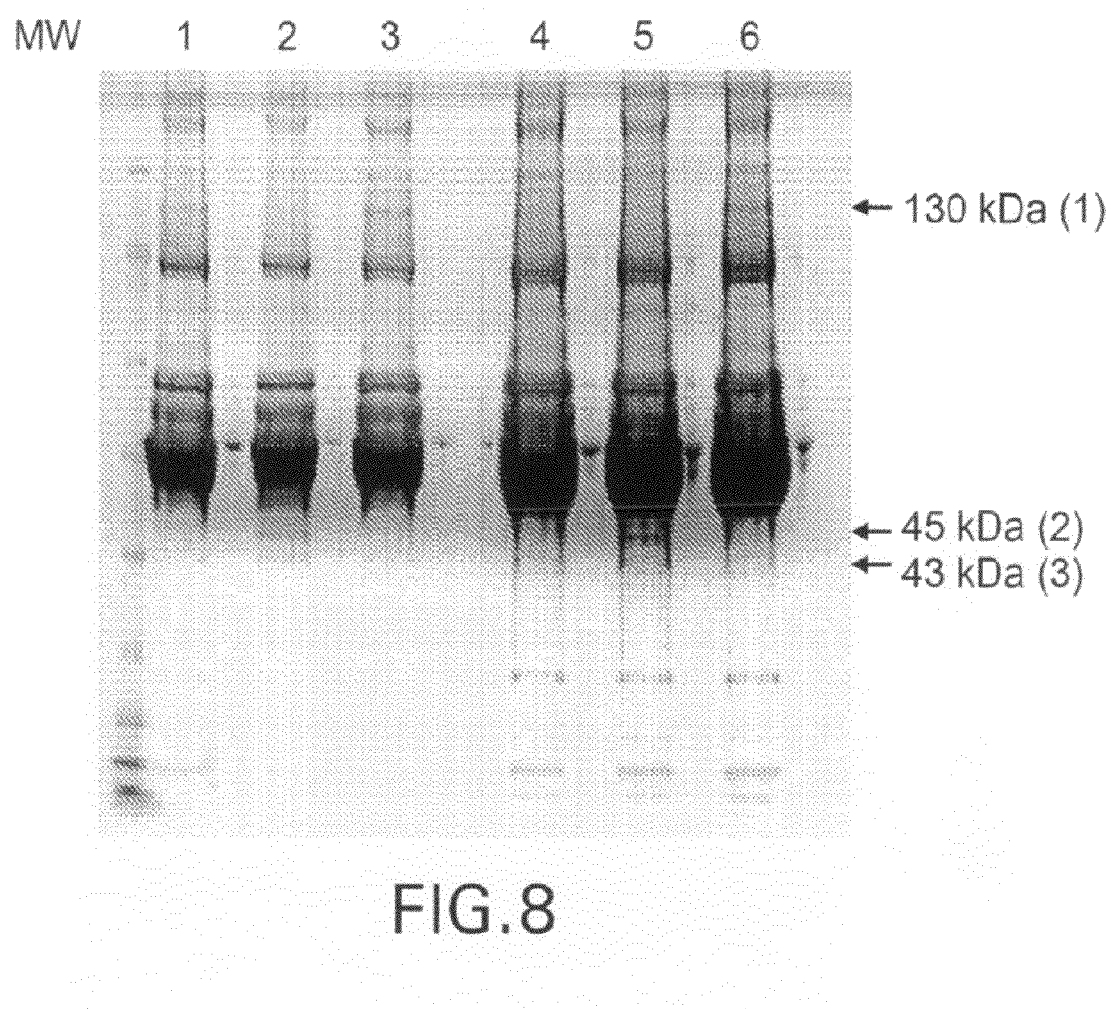

FIG. 8. Acidic wash of cells treated with: lane 1—buffer; lane 2—VLHL PAI-1; lane 3—VLHLNS PAI-1; lane 4—buffer, 3× volume; lane 5—VLHL PAI-1, 3× volume; lane 6—VLHLNS PAI-1, 3× volume; lane MW, molecular weight standards.

Figure 9:
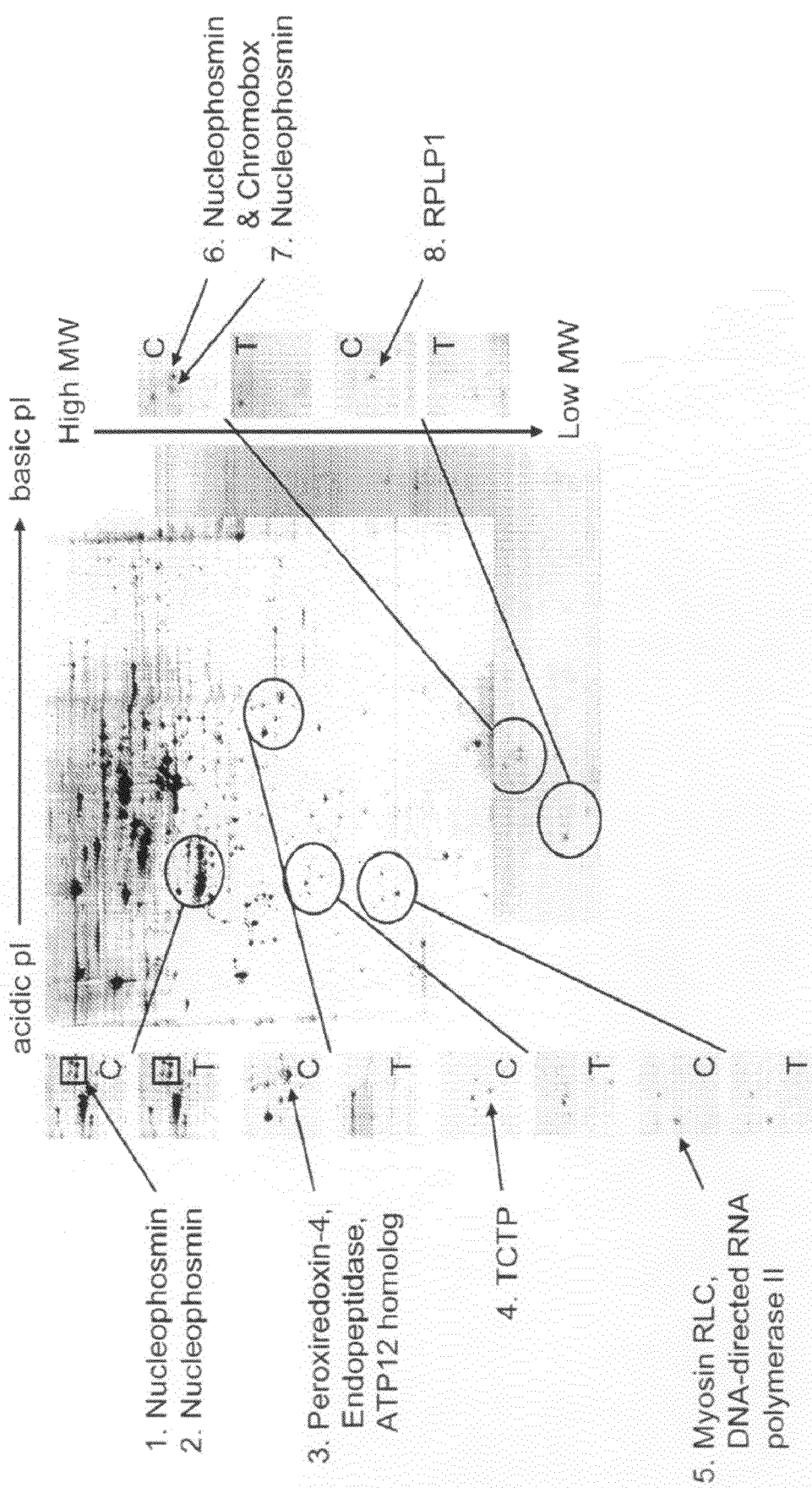

FIG. 9. Coomassie blue-stained 2D PAGE gels, front-control sample, pI 4-7; gel in background-control sample, pI 3-10. All "C" inserts represent control sample; "T" inserts showing gels of VLHL PAI-1-treated cells. In some cases, more than one protein is identified as indicated, for example, in spot 5. Nucleophosmin all four spots were analyzed and in case of two lower spots in addition to other proteins, nucleophosmin was found in control sample but not treated by VLHL PAI-1. Other proteins of four spots were identical. Complete list of proteins detected is in Table 6.

4.1 SEQUENCE LISTING

SEQ ID NO:1 is a nucleotide sequence encoding human PAI-1 with 5' and 3' untranslated regions.

SEQ ID NO:2 is the amino acid sequence of an exemplary human PAI-1 protein, including signal peptide.

SEQ ID NO:3 is the amino acid sequence of an exemplary mature human PAI-1 protein.

SEQ ID NO:4 is the amino acid sequence of an exemplary embodiment of the invention, VLHL.

SEQ ID NO:5 is the amino acid sequence of an exemplary embodiment of the invention, VLHL$_{NS}$.

SEQ ID NO:6 is the amino acid sequence 1B3K.

SEQ ID NO:7 is the amino acid sequence of an exemplary embodiment of the invention, mini VLHL PAI-1.

SEQ ID NO:8 and SEQ ID NO:38 are linker sequences.

SEQ ID NO:9 is the leader sequence of W.T. PAI-1

SEQ ID NO:10 is the amino acid sequence VLHL without linker sequence.

SEQ ID NO:11 is the amino acid sequence of VLHL$_{NS}$ without linker sequence.

SEQ ID NO:12 is the amino acid sequence of an exemplary embodiment of the invention, VLHL$_{NT}$.

SEQ ID NO:13 is the amino acid sequence of an exemplary embodiment of the invention, VLHL$_{NV}$.

SEQ ID NO:14 is the amino acid sequence of an exemplary embodiment of the invention, VLHL$_{NS,NV}$.

SEQ ID NO:15 is the amino acid sequence of an exemplary embodiment of the invention, VLHL$_{NS,NT}$.

SEQ ID NO:16 is the amino acid sequence of an exemplary embodiment of the invention, VLHL$_{NV,NT}$.

SEQ ID NO:17 is the amino acid sequence of an exemplary embodiment of the invention, VLHL$_{NS,NV,NT}$.

SEQ ID NO:18 is the amino acid sequence of an exemplary embodiment of the invention, mini VLHL$_{NS}$.

SEQ ID NO:19 is the amino acid sequence of an exemplary embodiment of the invention, mini VLHL$_{NT}$.

SEQ ID NO:20 is the amino acid sequence of an exemplary embodiment of the invention, mini VLHL$_{NT,NS}$.

SEQ ID NO:21-SEQ ID NO:37 are the amino acid sequences of peptides from Table 2.

4.2 DEFINITIONS

As used herein, the term "modified PAI-1 molecule" includes modified PAI-1 proteins and functionally active fragments, derivatives and analogs thereof.

As used herein, the term "functionally active" or "functional activity" in the context of a modified PAI-1 molecule refers to a modified PAI-1 molecule that displays one or more known functional activities of the wild-type protein, e.g., binding to uPA, tPA and/or Vn, specific activity against uPA, tPA and/or Vn, serpin activity, internalization of uPA/PAR complex, antigenicity, immunogenicity, etc.

As used herein, the term "derivative" in the context of a PAI-1 protein refers to PAI-1 proteins that comprise an amino acid sequence which has been altered by the introduction of amino acid residue substitutions, deletions, and/or additions. The term "derivative" as used herein also refers to PAI-1 proteins which have been modified, i.e., by the covalent attachment of any type of molecule to the proteins, polypeptides, peptides, and antibodies. Unless otherwise indicated, the terms "protein," "peptide," and "polypeptide" are interchangeable. For example, but not by way of limitation, PAI-1 proteins, polypeptides, peptides, may be modified, e.g., by glycosylation, acetylation, pegylation, phosphorylation, amidation, derivatization by known protecting/blocking groups, proteolytic cleavage, linkage to a cellular ligand or other protein, etc. A derivative may, for example, be produced by chemical modifications using techniques known to those of skill in the art, including, but not limited to, specific chemical cleavage, acetylation, formylation, metabolic synthesis of tunicamycin, etc. Further, a derivative may, for example, contain one or more non-classical amino acids. A derivative possesses a similar or identical function as the PAI-1 or modified PAI-1 proteins from which it has been derived.

As used herein, the term "analog" in the context of PAI-1 molecules refers to proteins, polypeptides, and peptides that are structurally analogous to the wild-type PAI-1 proteins, polypeptides and peptides.

As used herein, the term "substitution" refers to the presence of a non-identical amino acid at a given position in an alignment. If the aligned residues have similar physiochemical properties, the substitution is "conservative."

As used herein, the term "insertion" refers to the presence of an additional amino acid residue before or after a given position in an amino acid sequence.

As used herein, the term "similarity" refers to the extent to which nucleotide or protein sequences are related. The extent of similarity between two sequence can be based on percentage sequence identity, and/or conservation.

As used herein, the term "identity" refers to the extent to which nucleotide or protein sequences that are identical to another nucleotide or protein, respectively.

As used herein, the term "mutation" includes insertion, deletion, or substitution.

As used herein, the term "fragment" or "portion" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues, at least 300 contiguous amino acid residues, at least 350 contiguous amino acid residues, at least 400 contiguous amino acid residues of the amino acid sequence of another polypeptide or a protein. In specific embodiments, a fragment or portion refers to a peptide or polypeptide comprising an amino acid sequence of 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-105, 106-110, 111-115, 116-120, 121-150, 151-160, 161-170, 171-180, 181-190, 191-200, 201-220, 220-250, 250-300, 300-400 contiguous amino acid residues of the amino acid sequence of a polypeptide or protein. In a specific embodiment, a fragment retains at least one functional activity of the wild type PAI-1 protein. In another embodiment, a fragment retains at least two, three, four, or five functional activity of the protein.

As used herein, the term "functional fragment" in relation to a modified PAI-1 refers to a peptide or polypeptide comprising an amino acid sequence of at least 5 contiguous amino acid residues, at least 1.0 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues, at least 300 contiguous amino acid residues, at least 350 contiguous amino acid residues, at least 400 contiguous amino acid residues of the amino acid sequence of SEQ ID NO:2, wherein said peptide or polypeptide retains at least one function of the wild-type PAI-1 protein.

As used herein, the term "fusion protein" refers to a polypeptide that comprises an amino acid sequence of a first polypeptide or functional fragment, analog or derivative thereof, and an amino acid sequence of a heterologous protein, polypeptide, or peptide (i.e., a second protein or polypeptide or fragment, analog or derivative thereof different than the first protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent.

As used therein, the term "specific activity" as it refers to a modified PAI-1 molecule or wild-type PAI-1 protein is a measurement of the efficiency of the protein as an inhibitor. It is measured as activity unit per milligram of protein. In particular, specific activity of uPA can be measured using standard technique known by one skilled in the art, e.g., Swiercz et al., 2001, *Oncol Rep.* 8(3):463-70; specific activity of uPA and tPA can be measured using standard technique known by one skilled in the art, e.g., Harvey et al., 1988, *Clin Exp Metastasis* 6(6):431-50.

As used herein, the term "near" refers to 1-5 amino acids; 6-10 amino acids; 11-20 amino acids; 21-30 amino acids. It also refers to a distance of less than 0.5 Å, more than 0.5 Å and not more than 2 Å, more than 2 Å and not more than 4 Å, more than 4 Å and not more than 10 Å, more than 10 Å and not more than 20 Å, more than 20 Å and not more than 40 Å.

As used herein, the term "cancer" refers to a disease involving uncontrolled cell growth. Some of these cancer cells involving cells have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells.

As used herein, the term "metastasis" or "metastases" refers to the spread of cancer from its primary site to other places in the body. The term refers to a condition where cancer cells break away from a primary tumor, penetrate into the lymphatic system and blood vessels, circulate through the bloodstream, and grow in a distant focus (metastasize) in normal tissues elsewhere in the body. Such metastases can include, but are not limited to, micrometastases.

As used herein, the term "effective amount" in the context of administering a therapy refers to the amount of a compound which is sufficient to reduce or ameliorate the progression, severity and/or duration of cancer or one or more symptoms thereof, prevent the development, recurrence or onset of cancer or one or more symptoms thereof, prevent the advancement or spread of cancer or one or more symptoms thereof, or enhance or improve the prophylactic or therapeutic effect(s) of another therapy.

As used herein, a "therapeutically effective amount" refers to that amount of the therapeutic agent sufficient to destroy, modify, control or remove primary, regional or metastatic cancer tissue. A therapeutically effective amount may refer to the amount of therapeutic agent sufficient to slow down, reduce or stop replication of treated cells relative to untreated cells. A therapeutically effective amount may refer to the amount of therapeutic agent sufficient to delay or minimize the spread of cancer or metastasis. A therapeutically effective amount may also refer to the amount of the therapeutic agent that provides a therapeutic benefit in the treatment or management of cancer. Further, a therapeutically effective amount with respect to a therapeutic agent of the invention means that amount of therapeutic agent alone, or in combination with other therapies, that provides a therapeutic benefit in the treatment or management of cancer. Used in connection with an amount of a therapeutic agent of the invention, the term can encompass an amount that improves overall therapy, reduces or avoids unwanted effects, or enhances the therapeutic efficacy of or synergies with another therapeutic agent. A therapeutically effective amount of a therapeutic agent reduces the progression of cancer by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control such as phosphate buffered saline ("PBS").

As used herein, the term "in combination" refers to the use of more than one therapy (e.g., prophylactic and/or therapeutic agents). The use of the term "in combination" does not restrict the order in which therapies (e.g., prophylactic and/or therapeutic agents) are administered to a subject with cancer. A first therapy (e.g., a prophylactic or therapeutic agent) can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject which had, has, or is susceptible to cancer. The therapies (e.g., prophylactic or therapeutic agents) are administered to a subject in a sequence and within a time interval such that the therapy of the invention can act together with the other therapy to provide an increased benefit than if they were administered otherwise. Any additional therapy (e.g., prophylactic or therapeutic agent) can be administered in any order with the other additional therapies (e.g., prophylactic or therapeutic agents).

In one embodiment, "treat" or "manage" refers to an amelioration of a disease or disorder, or at least one discernible symptom thereof. In another embodiment, "treatment" or "treating" refers to an amelioration of at least one measurable physical parameter associated with disease or disorder not necessarily discernible by the subject. In yet another embodiment, "treatment" or "treating" refers to inhibiting the progression of a disease or disorder either physically, e.g., stabilization of a discernible symptom, physiologically, e.g., stabilization of a physical parameter, or both.

In certain embodiments, the methods and compositions of the present invention are useful as a preventative measure against disease or disorder. As used herein, "prevention" or "preventing" refers to risk reduction in acquiring a given disease or disorder.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include, but are not limited to, fatigue, dry mouth, and loss of appetite. Side effects from biological therapies/immunotherapies include, but are not limited to, rashes or swellings at the site of administration, flu-like symptoms such as fever, chills and fatigue, digestive tract problems and allergic reactions. Side effects from hormonal therapies include, but are not limited to, nausea, fertility problems, depression, loss of appetite, eye problems, headache, and weight fluctuation. Additional undesired effects typically experienced by patients are numerous and known in the art. Many are described in the *Physicians' Desk Reference* (59th ed., 2005).

As used herein, the terms "subject" and "patient" are used interchangeably to refer to an animal (e.g., a mammal). In a specific embodiment, a subject is a mammal (e.g., a non-human mammal and a human). In another embodiment, a subject is a pet (e.g., a dog, a cat, a guinea pig, a monkey and a bird), a farm animal (e.g., a horse, a cow, a pig, a goat and a chicken) or a laboratory animal (e.g., a mouse and a rat). In another embodiment, a subject is a primate (e.g., a chimpanzee and a human). In an embodiment, a subject is a human.

5. DETAILED DESCRIPTION OF THE INVENTION

The present invention relates, in part, to modified PAI-1 molecules, nucleic acid molecules encoding the modified PAI-1 molecules, as well as therapeutic and prophylactic methods using the modified PAI-1 molecules of the invention. These modified PAI-1 molecules display a decrease in one or more functional activities as compared to wild-type PAI-1 protein. The modified PAI-1 molecule may comprise one or more mutations that decrease one or more functional activities to one or more molecules such as uPA, tPA or Vn. Such modified PAI-1 molecules retain at least one functional activity of wild-type PAI-1 protein.

5.1 MODIFIED PAI-1 MOLECULES

In one aspect, the present invention is directed to modified PAI-1 molecules that have new and useful properties. In one aspect, the modified PAI-1 molecules have increased half-life of the active form, but are deficient in one or more functional activities as compared to a wild-type PAI-1 protein. For example, the modified PAI-1 molecules of the present invention can exhibit at least one of the following functional activities: (i) decreased binding activity against at least one of the following molecules: uPA, tPA and Vn; and (ii) decreased specific activity against at least one of the following molecules: uPA, tPA and Vn. These functional activities are determined, e.g., by the method described in Section 5.6 infra, and are also known by one skilled in the art.

The modified PAI-1 molecule which are deficient in one or more functional activities comprises one or more mutations. The one or more mutations can occur, for example, at amino acid positions 1-28, 29-32, 33-50, 51-70, 71-80, 81-91, 92-107, 108-120, 121-130, 131-140, 141-150, 151-160, 161-170, 171-179, 180-197, 198-210, 211-220, 221-230, 231-240, 241-243, 246-249, 250-260, 261-270, 271-280, 281-

290, 291-300, 301-310, 311-320, 321-330, 331-340, 341-353, 353-374, 375-380, 381-391, or 392-402 of the amino acid sequence of a wild-type PAI-1 protein using SEQ ID NO:2 for numbering. In particular, such mutations can decrease one or more of the activities of the modified PAI-1 molecule. The decreased activities include, but are not limited to, binding and specific activities. In specific embodiments, the modified PAI-1 molecule has one or more reduced activities, such as decreased serpin activity, decreased binding activity to at least one of the following molecules: uPA, tPA, and Vn; and decreased specific activity against at least one of the following molecules: uPA, tPA and Vn. The modified PAI-1 molecule retains at least one activity of the wild-type PAI-1 protein.

In specific embodiments, the modified PAI-1 has decreased binding activity or decreased specific activity against vitronectin. In certain embodiments, the modified PAI-1 has one or more mutation at the α-helices C and E to β-strand IA. In certain embodiments, one or more mutations occur at amino acid at positions 32, 36, 78, 132, 133, 139, 146, 167, 170, 173, 354, 366, 369 and 373 of the amino acid sequence of a wild-type PAI-1 protein using SEQ ID NO:2 for numbering. In certain embodiments, the one or more mutations do not occur at amino acid at positions 36-170, 32, 36, 78, 132, 133, 139, 146, 167, 170, 173, 354, 366, 369 and 373. In specific embodiments, one or more amino acid substitutions occur as follows: Gln 79 Pro, Phe 132 Ser, Met 133 Thr, Gln 146 Lys, and Thr 167 Ala. In other embodiments, one or more amino acid substitutions are not Gln 78 Pro, Phe 132 Ser, Met 133 Thr, Gln 146 Lys, and Thr 167 Ala. The number of amino acid residues that may be substituted or inserted in a modified PAI-1 are 1, 2, 3, 4, 5, 6, 7, 8, 9, 10, 1-5, 5-10, 10-15, 15-20, 20-25, 25-30, 30-35, 35-40, 40-45, or 45-50.

In other embodiments, the modified PAI-1 molecules retain 10%-20%, 20%-30%, 30%-40%, 40%-50%, 50%-60%, 60%-70%, 70%-80%, 80%-90%, 90%-100% of at least one functional activity compared to a wild-type PAI-1 protein.

In one embodiment, the modified PAI-1 molecules have one or more decreased functional activity as compared to wild-type PAI-1, for example, but not limited to, binding to or specific activity against uPA, tPA and Vn. In certain embodiments, the modified PAI-1 molecules have 1.5, 2, 3, 10, or 20 times reduction of at least one activity as compared to the wild-type PAI-1. In certain embodiments, the modified PAI-1 molecule retains at least one activity of a wild-type PAI-1 protein.

In certain embodiments, the modified PAI-1 molecule exhibits an increased half-life of the active form and has decreased serpin activity against uPA. In specific embodiments, the modified PAI-1 molecule comprises a mutation at amino acid position 369 of SEQ ID NO:2. In certain embodiments, Arg369 is substituted by Ala, Gly or Ser.

In certain embodiments, the modified PAI-1 molecule exhibits an increased half-life of the active form and has a decreased serpin activity against tPA. In specific embodiments, the modified PAI-1 molecule comprises a mutation at amino acid position 369 of SEQ ID NO:2. In certain embodiments, Arg369 is substituted by Ala, Gly or Ser.

In certain embodiments, the modified PAI-1 molecule exhibits an increased half-life of the active form and has a decreased serpin activity against uPA and tPA. In specific embodiments, the modified PAI-1 molecule comprises a mutation at amino acid position 369 of SEQ ID NO:2. In certain embodiments, Arg369 is substituted by Ala, Gly or Ser. In an embodiment, the modified PAI-1 molecule is VLHL$_{NS}$ PAI-1.

In certain embodiments, the modified PAI-1 molecule exhibits an increased half-life of the active form and has a decreased binding to uPA. In specific embodiments, the modified PAI-1 molecule comprises a mutation at amino acid position 369 of SEQ ID NO:2. In certain embodiments, Arg369 is substituted by Ala, Gly or Ser.

In certain embodiments, the modified PAI-1 molecule exhibits an increased half-life of the active form and has a decreased binding to tPA. In specific embodiments, the modified PAI-1 molecule comprises a mutation at amino acid position 352 or 369 of SEQ ID NO:2. In certain embodiments, Asn352 is substituted by Ala or Pro; Arg369 is substituted by Ala, Gly or Ser. In one particular embodiment, Asn352 is substituted by Pro and Arg369 is substituted by Ala. In another particular embodiment, the modified PAI-1 molecule is VLHL$_{NT}$ PAI-1 (SEQ ID NO:12).

In certain embodiments, the modified PAI-1 molecule exhibits an increased half-life of the active form and has a decreased binding to Vn. In specific embodiments, the modified PAI-1 molecule comprises a mutation at amino acid position 146 of SEQ ID NO:2. In certain embodiments, Gln146 is substituted by Asn or Lys. In a particular embodiment, the modified PAI-1 molecule is VLHL$_{NV}$ PAI-1 (SEQ ID NO:13).

In certain embodiments, the modified PAI-1 molecule exhibits an increased half-life of the active form and comprises a plurality of mutations such that the modified PAI-1 molecule exhibits decreased serpin activity against uPA and tPA, and decreased binding to Vn. In specific embodiments, the modified PAI-1 molecule comprises mutations at amino acid positions 369 and 146 of SEQ ID NO:2. In certain embodiments, Arg369 is substituted by Ala, Gly or Ser and Gln146 is substituted by Lys or Asn. In a particular embodiment, Arg369 is substituted by Ala and Gln146 is substituted by Lys. In another particular embodiment, the modified PAI-1 molecule is VLHL$_{NS, NV}$ PAI-1 (SEQ ID NO:14).

In certain embodiments, the modified PAI-1 molecule exhibits an increased half-life of the active form and comprises a plurality of mutations that decrease the serpin activity against uPA and tPA, as well as decrease binding to tPA. In specific embodiments, the modified PAI-1 molecule comprises mutations at amino acid positions 369 and 352 of SEQ ID NO:2. In certain embodiments, Arg369 is substituted by Ala, Gly or Ser and Asn352 is substituted by Lys or Ala. In certain embodiments, Arg369 is substituted by Ala and Asn352 is substituted by Pro. In an embodiment, the modified PAI-1 molecule is VLHL$_{NS, NT}$ PAI-1 (SEQ ID NO:15).

In certain embodiments, the modified PAI-1 molecule exhibits an increased half-life of the active form and has a decreased binding to Vn and tPA. In specific embodiments, the modified PAI-1 molecule comprises multiple mutations at amino acid positions 146 and 352 of SEQ ID NO:2. In certain embodiments, Gln146 is substituted by Asn or Lys, Asn352 is substituted by Ala or Pro. In certain embodiments, Gln146 is substituted by Lys, Asn352 is substituted by Pro. In an embodiment, the modified PAI-1 molecule is VLHL$_{NV, NT}$ PAI-1 (SEQ ID NO:16).

In certain embodiments, the modified PAI-1 molecule exhibits an increased half-life of the active form and has a decreased binding to Vn and tPA and decreased serpin activity. In specific embodiments, the modified PAI-1 molecule comprises multiple mutations at amino acid positions 146, 352 and 369 of SEQ ID NO:2. In certain embodiments, Gln146 is substituted by Asn or Lys, Asn352 is substituted by Ala or Pro, Arg369 is substituted by Ala, Gly or Ser. In certain embodiments, Gln146 is substituted by Lys, Asn352 is substituted by Pro, and Arg369 is substituted by Ala. In an embodiment, the modified PAI-1 molecule is VLHL$_{NS, NV, NT}$ PAI-1 (SEQ ID NO:17). In certain embodiments, the modified PAI-1 molecule exhibits increased half-life of the active form and has decreased binding to Vn. In specific embodiments, the modified PAI-1 molecule comprises a deletion at 127-181 of the amino acid sequence of a wild-type PAI-1 protein using SEQ ID NO:2 for numbering. In a specific embodiment, the modified PAI-1 molecule is mini-VLHL (SEQ ID NO:7).

In specific embodiments, the modified PAI-1 molecule comprises the amino acid sequence of SEQ ID NOS:10 and 11.

In certain embodiments, the modified PAI-1 molecule exhibits an increased half-life of the active form, a decreased activity to uPA and an increased activity to tPA. In specific embodiments, the modified PAI-1 molecule 369Arg is replaced by Tyr. In specific embodiments, the modified PAI-1 molecule 367Ser is replaced by Tyr. In specific embodiments, 368Ala is unchanged.

In certain embodiments, the modified PAI-1 molecule exhibits an increased half-life of the active form, a decreased activity to tPA and an increased activity to uPA. In specific embodiments, the modified PAI-1 molecule 364Val is replaced by Pro. In specific embodiments, the modified PAI-1 molecule 372Pro is replaced by Leu. In specific embodiments, the modified PAI-1 molecule 373Glu is replaced by Ser. In specific embodiments, the modified PAI-1 molecule 374Glu is replaced by Ser. In specific embodiments, 371Ala is unchanged.

In certain embodiments, the modified PAI-1 molecule exhibits an increased half-life of the active form, a decreased activity to Vn and an increased activity to tPA. In specific embodiments, the modified PAI-1 molecule 369Arg is replaced by Tyr. In specific embodiments, the modified PAI-1 molecule 367Ser is replaced by Tyr. In specific embodiments, 368Ala is unchanged.

In certain embodiments, the modified PAI-1 molecule exhibits an increased half-life of the active form, a decreased activity to Vn and an increased activity to uPA. In specific embodiments, the modified PAI-1 molecule 364Val is replaced by Pro. In specific embodiments, the modified PAI-1 molecule 372Pro is replaced by Leu. In specific embodiments, the modified PAI-1 molecule 373Glu is replaced by Ser. In specific embodiments, the modified PAI-1 molecule 374Glu is replaced by Ser. In specific embodiments, 371Ala is unchanged.

Methods of making the foregoing by, for example, chemical synthesis or recombinant DNA technology are within the scope of the invention and skill in the art.

Modified PAI-1 molecules that exhibit an increased half-life of the active form may comprise one or more intramolecular bonds. Such modified PAI-1 molecules that exhibit an increased half-life are disclosed in the art, for example, in international Publication number WO 03/080646A2, which is incorporated by reference in its entirety. These intramolecular bonds may include, for example, non-covalent bond, covalent bond, disulfide bond, salt bridge, hydrogen bond, and pi-pi interaction.

In certain embodiments, an intramolecular bond may be introduced using chemical cross-linking methods. Methods of chemical cross-linking include, for example, using an amine-sulfhydryl cross-linker such as N-(α-maleimidoacetoxy)-succinimide eser ("AMAS") or N-(κ-maleimidoundecanoyloxy)-sulfosuccinimide ester ("KMUS") (Pierce Chemical Co.). Such methods would generally involve reductive methylation of one protein to block N-termini, cross-linking of blocked peptide at pH 6.5-7.5 using suflo-KMUS or AMAS, and reacting with the succinimide group of the modified protein with the other protein at pH 8-9. Other methods which are well known in the art may be used to form intramolecular covalent bonds at particular amino acid residues as described herein to provide modified PAI-1 that are useful in the present invention.

Desired mutations may be introduced by any method known in the art, for example, by PCR using appropriate primers. Modification of the PAI-1 protein may be produced by site-directed mutagenesis to substitute the codon for an amino acid with the codon for cysteine in a nucleic acid sequence encoding PAI-1. In one aspect, the invention provides modified PAI-1 molecules in which two or more amino acid residues that do not contain a sulfhydryl group have been replaced with amino acid residues that contain sulfhydryl groups such that one or more intrachain disulfide bonds form within the modified PAI-1 molecule, which modified PAI-1 molecules exhibit a much longer in vivo half-life of the active form than a wild type PAI-1 protein. In certain embodiments, two, four, or six amino acid substitutions that introduce sulfhydryl groups and promote the formation of one, two or three intramolecular disulfide bridges. In other embodiments, modification of the PAI-1 protein may be produced by insertion of amino acid residues containing a sulfhydryl group such that formation of one, two or three intramolecular disulfide bridges are formed. In a specific embodiment, one or more disulfide bridges may be formed to bridge the top and bottom parts of the A3 strand and the A5 strand, within the helix D region.

The disulfide bonds introduced into PAI-1 preferably hold the A3 strand and A5 strand of the β-sheet together so as to prevent the insertion of the A4 strand between the A3 strand and A5 strand of the β-sheet. In certain embodiments, the intra-molecular bond links the A3 strand and the A5 strand of the β-sheet of the PAI-1 protein.

In particular, by restraining the movement of the A3 strand an the A5 strand, as well as limiting the flexibility of the helix D region, as defined supra, it is possible to prevent insertion of the reactive loop between A3 strand and A5 strand. Such a modification extends the half-life of PAI-1 protein. Based on the known structure of active PAI-1, amino acid residues within the amino acid sequence of PAI-1 have been identified that can be substituted with cysteine residues to produce disulfide bridges linking the top and bottom parts of the A3 strand and the A5 strand as well as sites within the helix D region. Desired mutations may be introduced by any method known in the art, for example, by PCR using appropriate primers. Modification of the PAI-1 protein may be produced by site-directed mutagenesis to substitute the codon for an amino acid with the codon for cysteine in a nucleic acid sequence encoding PAI-1. In a preferred embodiment, two, four or six amino acid substitutions may be introduced, thus promoting the formation of one, 2 or 3 disulfide bridges. In a specific embodiment, one or more disulfide bridges may be formed to bridge the top and bottom parts of the A3 strand and the A5 strand, within the helix D region.

To increase the half-life of the modified plasminogen activator inhibitor type-1 (PAI-1) polypeptides of the present invention, amino acid residues that do not contain a sulfhydryl group can be substituted with amino acid residues that contain a sulfhydryl group, such as cysteine residues, such that one or more intramolecular disulfide bonds are formed, having a longer in vivo half-life of the active form of modified PAI-1 than a PAI-1 protein which has no cysteine residues or disulfide bonds (or other chemical cross-linking).

The helix D loop comprises amino acids at positions 92-107 of SEQ ID NO:2. The A3 strand comprises amino acids at positions 341-353 of SEQ ID NO:2. The A4 strand comprises amino acids at positions 356-374 of SEQ ID NO:2. The A5 strand comprises amino acid at positions 180-197 of SEQ ID NO:2. The modified PAI-1 molecule can comprise modifications relative to wild type PAI-1 that increase in vivo half-life of the active form of the modified PAI-1 molecule. Such modification can include, but not limited to, ones that promote formation of disulfide bridges between the A3 strand and the A5 strand of the β-sheet. The disulfide bridges may be formed, for example, by introducing two, four, or six cysteines located near or within the β-sheet. In certain embodiments, the amino acid residues to be substituted with sulfhydryl-containing groups are amino acids having aliphatic side chains such as, but not limited to, glycine, alanine, valine, leucine, isoleucine. In other embodiments, the amino acid residues to be substituted with sulfhydryl-containing groups are amino acids having amide side chains such as, but not limited to, asparagine or glutamine.

In certain embodiments, mutations are introduced such that disulfide bonds are formed so that the A3 strand and A5 strand of the β-sheet are held close together. In certain embodiments, the distance between the A3 strand and A5 strand of the β-sheet are less than 0.5 Å, more than 0.5 Å and not more than 2 Å, more than 2 Å and not more than 4 Å, more than 4 Å and not more than 10 Å, more than 10 Å and not more than 20 Å, more than 20 Å and not more than 40 Å as determined by x-ray crystallography, NMR, or molecular modelling. In certain embodiments, one or more disulfide bridges are formed at or near helix D (amino acid positions 31 and 97), β-sheet t (amino acid positions 197 and 355), or β-sheet b (amino acid positions 192 and 347). In certain embodiments, one or more disulfide bridges are formed at or near β-sheet b and β-sheet t. In certain embodiments, a disulfide bridge is formed at or near β-sheet t. In certain embodiments, one or more disulfide bridges are formed between amino acid positions 31 and 97, 192 and 347, or 197 and 355 of the amino acid sequence of a wild-type PAI-1 protein using SEQ ID NO:2 for numbering.

In certain embodiments, modified PAI-1 molecules of the present invention have an increased half-life when the amino acid residues in the reactive center loop are deleted to reduced the overall length of the reactive center loop. In certain embodiments, one, two, three, four, five, six, or seven residues in P10-P6, i.e., residues connecting 359Ser to 365Ile are deleted. In certain embodiments, 360Ser, 361Thr, 363Ala, and/or 364Val are deleted. In certain embodiments, one, two, three, or four residues in P9-P6, i.e., residues connecting 360Ser to 365Ile are deleted. In certain embodiments, one, two, three, or four residues in P10-P7, i.e., residues connecting 359Ser to 364Val are deleted.

In other embodiments, if an amino acid residue containing a sulfhydryl group is inserted or substituted at amino acid position 28, 29, 30, 31, 32, 33, or 34 of a wild-type PAI-1 protein using SEQ ID NO:2 for numbering, another amino acid residue containing a sulfhydryl group is inserted or substituted at amino acid position 94, 95, 96, 97, 98, 99, or 100 using SEQ ID NO:2 for numbering. If an amino acid residue containing a sulfhydryl group is inserted or substituted at amino acid position 189, 190, 191, 192, 193, 194, 195, 196, 197, or 198 of a wild-type PAI-1 protein using SEQ ID NO:2 for numbering, another amino acid residue containing a sulfhydryl group is inserted or substituted at amino acid position 344, 345, 346, 347, 348, 349, 350, 351, 352, 353, 354, 355 or 356 using SEQ ID NO:2 for numbering. If an amino acid residue containing a sulfhydryl group is inserted or substituted at amino acid position 192, 193, 194, 195, 196, 197, 198, 199, or 200 of a wild-type PAI-1 protein using SEQ ID NO:2 for numbering, another amino acid residue containing a sulfhydryl group is inserted or substituted at amino acid position 352, 353, 354, 355, 356, 357, or 358 using SEQ ID NO:2 for numbering.

In other embodiments, if an His residue is inserted or substituted at amino acid position 28, 29, 30, 31, 32, 33 or 34 of a wild-type PAI-1 protein using SEQ ID NO:2 for numbering, an Asp or Glu residue is inserted or substituted at amino acid position 94, 95, 96, 97, 98, 99 or 100 using SEQ ID NO:2 for numbering. In such embodiments, an intramolecular salt bridge may be formed.

In other embodiments, if an Asp or Glu residue is inserted or substituted at amino acid position 28, 29, 30, 31, 32, 33 or 34 of a wild-type PAI-1 protein using SEQ ID NO:2 for numbering, an His residue is inserted or substituted at amino acid position 94, 95, 96, 97, 98, 99 or 100 using SEQ ID NO:2 for numbering. In such embodiments, an intramolecular salt bridge may be formed.

In other embodiments, if a His residue is inserted or substituted at amino acid position 189, 190, 191, 192, 193, 194 or 195 of a wild-type PAI-1 protein using SEQ ID NO:2 for numbering, an Asp or Glu residue is inserted or substituted at amino acid position 344, 345, 346, 347, 348, 349 or 350 using SEQ ID NO:2 for numbering. In such embodiments, an intramolecular salt bridge may be formed.

In other embodiments, if an Asp or Glu residue is inserted or substituted at amino acid position 189, 190, 191, 192, 193, 194 or 195 of a wild-type PAI-1 protein using SEQ ID NO:2 for numbering, a His residue is inserted or substituted at amino acid position 344, 345, 346, 347, 348, 349 or 350 using SEQ ID NO:2 for numbering. In such embodiments, an intramolecular salt bridge may be formed.

In other embodiments, if a His residue is inserted or substituted at amino acid position 194, 195, 196, 197, 198, 199 or 200 of a wild-type PAI-1 protein using SEQ ID NO:2 for numbering, an Asp or Glu residue is inserted or substituted at amino acid position 352, 353, 354, 355, 356, 357 or 358 using SEQ ID NO:2 for numbering. In such embodiments, an intramolecular salt bridge may be formed.

In other embodiments, if an Asp or Glu residue is inserted or substituted at amino acid position 194, 195, 196, 197, 198, 199 or 200 of a wild-type PAI-1 protein using SEQ ID NO:2 for numbering, a His residue is inserted or substituted at amino acid position 352, 353, 354, 355, 356, 357 or 358 using SEQ ID NO:2 for numbering. In such embodiments, an intramolecular salt bridge may be formed.

In other embodiments, if a Ser, Thr, Phe, Tyr or Glu residue is inserted or substituted at amino acid position 28, 29, 30, 31, 32, 33 or 34 of a wild-type PAI-1 protein using SEQ ID NO:2 for numbering, a Ser, Thr, Phe, Tyr or Glu residue is inserted or substituted at amino acid position 94, 95, 96, 97, 98, 99 or 100 using SEQ ID NO:2 for numbering. In such embodiments, an intramolecular hydrogen bond or pi-pi interaction may be formed.

In other embodiments, if a Ser, Thr, Phe, Tyr or Glu residue is inserted or substituted at amino acid position 189, 190, 191, 192, 193, 194 or 195 of a wild-type PAI-1 protein using SEQ ID NO:2 for numbering, a Ser, Thr, Phe, Tyr or Glu residue is inserted or substituted at amino acid position 94, 95, 96, 97, 98, 99 or 100 using SEQ ID NO:2 for numbering. In such embodiments, an intramolecular hydrogen bond may be formed.

In other embodiments, if a Ser, Thr, Phe, Tyr or Glu residue is inserted or substituted at amino acid position 194, 195, 196, 197, 198, 199 or 200 of a wild-type PAI-1 protein using SEQ ID NO:2 for numbering, a Ser, Thr, Tyr or Glu residue is inserted or substituted at amino acid position 352, 353, 354, 355, 356, 357 or 358 using SEQ ID NO:2 for numbering. In such embodiments, an intramolecular hydrogen bond or pi-pi interaction may be formed.

A modified PAI-1 molecule may, for example, include one or more amino acid mutations at amino acid positions 354 to 366 and 367 to 373 of the amino acid sequence of a wild-type PAI-1 protein, using SEQ ID NO:2 for numbering, to make it more stable. A modified PAI-1 molecule may, for example, include or further include one or more amino acid substitutions in SEQ ID NO:2 which stabilize the protein, including, for example: (a) His at position 173; (b) Thr at position 177; (c) Leu at position 342; (d) Ile at position 377; (e) Leu at position 303; (f) Arg at position 53; (g) Leu at position 114; (h) Ile at position 395; (i) Arg at position 356; (j) Arg at position 358; (k) Gly at position 354. PAI-1 including any combination of the foregoing substitutions may be used as a stabilized form of the protein, in particular for use in vivo. In certain embodiments, a modified PAI-1 molecule comprises two, three, four, five, or six, seven, eight, nine, ten, eleven or all eleven of these substitutions.

In certain embodiments, the modified PAI-1 molecule can comprise any one or more of such substitutions and can further comprise sulfhydryl-containing mutations that promote intramolecular disulfide bonds.

In specific embodiments, the modified PAI-1 molecule does not have one or more amino acid mutations at amino acid positions 354 to 366 and 367 to 373 of the amino acid sequence of a wild-type PAI-1 protein using SEQ ID NO:2 for numbering. In specific embodiments, the modified PAI-1 molecule does not have an amino acid substitution at position 173 and in another embodiment, the amino acid at position 173 is not substituted with His residue; the amino acid at position 177 is not substituted with Thr; the amino acid at position 342 is not substituted with Leu; the amino acid at position 377 is not substituted with Ile residue; the amino acid at position 114 is not substituted with Leu; the amino acid at position 395 is not substituted with Ile residue; the amino acid substitution at 356 and/or 358 are not substituted with Arg residue; the amino acid substitution at 354 is not Gly; the amino acid substitution at position 303 is not Ile; the amino acid substitution at position 53 is not Thr or Gln. In a specific embodiment, the modified PAI-1 molecule is not resistant to cleavage by proteinases including, elastase, uPA, plasmin, thrombin, cathepsin G, chymase, elastinase A, elastinase B, stromelysin and collagenase. In another specific embodiment, the modified PAI-1 molecule is resistant to cleavage by proteinases including, elastase, uPA, plasmin, thrombin, cathepsin G, chymase, elastinase A, elastinase B, stromelysin and collagenase.

In one aspect of the present invention relates to modified PAI-1 molecules in which the active form of the modified PAI-1 molecules exhibit an increased in vivo half-life. In certain embodiments, the in vivo half-life is over 3 hours, 6 hours, 10 hours, 20 hours, 50 hours, 60 hours, 70 hours, 90 hours, 100 hours, 150 hours, 200 hours, 300 hours, 400 hours, 500 hours, 600 hours, 700 hours, 800 hours, 900 hours, 10 days, 12 days, 16 days, 30 days, or 60 days. In a particular embodiment, the active form of PAI-1 molecule exhibit an in vivo half-life of over 2 weeks, 4 weeks, or 2 months. In specific embodiments, the in vivo half-life is 3-6 hrs, 6-10 hours, 10-20 hours, 20-50 hours, 50-60 hours, 60-70 hours, 70-90 hours, 90-100 hours, 100-150 hours, 150-200 hours, 200-300 hours, 300-400 hours, 400-500 hours, 500-600 hours, 600-700 hours, 700-800 hours, 800-900 hours, 10-12 days, 12-16 days, 16-30 days, 30-16 days or over 60 days.

In certain embodiments, the present invention also provides a modified PAI-1 molecule having at least three mutations, for example, at least three amino acid substitutions, wherein two of the mutations are amino acid substitutions in which an amino acid without a sulfhydryl group is substituted with an amino acid with a sulfhydryl group, and wherein the additional mutation or mutations may include an amino acid substitution with or without a sulfhydryl group. In an embodiment, the amino acid substitutions with an amino acid residue with a sulfhydryl group are in pairs of amino acid substitutions. In particular, if an amino acid at positions 10-40 is substituted, another amino acid at positions 70-120 is substituted; if an amino acid at positions 150-220 is substituted, another amino acid at positions 300-400 is substituted. In other embodiments, the two or more amino acid substitutions, in certain embodiments, in pairs of amino acids at amino acid positions 31 and 97, 192 and 347, or 197 and 355 of the human PAI-1. In other embodiments, one or more pairs of amino acid residues selected from the pairs Valine 31 and Alanine 97, or Leucine 192 and Valine 347, or Glutamine 197 and Glycine 355 are both replaced with cysteine residues. In an embodiment, one pair of amino acid residue substitution is at Glutamine 197 and Glycine 355.

Modified molecules, fusion proteins, and nucleic acid molecules encoding such molecules, and production of the foregoing molecules, e.g., by recombinant DNA methods, are also provided.

In specific embodiments, the invention provides fragments of modified PAI-1 molecules consisting of at least 6 amino acids, 10 amino acids, 50 amino acids, 75 amino acids, 100 amino acids, 150 amino acids, 200 amino acids, 250 amino acids, 300 amino acids, or 349 amino acids. In specific embodiments, the fragments of modified PAI-1 consist of at most 50 amino acids, 75 amino acids, 100 amino acids, 150 amino acids, 300 amino acids, 250 amino acids, 300 amino acids, or 349 amino acids. In certain embodiments, the modified PAI-1 molecule does not contain helix E, F and/or G. In specific embodiments, the modified PAI-1 lacks amino acid residues at positions 127-181 of SEQ ID NO:2. In various embodiments, the modified PAI-1 comprises or consists essentially of a mutated helix D, β-sheet b, β-sheet t or combinations thereof. In an embodiment, the modified PAI-1 molecule is mini-VLHL (See FIG. 1) (SEQ ID NO:7). In an embodiment, the modified PAI-1 molecule does not bind Vn.

5.2 NUCLEIC ACID MOLECULES ENCODING MODIFIED PAI-1

The present invention also relates to nucleic acid molecules comprising sequences encoding modified PAI-1 molecules of the invention.

Due to the degeneracy of nucleotide coding sequences, any DNA sequence that encodes the same amino acid sequence for a modified PAI-1 molecule may be used in the practice of the present invention. In certain embodiments, the nucleotide coding sequence utilizes codons that are preferentially used by the species in which the nucleotide sequence is to be recombinantly expressed.

The modified PAI-1 nucleic acid molecules of the invention can be made, for example, by recombinant or synthetic methods known in the art. Such molecules can also routinely be used to express modified PAI-1 molecules of the invention.

5.3 THERAPEUTIC AND PROPHYLACTIC METHODS

The present invention is based, in part, on the surprising discovery that the modified PAI-1 molecules of the present invention can reduce cancer cell growth. In specific embodiments, modified PAI-1 molecules of the invention can be used to treat, prevent and ameliorate a symptom of cancer. For example, modified PAI-1 molecules that exhibit an extended in vivo half-life and a decreased binding to and/or specific activity against uPA, tPA or both can be used as part of methods for treating or ameliorating a symptom of cancer. In certain embodiments, the PAI-1 molecule is $VLHL_{NS}$ or $VLHL_{NS,NV}$.

In one embodiment, modified PAI-1 molecule that exhibit decreased activity to Vn can be used to inhibit metastasis. In certain embodiments, the modified PAI-1 molecule can inhibit angiogenesis, an effect which can be harnessed to inhibit both local and metastatic tumor growth. Thus, the methods of the present invention may be used for the treatment of diseases and disorders related to angiogenesis or inhibition of other functions mediated or influenced by PAI-1, uPA, tPA, Vn including, but not limited to, cell proliferation, primary and metastatic neoplastic diseases, e.g. cancer, cell migration and/or cell motility. In certain embodiments, the modified PAI-1 molecules that are useful for inhibiting angiogenesis and/or reducing metastasis exhibit an increased in vivo half-life and can exhibit a decreased binding to and/or specific activity against Vn. In an embodiment, the PAI-1 molecule is $VLHL_{NV}$. Accordingly, the invention provides methods of treating, preventing, managing or ameliorating cancer, particularly metastatic cancer by administration of modified PAI-1 molecules of the invention.

The therapeutics can be utilized for the prevention of a variety of cancers, e.g., in individuals who are predisposed as a result of familial history or in individuals with an enhanced risk to cancer due to environmental factors.

The methods and compositions of the invention are useful not only in untreated patients but are also useful in the treatment of patients partially or completely unresponsive to other treatments. In various embodiments, the invention provides methods and compositions useful for the treatment of diseases or disorders in patients that have been shown to be or may be refractory or non-responsive to therapies comprising the administration of other agents.

In certain embodiments, the methods and compositions of the invention are used for the treatment and/or prevention of brain-tumor, glioma, ovarian, breast, colon, lung, pancreatic, uterine, prostate cancers or melanoma.

The modified PAI-1 molecules of the invention can be administered to treat premalignant conditions and to prevent progression to a neoplastic or malignant state. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 197, Basic Pathology, 2d Ed., W.B. Saunders Co., Philadelphia, pp. 8 79.)

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of the modified PAI-1 molecules.

In another specific embodiment, the modified PAI-1 molecules of the invention is administered to a human patient to prevent progression to ovarian, breast, colon, lung, pancreatic, prostate, uterine cancer or melanoma.

The invention encompasses methods for treating or preventing a cancer or metastasis in a subject comprising in any order the steps of administering to the subject a modified PAI-1 molecule. In certain embodiments, the compositions and methods of the invention can be used to prevent, inhibit or reduce the growth or metastasis of cancerous cells. In a specific embodiment, the administration of a modified PAI-1 molecule inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of the administration of said modified PAI-1 molecule.

Encompassed by the invention are combination therapies that have additive potency or an additive therapeutic effect while reducing or avoiding unwanted or adverse effects. The invention also encompasses synergistic combinations where the therapeutic efficacy is greater than the additive, while unwanted or adverse effects are reduced or avoided.

Other cancer treatment that may be used in combination of the administration of the modified PAI-1 molecules of the present invention include, for example, the use of one or more molecules, or compounds for the treatment of cancer (i.e., cancer therapeutics), which molecules, compounds or treatments include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, in certain embodiments, the methods of the present invention increase patient compliance, improve therapy and/or reduce unwanted or adverse effects.

In a specific embodiment, the methods of the invention encompass the administration of one or more angiogenesis inhibitors such as, but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combrestatin; A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate;

cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin I1, or rIL2), interferon alfa 2a; interferon alfa 2b; interferon alfa n1; interferon alfa n3; interferon beta I a; interferon gamma I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti cancer drugs include, but are not limited to: 20 epi 1,25 dihydroxyvitamin D3; 5 ethynyluracil; abiraterone; aclarubicin; acylfulvene; adecypenol; adozelesin; aldesleukin; ALL TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL 2; capecitabine; carboxamide amino triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum triamine complex; porfimer sodium; porfiromycin; prednisone; propyl bis-acridone; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In certain embodiments, additional anti-cancer drugs are 5-fluorouracil and leucovorin. These two agents are particularly useful when used in methods employing thalidomide and a topoisomerase inhibitor.

In one embodiment, one or more chemoagents are administered together or conjugated together with the modified PAI-1 molecules of the invention to treat a cancer patient. A chemoagent (or "anti-cancer agent" or "anti-tumor agent" or "cancer therapeutic") refers to any molecule or compound that assists in the treatment of tumors or cancer. Examples of chemoagents include, but are not limited to: cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2 chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, *Bacillus Calmette Guerin*, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplatin, chlorabusil, cladribine, cylarabine, daclinomycin, estramusine, floxuride, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof.

In other embodiments, the method for the treatment of cancers further comprises administration of pharmaceutical compositions comprising 5-fluorouracil, cisplatin, docetaxel, doxorubicin, Herceptin®, gemcitabine (Seidman, 2001, Oncology 15:11 14), IL-2, paclitaxel, and/or VP-16 (etoposide). In another embodiment, pharmaceutical compositions comprises modified PAI-1 molecules of the present invention conjugated with the above agents.

In another embodiment, the treatment of the present invention further includes the administration of one or more immunotherapeutic agents, such as antibodies and immunomodulators, which include, but are not limited to: HERCEPTIN®, RITUXAN®, OVAREX™, PANOREX®, BEC2, IMC-C225, VITAXIN™, CAMPATH® I/H, Smart MI95, LYMPHOCIDE™, Smart I D10, and ONCOLYM™, rituximab, gemtuzumab, or trastuzumab.

In another embodiment, the treatment of the present invention further includes administering one or more anti-angiogenic agents, which include, but are not limited to: angiostatin, thalidomide, kringle 5, endostatin, other Serpins, antithrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, *Cancer Res.* 51:2077), a 14-amino acid peptide corresponding to a fragment of collagen I (Tolma et al., 1993, J. Cell Biol. 122:497), a 19 amino acid peptide corresponding to a fragment of Thrombospondin 1 (Tolsma et al., 1993, *J. Cell Biol.* 122: 497), a 20-amino acid peptide corresponding to a fragment of SPARC (Sage et al., 1995, *J. Cell. Biochem.* 57:1329-), or any fragments, family members, or derivatives thereof, including pharmaceutically acceptable salts thereof.

Other peptides that inhibit angiogenesis and correspond to fragments of laminin, fibronectin, procollagen, and EGF have also been described (see the review by Cao, 1998, *Prog. Mol. Subcell. Biol.* 20:161). Monoclonal antibodies and cyclic pentapeptides, which block certain integrins that bind RGD proteins (i.e., possess the peptide motif Arg-Gly-Asp), for example, endostatin, have been demonstrated to have anti-vascularization activities (Brooks et al., 1994, *Science* 264: 569; Hammes et al., 1996, *Nature Medicine* 2:529). Moreover, inhibition of the urokinase plasminogen activator receptor by receptor antagonists inhibits angiogenesis, tumor growth and metastasis (Min et al., 1996, *Cancer Res.*

56:2428-33; Crowley et al., 1993, *Proc Natl Acad Sci. USA* 90:5021). Use of such anti-angiogenic agents are also utilized by the present invention.

In another embodiment, the treatment method further comprises the use of radiation.

In another embodiment, the treatment method further comprises the administration of one or more cytokines, which includes, but is not limited to: lymphokines, tumor necrosis factors, tumor necrosis factor-like cytokines, lymphotoxin-a, lymphotoxin-b, interferon-a, interferon-b, macrophage inflammatory proteins, granulocyte monocyte colony stimulating factor, interleukins (including, but not limited to: interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In yet another embodiment, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

The modified PAI-1 molecules of the invention which exhibit an increased in vivo half-life and exhibit reduced ability to bind to and/or the specific activity against tPA may also be used to treat cardio-vascular diseases such as, but not limited to those that are related to hyperfibrinolysis, promoting wound-clotting, hemophilia, and vessel leakage syndrome. In an embodiment, the modified PAI-1 molecules of the present invention may be used for acute clotting situations. These modified PAI-1 may be used in treatment where preservation of blood clots is desired. For example, for the treatment of hemophilia to promote wound healing. In specific embodiments, the modified PAI-1 is used to treat and prevent Hemophilia A, Hemophilia B and Christmas disease. The modified PAI-1 molecule may be used as a therapeutic that is administered topically for controlling localized bleeding in a subject.

The present invention is directed to a method for downregulating nucleophosmin in a subject in need thereof comprising administering an amount of modified PAI-1 molecule to said subject sufficient to downregulate nucleophosmin in the subject.

The present invention is also directed to a method for treating a proliferative disease in a subject in need thereof, comprising administering a modified PAI-1 molecule to downregulate nucleophosmin in said subject.

The present invention is directed to a method for downregulating fortilin in a subject in need thereof comprising administering a modified PAI-1 molecule to said subject sufficient to downregulate fortilin in the subject.

The present invention is also directed to a method for treating a proliferative disease in a subject in need thereof, comprising administering a modified PAI-1 molecule to downregulate fortilin in said subject.

5.4 COMPOSITIONS

The invention provides methods of treatment, prophylaxis, management, or amelioration by administration to a subject of an effective amount of a modified PAI-1 molecule of the invention. The invention also provides the use of the modified PAI-1 molecules to prepare a medicament. In one aspect, the modified PAI-1 molecule is substantially purified.

The modified PAI-1 molecules of the invention are tested in vitro, and then in vivo for the desired, prior to use in humans. In various specific embodiments, in vitro assays can be carried out with representative cells of cell types (e.g., thyroid cells) involved in a patient's disorder, to determine if a modified PAI-1 molecule has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

Various delivery systems are known and can be used to administer a modified PAI-1 molecule of the invention, e.g., encapsulation in liposomes, microparticles, microcapsules, recombinant cells capable of expressing the modified PAI-1 molecule receptor-mediated endocytosis (see, e.g., Pinto et al, 2006, *Nanomedicine* 2(2):53-65; Degim et al., 2007, *Curr Pharm Des* 13(1):99-117), U.S. Patent Publication No. US 2006/0153798, etc. In another embodiment, the modified PAI-1 molecules can be delivered in a vesicle, in particular a liposome (see Langer, 1990, Science 249:1527 1533 (1990); Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.) Methods of introduction include but are not limited to intradermal, intraperitoneal, intravenous, subcutaneous. The compounds may be administered by any convenient route, for example by infusion or bolus injection and may be administered together with other biologically active agents. Administration can be systemic or local.

In a specific embodiment, it may be desirable to administer the pharmaceutical compositions of the invention locally to the area in need of treatment; this may be achieved by, for example, and not by way of limitation, local infusion during surgery, by means of a catheter, by means of a suppository, or by means of an implant, such as a stent, said implant being of a porous, non-porous, or gelatinous material, including membranes, such as sialastic membranes, or fibers.

In yet another embodiment, the modified PAI-1 molecules can be delivered in a controlled release system. In one embodiment, a pump may be used (see Langer, supra; Sefton, 1987, *CRC Crit. Ref Biomed. Eng.* 14:201; Buchwald et al., 1980, *Surgery* 88:507; Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, thus requiring only a fraction of the systemic dose (see, e.g., Goodson, in *Medical Applications of Controlled Release*, supra, vol. 2, pp. 115 138 (1984)).

Other controlled release systems are discussed in the review by Langer, 1990, *Science* 249:1527 1533 (1990). Other methods of delivery of the therapeutics of the present invention may be used for example, as described in U.S. Pat. No. 5,679,350, which is incorporated by reference in its entirety.

In a specific embodiment, a nucleic acid encoding modified PAI-1 molecules can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286, or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864 1868), etc. Alternatively, a nucleic acid molecule encoding a modified PAI-1 molecule can be introduced intracellularly and incorporated within host cell DNA for expression, by homologous recombination. In certain embodiments, the method of treatment does not include gene therapy.

The present invention also provides pharmaceutical compositions. Such compositions comprise a therapeutically effective amount of a modified PAI-1 molecule and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in "Remington's Pharmaceutical Sciences" by E. W. Martin. Such compositions will contain a therapeutically effective amount of the modified PAI-1 protein molecules preferably in purified form, together with a suitable amount of carrier so as to provide the form for proper administration to the patient. The formulation should suit the mode of administration.

In certain embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The modified PAI-1 molecules of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the modified PAI-1 molecules of the invention which will be effective in the treatment of a particular disorder or condition will depend on the nature of the disorder or condition, and can be determined by standard clinical techniques. In addition, in vitro assays and animal models may optionally be employed to help identify optimal dosage ranges. The precise dose to be employed in the formulation will also depend on the route of administration, and the seriousness of the disease or disorder, and should be decided according to the judgment of the practitioner and each patient's circumstances.

In specific embodiments, the pharmaceutical compositions of the invention are administered via the intravenous route. Suitable dosage ranges for the intravascular administration are 0.01 µg-0.05 µg, 0.05 µg-0.1 µg, 0.1 µg-0.5 µg, 0.5 µg-0.1 µg; 0.1 to 0.5 µg; 0.5 to 1.0 µg; 1 to 5 µg; 5 to 10 µg; 10 µg to 1 mg per dose, in certain embodiments, about 10 µg to 100 µg per dose. In one embodiment, the Therapeutic is administered in two doses, where the second dose is administered 24 hours after the first dose; in another embodiment, the Therapeutic is administered in three doses, with one dose being administered on days 1, 4 and 7 of a 7 day regimen.

In general, effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pack or kit comprising one or more containers comprising one or more active ingredients of the pharmaceutical compositions of the invention. Optionally associated with such container(s) can be a notice in the form prescribed by a governmental agency regulating the manufacture, use or sale of pharmaceuticals or diagnostic products, which notice reflects approval by the agency of manufacture, use or sale for human administration.

5.5 CHARACTERIZATION AND DEMONSTRATION OF THERAPEUTIC OR PROPHYLACTIC UTILITY

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC^{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models of such as cancer animal models such as scid mouse model or nude mice with human tumor grafts known in the art and described in Yamanaka, 2001, *Microbiol Immunol* 2001; 45(7):507 14.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of proliferation or survival of the contacted cells indicates that the Therapeutic is effective to treat the condition in the patient. Alternatively, instead of culturing cells from a patient, Protocols may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, etc.

The principal animal models for cancer known in the art and widely used include mice: all described in Harm et al., 2001, *Curr. Opin. Cell Biol.* 2001 December; 13(6):778 84, which is incorporated herein by reference in its entirety.

Further, any assays known to those skilled in the art can be used to evaluate the prophylactic and/or therapeutic utility of the combinatorial therapies disclosed herein for treatment or prevention of cancer.

5.6 GENE THERAPY

Gene therapy refers to treatment or prevention of a disease performed by the administration of a nucleic acid to a subject who has a disease. For example, the disease or disorder may be a cancer. In one embodiment of the invention, the therapeutic nucleic acid encodes a sequence that produces intracellularly (without a leader sequence) or intercellularly (with a leader sequence), a modified PAI-1 molecule and functionally active fragments, derivatives and analogs thereof.

For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY).

In one aspect, the therapeutic nucleic acid comprises an expression vector that expresses the modified PAI-1 protein and functionally active fragments, derivatives and analogs thereof.

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the modified PAI-1 protein and functionally active fragments, derivatives and analogs thereof. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in biopolymers (e.g., poly-β-1-→4-N-acetylglucosamine polysaccharide; see U.S. Pat. No. 5,635,493), encapsulation in liposomes, microparticles, or microcapsules, or by administering it in linkage to a peptide which is known to enter the nucleus, by administering it in linkage to a ligand which is known to enter the nucleus, by administering it in linkage to a ligand subject to receptor-mediated endocytosis (see e.g., Wu and Wu, 1987, *J. Biol. Chem.* 262:4429-4432), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Young). Alternatively, the nucleic acid can be introduced intracellularly and incorporated within host cell DNA for expression, by homologous recombination (Koller and Smithies, 1989, *Proc. Natl. Acad. Sci. USA* 86:8932-8935; Zijlstra et al., 1989, *Nature* 342:435-438).

Adenoviruses are other viral vectors that can be used in gene therapy. Adenoviruses are especially attractive vehicles for delivering genes to respiratory epithelia where they cause a mild disease. Other targets for adenovirus-based delivery systems are the liver, the central nervous system, endothelial cells, and muscle. Adenoviruses have the advantage of being capable of infecting non-dividing cells. Kozarsky and Wilson, 1993, *Current Opinion in Genetics and Development* 3:499-503 present a review of adenovirus-based gene therapy. Bout et al., 1994, *Human Gene Therapy* 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, *Cell* 68:143-155; and Mastrangeli et al., 1993, *J. Clin. Invest.* 91:225-234. Adeno-associated virus (AAV) has also been proposed for use in gene therapy (Walsh et al., 1993, *Proc. Soc. Exp. Biol. Med.* 204:289-300).

The form and amount of therapeutic nucleic acid envisioned for use depends on the type of disease and the severity of its desired effect, patient state, etc., and can be determined by one skilled in the art.

5.7 PREPARATION OF MODIFIED PAI-1 MOLECULES

The production and use of the modified PAI-1 proteins molecules of the invention are within the scope of the present invention. Described herein are methods for making the foregoing.

The mutations present in the modified PAI-1 molecules of the invention can be produced by various methods known in the art. In one embodiment, the modified PAI-1 molecules may be made by protein synthetic techniques, e.g., using a peptide synthesizer. Wild-type PAI-1 protein sequence is known in the art and provide herein as SEQ ID NO:2. The nucleotide sequences of the cDNA and the gene encoding the human PAI-1 are published and provided herein as SEQ ID NO:1.

Coding regions for the PAI-1 protein can be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, *Molecular Cloning, A Laboratory Manual*, 2d Ed., Cold Spring Harbor Laboratory Press, Cold Spring Harbor, N.Y.; Glover, D. M. (ed.), 1985, *DNA Cloning: A Practical Approach*, MRL Press, Ltd., Oxford, U.K. Vol. I, II).

The modified PAI-1 molecules may be derived from other PAI-1 homologs. These PAI-1 homologs may be obtained by screening genomic libraries from other animals. The modified PAI-1 molecules may also be prepared by random mutations as disclosed in Berkempas et al., 1995, Embo J. 14: 2969-2977. Using this approach, the VLHL PAI-1 nucleotide sequence can be amplified by multiple cycles of error-prone FCR, gel purified and re-amplified using standard PCR methods to produce a pool of randomly mutated VLHL PAI-1 cDNA which comprises random nucleotide substitutions. The PCR product can be ligated into the plasmid, transfected into a bacteria for expression of the modified PAI-1 molecules. The modified PAI-1 molecules exhibits at least about 80% overall similarity at the amino acid level to the amino acid sequence of SEQ ID NO:2, exhibits at least about 85-90% overall similarity to the amino acid sequence of SEQ ID NO:2, or exhibits at least about 90-95%, 95%-97%, 97%-98%, 98%-99.3%, 99.3%-99.5%, 99.5%-99.7% overall similarity to the amino acid sequence of SEQ ID NO:2. The modified PAI-1 molecules exhibits at least about 80% overall identity at the amino acid level to the amino acid sequence of SEQ ID NO:2, exhibits at least about 85-90% overall similarity to the amino acid sequence of SEQ ID NO:2, or exhibits at least about 90-95%, 95%-97%, 97%-98%, 98%-99.3%, 99.3%-99.5%, 99.5%-99.7% overall similarity to the amino acid sequence of SEQ ID NO:2. Such nucleic acid molecule that hybridizes to another nucleic acid consisting of the complement of the DNA sequences that encode the amino acid sequence of SEQ ID NO:2 under moderately or low stringent conditions, e.g., hybridization to filter-bound DNA in 6×SSC at 45° C., and washing in 2×SSC at 50° C. (Ausubel F. M. et al., eds., 1989, *Current Protocols in Molecular Biology*, Vol. I, Green Publishing Associates, Inc., and John Wiley & sons, Inc., New York, at page 2.10.3).

The modified PAI-1 molecules may also be derived from other naturally occurring variants of PAI-1, and degenerate variants thereof. A PAI-1 variants exhibits at least about 80% overall identity at the nucleotide level to the nucleic acid sequence of SEQ ID NO:1, exhibits at least about 85-90% overall identity to the nucleic acid sequence of SEQ ID NO:1 or exhibits at least about 95%-97%, 97%-98%, 98%-99.3%, 99.9%-99.5%, 99.5%-99.7% overall identity to the nucleic acid sequence of SEQ ID NO:1. A PAI-1 variants exhibits at least about 80% overall identity at the nucleotide level to the nucleic acid sequence of SEQ ID NO:1, exhibits at least about 85-90% overall identity to the nucleic acid sequence of SEQ ID NO:1 or exhibits at least about 95%-97%, 97%-98%, 98%-99.3%, 99.9%-99.5%, 99.5%-99.7% overall identity to the nucleic acid sequence of SEQ ID NO:1 The degree of identity can be determined by analyzing sequence data using a computer algorithm, such as those used by the BLAST computer program.

In specific embodiments, transformation of host cells with recombinant DNA molecules that encode the modified PAI-1 molecule, cDNA, or synthesized DNA sequence enables generation of multiple copies of the recombinant DNA molecule.

Additionally, the nucleic acid sequence encoding the PAI-1 molecule can be mutated in vitro or in vivo to create variations in coding regions (e.g., amino acid substitutions, additions, deletions, inversions), and/or to create and/or destroy translation, initiation, and/or termination sequences, and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), PCR-based overlap extension (Ho et al., 1989, Gene 77:51-59), PCR-based megaprimer mutagenesis (Sarkar et al., 1990, Biotechniques, 8:404-407), etc. Mutations can be confirmed by double stranded dideoxy DNA sequencing.

The amino acid to be introduced within the sequence may be selected from members of the same (conservative substitution) or different class (non-conservative substitution) to which the amino acid being substituted belongs. The nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. In an embodiment, the substitutions result in a modified PAI-1 molecule that displays increased half-life of the active form and decreased functional activity to uPA, tPA and/or Vn, and/or a decreased Serpin activity.

In making amino acid substitutions, the hydropathic index of amino acid residues can be considered. The importance of the hydropathic amino acid index in conferring interactive biologic function on a peptide is generally understood in the art (Kyte & Doolittle, *J. Mol. Biol.*, 157: 105-132, 1982). It is known that certain amino acids can be substituted for other amino acids having a similar hydropathic index and still result in a peptide with similar biological activity. Also, in order to abolish or decrease a certain interactive biologic function of a peptide, certain amino acid residues can be substituted for other amino acid residues having a different hydropathic index. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is understood in the art that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those within ±1 are particularly preferred, and those within ±0.5 are even more particularly preferred. Also, in order to abolish or decrease a certain functional activity in a peptide, certain amino acid residues can be substituted for other amino acid residues having a different hydropathic character. In such changes, the substitution of amino acid residues whose hydrophobic values, are within ±1.5, ±2.0, ±2.5, ±3.0, ±4.0, ±4.5, ±5.0, ±5.5, ±6.0.

Substitution of like amino acids can also be made on the basis of hydrophilicity, particularly where the biological functional equivalent peptide thereby created is intended for use in immunological embodiments. U.S. Pat. No. 4,554,101, incorporated herein by reference, states that the greatest local average hydrophilicity of a peptide, as governed by the hydrophilicity of its adjacent amino acids, correlates with its immunogenicity and antigenicity, i.e. with a biological property of the peptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−05±1); threonine (−0.4); alanine (−0.5); histidine (−0.5); cysteine (−1.0); methionine (−1.3); value (−1.5); leucine (−1.8); isoleucine (−1.8); tyrosine (−2.3); phenylalanine (2.5); tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take following characteristics into consideration are well known to those of skill in the art and include: arginine and lysine; glutamate and aspartate; serine and threonine; glutamine and asparagine; and valine, leucine and isoleucine. The present invention thus contemplates functional or biological equivalents of a peptide inhibitor of plasminogen activator inhibitor-1 as set forth above. Also, for the purposes of this invention, amino acid substitutions provide modified PAI-1 molecules having new properties such that a functional activity is abolished or decreased. In this case, it is useful to substitute amino acid residues with other amino acid residues that have different side-chain substituents, or different hydrophobicity, hydrophilicity, charge, size and the like. In such changes, the substitution of amino acid residues whose hydrophilicity values, are within ±1.5, ±2.0, ±2.5, ±3.0, ±3.5, ±4.0, ±4.5, ±5.0, ±5.5, ±6.0.

Manipulations of the modified PAI-1 protein sequence may also be made at the protein level. Included within the scope of the invention are modified PAI-1 protein molecules which are differentially modified during or after translation, e.g., by glycosylation, acetylation, phosphorylation, amidation, derivatization by known protecting/blocking groups, proteolytic cleavage, linkage to other proteins, etc. Numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin, etc.

In addition, modified PAI-1 molecules can be chemically synthesized. For example, a peptide corresponding to a portion of a modified PAI-1 protein which comprises the desired mutation can be synthesized by use of a peptide synthesizer. Furthermore, if desired, nonclassical amino acids or chemical amino acid analogs can be introduced as a substitution or addition into the modified PAI-1 protein sequence. Non-classical amino acids include, but are not limited to, the D-isomers of the common amino acids, α-amino isobutyric acid, 4-aminobutyric acid, Abu, 2 amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In specific embodiments, the modified PAI-1 protein comprises a fusion protein that is produced by recombinant expression of a nucleic acid encoding a modified PAI-1 protein joined in-frame to the coding sequence for another protein, such as but not limited to toxins, such as ricin or diphtheria toxin. Such a fusion protein can be made by ligating the appropriate nucleic acid sequences encoding the desired amino acid sequences to each other by methods known in the art, in the proper coding frame, and expressing the fusion protein by methods commonly known in the art. Alternatively, such a fusion protein may be made by protein synthetic techniques, e.g., by use of a peptide synthesizer. Chimeric genes comprising portions of modified PAI-1 protein fused to any heterologous protein-encoding sequences may be constructed.

In other embodiments, the modified PAI-1 molecules are conjugated to a detectable agent. These detectable modified PAI-1 molecules may be used to monitor the modified PAI-1 molecule after its administration. Such detection can accomplished by coupling the modified PAI-1 molecules to detectable substances including, but not limited to various enzymes, such as but not limited to horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}I$, $^{125}I$, $^{123}I$, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, and noradioactive paramagnetic metal ions are radiolabelled or conjugated to specific radioisotopes.

The present invention further encompasses uses of modified PAI-1 molecules conjugated to a therapeutic agent.

A molecule may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, the modified PAI-1 molecules may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")), a chemotherapeutic agent or other type of toxin, e.g., a ricin toxin, or a radionuclide, or any other agent effective to kill cancer or tumor cells or to arrest cancer cell growth. The modified PAI-1 molecules may be conjugated to an antibiotic, antifungal or anti-viral agent.

Moreover, the modified PAI-1 molecules may be conjugated to therapeutic moieties such as a radioactive metal ion, such as alph-emiters such as 213Bi or macrocyclic chelators useful for conjugating radiometal ions, including but not limited to, 131In, 131LU, 131Y, 131Ho, 131Sm, to polypeptides.

In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., Clin Cancer Res. 4(10):2483-90 (1998); Peterson et al. Bioconjug. Chem. 10(4):553-7 (1999); and Zimmerman et al., Nucl. Med. Biol. 26(8):943-50 (1999) each incorporated by reference in their entireties.

In specific embodiments, the modified PAI-1 molecule is conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In a specific embodiment, a vector is used that comprises one or more promoters operably linked to the coding region of a modified PAI-1 molecule, an origin of replication, and, optionally, a selectable marker (e.g., an antibiotic resistance gene).

A host cell strain may be chosen which modulates the expression of the inserted sequences, or modifies and processes the gene product in the specific fashion desired. Expression from certain promoters can be elevated in the presence of certain inducers; thus, expression of the genetically engineered modified PAI-1 proteins may be controlled. Furthermore, different host cells have characteristics and specific mechanisms for the translational and post-translational processing and modification (e.g., glycosylation, phosphorylation of proteins). Appropriate cell lines or host systems can be chosen to ensure the desired modification and processing of the foreign protein expressed. Expression in mammalian cells can be used to ensure "native" glycosylation of a heterologous protein. Furthermore, different vector/host expression systems may effect processing reactions to different extent.

Once a recombinant host cell expresses the modified PAI-1 molecule, it can be purified and analyzed. Methods of purification and analysis is well known in the art. Analysis of the modified PAI-1 molecule may be achieved by assays based on the physical or functional properties of the product, including radioactive labeling of the product followed by analysis by gel electrophoresis, immunoassay, etc. In particular, in vivo half-life and functional activities of the active form of the modified PAI-1 molecule are measured.

5.8 STRUCTURE PREDICTION AND FUNCTIONAL ANALYSIS OF MODIFIED PAI-1 MOLECULE

Since the function of a modified PAI-1 molecule is determined by its structure, it would be valuable if the structure of a modified PAI-1 molecule may be predicted based on the amino acid sequence, which thereby allows for the routine design of a modified PAI-1 molecule with particular functional properties. Structure prediction, analysis of crystallographic data, sequence alignment, as well as homology modeling, can be accomplished using computer software programs available in the art, such as BLAST, CHARMm release 21.2 for the Convex, and QUANTA v.3.3, (Molecular Simulations, Inc., York, United Kingdom).

The modified PAI-1 molecule sequence can be characterized by a hydrophilicity analysis (Hopp, T. and Woods, K., 1981, *Proc. Natl. Acad. Sci. U.S.A.* 78:3824). A hydrophilicity profile can be used to identify the hydrophobic and hydrophilic regions of the PAI-1 protein and the corresponding regions of the gene sequence which encode such regions. Secondary structural analysis (Chou, P. and Fasman, G., 1974, *Biochemistry* 13:222) can also be done, to identify regions of the PAI-1 protein that assume specific secondary structures. Other methods of structural analysis can also be employed. These include but are not limited to X-ray crystallography (Engstom, A., 1974, *Biochem. Exp. Biol.* 11:7-13) and computer modeling (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

The functional activity of modified PAI-1 molecules can be assayed by various methods known in the art. For example, where one is assaying for the ability of a modified PAI-1 molecule to bind to an antibody, uPA, tPA, Vn, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Antibody binding can be detected by detecting a label on the primary antibody. Alternatively, the primary antibody is detected by detecting binding of a secondary antibody or reagent to the primary antibody, particularly where the secondary antibody is labeled. Many means are known in the art for detecting binding in an immunoassay and are within the scope of the present invention.

A specific functional assay for the modified PAI-1 molecule that may be used in the present invention is based on the immobilisation of functional active binding partners, such as tPA, uPA or Vn, to plates by means of monoclonal antibodies. The modified PAI-1 molecule binds to a binding partner and is then quantified using a peroxidase labeled monoclonal anti PAI-1 antibody. Another specific functional assay for measuring PAI-1 function is, for example, the amidolytic assay.

Other functions of PAI-1 include, but are not limited to, binding to uPA, tissue-type plasminogen activator, integrin-alpha-3-beta-2, and vitronectin. In an embodiment, the modified PAI-1 molecule does not bind to at least one of the binding partners including uPA, tPA and Vn. In another embodiment, the modified PAI-1 molecule does not bind to integrin. In another embodiment, the modified PAI-1 molecule has reduced serpin activity.

The half-life of a protein is a measurement of protein stability and indicates the time necessary for a one half reduction in the concentration of the protein. The half-life of a modified PAI-1 can be determined by any method for measuring PAI-1 levels in samples from a subject over a period of time, for example but not limited to, immunoassays using anti PAI-1 antibodies to measure the levels of the modified PAI-1 molecules in samples taken over a period of time after administration of the modified PAI-1 or detection of radiolabelled modified PAI-1 molecules in samples taken from a subject after administration of the radiolabeled modified PAI-1 molecules.

Other methods of measuring the functions and binding activities of the modified PAI-1 are known to the skilled artisan and are within the scope of the invention.

6. EXAMPLES

As demonstrated herein below, modified PAI-1 molecules were created that exhibit an extended half-life of the active conformation and display a decrease in binding activity to and/or specific activity against at least one of the following molecules: uPA, tPA and Vn. The modified PAI-1 molecules were shown to reduce cancer cell growth. These modified PAI-1 molecules were shown to downregulate nucleophosmin and/or fortillin, two proteins implicated in important cancer processes (cell growth, cell cycle, malignant transformation, etc.). Thus, the results presented here indicate that modified PAI-1 molecules of the present invention can therefore be used to treat and/or ameliorate a symptom of cancer.

6.1 PRODUCTION OF MODIFIED PAI-1 MOLECULES

A baculovirus expression system basically as described in Amagata et al., 2003, *J. Nat. Prod.* 66:230-235, 2003 was used. The supernatant from lysed cells was loaded onto a column packed with nickel resin (Invitrogen) at a flow rate of 0.3 mL/min (GradiFrac system, Pharmacia Biotech). The column was then washed with wash buffer containing 40 mM imidazole in native buffer at a flow rate of 1 mL/min until no proteins were detected. The protein was then eluted from the column using a gradient of 40-250 mM imidazole in native buffer at a flow rate of 1 mL/min. The peak fractions were dialyzed to remove imidazole and concentrated to a desired concentration for further analysis.

A modified PAI-1 molecule of the present invention was expressed in a baculovirus expression system. A cDNA encoding VLHL was excised from the VLHL PAI-1 plasmid as a NdeI/Xho I fragment. The PCR product encoding the VLHL PAI-1 NdeI/Xho I fragment was ligated into the pFastbac plasmid containing a methione and a 6His purification tag and a linker DYDIPTTENLYFQGAMDPEF (SEQ ID NO:8) or the sequence MSSYHHHHHH (SEQ ID NO:38) followed by a linker was added at the N-terminal. The baculovirus expression system produced about 20 mg of protein from 1 liter of cell culture. In the pFastbac vector, the expression of the gene is controlled by the *Autographa californica* multiple nuclear polyhedrosis virus (AcMNPV), polyhedrin (PH), or the p10 promoter for high-level expression in insect cells.

The plasmids were transposed into a recombinant bacmid with the help of DH10Bac *E. coli* cells (Invitrogen), which contain a baculovirus shuttle vector (Bacmid) with a min-attTn7 target site and a helper plasmid. The recombinant bacmid DNA was isolated from the white colonies grown for 48 h at 37° C. on a LB agar plate containing 50 mg/L kanamycin, 7 mg/L gentamycin, 10 mg/L tetracycline, 100 mg/L X-gal and 40 mg/L, IPTG and which was used to transfect Sf 9 cells derived from *Spodoptera Frugiperda* (Fall Armyworm) by cellfectin reagent (Invitrogen). The virus was amplified to approximately 2×10⁷ plaque forming units (pfu)/mL and was added to Sf 9 cells (~2×106/mL) in 6 well culture plates. The plates were incubated at 27° C. for different time intervals. The virus was subsequently amplified to approximately 2×10⁸ plaque forming units (pfu)/mL and was used to infect Sf 9 cells (approximately 2×10⁶/mL) on a large scale (1 L cell culture). The cells were harvested and lysed by two freeze-thaw cycles. The lysate was then centrifuged at 3,000×g for 20 minutes to pellet the cellular debris. The supernatant was transferred to a fresh tube for purification. The supernatant was loaded onto a column packed with nickel resin (Invitrogen) at a flow rate of 0.4 ml/min and the column was then washed with a buffer containing 40 mM imidazole in 20 mM Hepes buffer pH 8.0, and protease inhibitors until no washed proteins were detected. The protein was then eluted using a gradient of 40-250 mM imidazole in native buffer. The peak fractions were dialyzed to remove imidazole and concentrated to a desired concentration. VLHL PAI-1 was active against uPA, however $VLHL_{NS}$ PAI-1 was not. Purity was determined as +95%.

6.2 $VLHL_{NS}$ PAI-1 MUTATION

Modified PAI-1 molecules have been prepared which display increased half-life and are deficient in one or more functional activities as compared to wild-type PAI-1 protein. These modified PAI-1 molecules are described in Sections 6.2-6.8.

The $VLHL_{NS}$ PAI-1 mutant has the following amino acid substitutions: Gln 197 with Cys, Gly 355 with Cys, and Arg 369 with Ala. The amino acid sequence of $VLHL_{NS}$ is depicted in FIG. 1. The cysteine substitutions produced a PAI-1 with a half-life of over 700 hrs. (Chorostowsta-Wynimko, et al. 2003, Mol Cancer Ther 2:19-28, 2003 and U.S. Patent Application Publication No. US2005/0158295).

The mutation at 369 (at P1, Arg369Ala) was introduced by PCR using the NdeI/XhoI fragment of the VLHL PAI-1 plasmid and the gene was transferred into the baculovirus vector. The $VLHL_{NS}$ PAI-1 remained in an active conformation for an extended period of time relative to wild-type PAI-1 (about 6900 hours and evaluated for 700 hours), but did not exhibit any inhibitory activity toward uPA or lPA (that is, the modified PAI-1 molecule exhibit no serpin activity). Assays for measuring UPA and tPA activity are well known in the art, e.g., see, Harvey et al., 1988, *Clin Exp Metastasis* 6(6):431-50. Each PAI-1 DNA construct that encode the modified PAI-1 molecules was sequenced to confirm mutations by MWG-BIOTECH, Inc., Mendenhall Oaks Parkway, N.C. 27265.

6.3 $VLHL_{NV}$ PAI-1 MUTATION

The $VLHL_{NV}$ PAI-1 mutant has the following amino acid substitutions: Gln 197 with Cys, Gly 355 with Cys, and Gln 146 with Lys. The mutation Gln146Lys was introduced by PCR using the Ndel/Xho fragment of the VLHL PAI-1 plasmid and the gene was transferred into the baculovirus vector. The $VLHL_{NV}$ PAI-1 remained in an active conformation, but did not have any binding activity toward vitronectin. Assays for measuring VN binding of specific activity is well known in the art, e.g., see Salonen et al., 1989, *Biol Chem* 264(11): 6339-43.

6.4 $VLHL_{NT}$ PAI-1 MUTANT

The $VLHL_{NT}$ PAI-1 mutant has the following amino acid substitutions: Gln 197 with Cys, Gly 355 with Cys, and Asn 352 with Pro. The mutation Asn352Pro was introduced by PCR using the Ndel/Xho fragment of the VLHL PAI-1 plasmid and the gene was transferred into the baculovirus vector. The $VLHL_{NT}$ PAI-1 remained in an active conformation, but did not have any binding activity toward tPA. Assays for determining binding activity and/or specific activity is known is the art. See Jankun et al., 1991, Cancer Res 51(4):1221-6.

6.5 $VLHL_{NS, NV}$ PAI-1 MUTANT

The $VLHL_{NS, NV}$ PAI-1 mutant has the following amino acid substitutions: Gln 197 with Cys, Gly 355 with Cys, Arg 369 with Ala, and Gln 146 with Lys. The $VLHL_{NS, NV}$ PAI-1 mutant remained in an active conformation, but did not have serpin activity (against uPA and tPA) or vitronectin binding activity.

6.6 $VLHL_{NS, NT}$ PAI-1 MUTANT

The $VLHL_{NS, NT}$ PAI-1 mutant has the following amino acid substitutions: Gln 197 with Cys, Gly 355 with Cys, Arg 369 with Ala, and Asn 352 with Pro. The $VLHL_{NS, NT}$ PAI-1 mutant remained in an active conformation, but did not have serpin activity (against uPA and tPA), no tPA or vitronectin binding activity.

6.7 $VLHL_{NS, NV, NT}$ PAI-1 MUTANT

The $VLHL_{NS, NV, NT}$ PAI-1 mutant has the following amino acid substitutions: Gln 197 with Cys, Gly 355 with Cys, Arg 369 with Ala, Gln 146 with Lys, and Asn 352 with Pro. The $VLHL_{NS, NV, NT}$ PAI-1 mutant remained in an active conformation, but did not have serpin activity (against uPA and tPA), no tPA or vitronectin binding activity.

6.8 $VLHL_{NV}$ MINI PAI-1 MUTANT

The $VLHL_{NV}$ mini PAI-1 mutant has the following amino acid substitutions: Gln 197 with Cys, Gly 355 with Cys, and Gln 146 with Lys. Amino acid residues at positions 127 to 181 (of SEQ ID NO:2) were deleted to form the mini PAI-1 mutant, in which helix E, F, G were truncated. The $VLHL_{NV}$ mini PAI-1 mutant remained in an active conformation, but did not have vitronectin binding activity.

6.9 AMIDOLYTIC ASSAY FOR MEASURING uPA INHIBITORY ACTIVITY

Tris (50 mM) with 0.01% Tween 80, 0.01% PEG 8000 (pH 8.8) and 10 KIU/ml sterile aprotinin (Sigma Chemical Co., St. Louis, Mo.) was incubated with 1 μg of uPA and decreasing amounts of inhibitor (initially 100 μg/ml) for 15 minutes; 100 μl of this mixture was incubated in 96-well microplates with 50 μl of 2.5 mM Spectozyme UK (Cbo-L-(γ)-Glu (α-t-BuO)-Gly-Arg-pNA.2AcOH), (American Diagnostica Inc., Greenwich, Conn.), for 15 mins. Absorbance at 405 nm was read on a microplate reader. Absorbance is inversely proportional to the uPA inhibitory activity.

6.10 SPECTROZYME® ASSAY OF PAI-1 ACTIVITY

Assay for evaluating PAI-1 activity was performed as described by the manufacturer (American Diagnostica Inc., Stamford, Conn.) with minor modifications. Briefly, equal volumes (50 μL) of VLHL-PAI-1 (diluted with $H_2O$ from the stock of 1.0 mg/mL in 20 mM Hepes, 250 mM imidazole, pH 8.0 to a concentration 0.06 mg/mL) and HMW uPA from American Diagnostica Inc., Stamford, Conn. (0.3 mg/mL in water) were mixed and incubated for 15 min at room temperature, followed by the addition of 50 µL of the chromogenic substrate of uPA (Spectrozyme uPA® American Diagnostica Inc., Stamford, Conn., final concentration of 1.7 mM). The absorbance was measured at 405 nm in a 96-well plate reader. Urokinase alone and wtPAI-1/uPA were used as controls.

6.11 PAI-1/UPA COMPLEX FORMATION ASSAY

PAI-1 and uPA mixed as described above and incubated for 15 minutes at 37° C. and were run on a PAGE gel and stained with Coomassie Blue stain.

6.12 MOLECULAR GRAPHICS

SwissPDB, Chain v.7 and PyMOL viewers were used to display the three-dimensional structures of proteins and to generate POV-Ray scenes (PyMOL v. 0.98 DeLano, The PyMOL Molecular Graphics System, 2005; Guex et al., 1997, *Electrophoresis* 18:2714-2723). Protein alignment was done using the program ALIGN (Cohen, 1997, *Journal of Applied Crystallography* 30:1160-1161).

6.13 NON-REDUCING GEL ELECTROPHORESIS

Electrophoresis was performed at room temperature in gradient gels with 4-12% polyacrylamide, in the absence of β-mercaptoethanol. All gradient gels were scanned, and converted to black and white images. Contrast and/or brightness were adjusted if needed. The following molecular weight standards were used: 191, 97, 64, 51, 39, 28, 19 and 14 kDa.

6.14 2D GEL ELECTROPHORESIS

The control and treated cells were harvested, washed five times in wash buffer (10 mM Tris HCl and 5 mM magnesium acetate) and suspended in lysis buffer (8 M urea, 2 M thiourea, 4% chaps, 65 mM DTT, 40 mM Tris, 1% IPG buffer (pH 4-7, Amersham Biosciences)) on ice for 10 Min, followed by sonication, centrifugation at 21,000×g for 15 minutes. Supernatant was collected and protein concentration was measured by Bradford method (28). 500 µg of each samples in 350 µL was used to rehydrate the 18 cm, pH 4-7 or 3-10 IPG strip (GE health care) for 18 hrs. Proteins were focused in an IPG-Phor system with the setting of 500 V (~2.5 hrs) and 3500 V (~17 hrs). Next, strips were equilibrated for 20 minutes in equilibration buffer (6M urea, 1% SDS, 30% glycerol, 50 mM Tris HCl, 32.4 mM DTT, pH 6.8) and then alkylated for 20 minutes in equilibration buffer containing 244.5 mM iodoacetamide. The proteins were then separated on 12% gel using Ettan Dalt Six (24 cm×20 cm) gel system at 10° C., constant current (30 mA/gel for initial 1 hr followed by 50 mA/gel) until the tracking dye reached the bottom.

6.15 WESTERN BLOT ANALYSIS

The PAGE gel was equilibrated in Transfer Buffer-TBS (24% methanol, 96 mM glycine, 12 mM Tris-HCl) for 5 min and proteins were transferred to a nitrocellulose membrane, washed in Blotting Buffer-TBST (PBS, pH 7.6 and 0.1% Tween-20), blocked in Blotting Buffer containing 5% non-fat dry milk for 1.5 hrs at 40° C. The membrane then was treated with rabbit anti-human PAI-1 (American Diagnostica Inc., 2 µg/mL) overnight in TBST/milk solution at 40° C. The next morning, the membrane was washed 3 times in TBST for 5 min at room temperature. The second antibody was added (anti-rabbit IgG Sigma, Inc., in 1:4,000 dilution) in TBST/milk solution for 1 hr at room temperature followed by washing (3 times in TBST and once in TBS for 5 min).

6.16 STAINING OF FREE —SH WITH FLUORESCENT DYE

The purified VLHL PAI-1 and VLHL$_{NS}$ PAI-1 were incubated with TCEP (a reducing agent, Tris(2-carboxyethyl) phosphine) up to a final concentration of 65 mM for 2 hrs at room temperature, followed by staining with 5-IAF dye (5-iodoacetamidofluorescein, from Molecular Probes) at a final concentration of 1 mM for 2 hrs in the dark. This dye binds to —SH thiols, but not to disulfide bridges of the VLHL PAI-1s. All samples were then processed for SDS PAGE (performed in the dark). Protein bands were visualized under a UV transilluminator, photographed, and then the same gel was stained with Coomassie Blue.

6.17 IN-GEL DIGESTION WITH TRYPSIN

The proteins stained with Coomassie blue were excised from the 4-12% gradient SDS PAGE gel and destained later with 30% methanol for 3 hr at room temperature. In-gel proteolysis with modified, sequencing grade trypsin (Promega, Madison, Wis.) was done essentially as previously described (Basrur, et al.: Proteomic analysis of early melanosomes: identification of novel melanosomal proteins. J. Proteome Res. 2:69-79, 2003.)

6.18 PAI-1 AND PAI-1/UPA COMPLEX IDENTIFICATION BY PEPTIDE SEQUENCING USING LIQUID CHROMATOGRAPHY-TANDEM MASS SPECTROMETER (LC-MS)

2 µl of the digest was separated on a reverse phase column (Aquasil C18, 15 µm tip×75 µm id×5 cm Picofrit column, New Objectives, Woburn, Mass.) using an acetonitrile/1% acetic acid gradient system (5-75% acetonitrile over 35 mins followed by 95% acetonitrile wash for 5 min) at a flow rate of 250 nL/min. Peptides were directly introduced into an ion-trap mass spectrometer (LCQ, ThermoFinnigan) equipped with a nano-spray source. The mass spectrometer was set for analyzing the positive ions and acquiring a full MS scan of a collision induced dissociation spectrum on the most abundant ion from the full MS scan (relative collision energy ~30%). Dynamic exclusion was set to collect 3 (collision-induced dissociation) spectra on the most abundant ion and then exclude it for 2 min. CID spectra were manually verified by comparison with an in-silico tryptic digest of published protein sequences using the MS-Digest and MS-Product provisions of Protein Prospector (http://prospector.ucsf.edu). All LC-MS experiments were done at Proteomics Laboratory, Program in Bioinformatics & Proteomics/Genomics at the Health Science Campus of the University of Toledo.

6.19 CELL CULTURE

Cells (LnCAP) were seeded in T25 or T75 flasks in MEM media with 10% FBS and antibiotics and incubated until the cells reached ~70% confluence. Cells were treated in fresh media with different concentrations of PAI-1 (final concentrations in media: 1, 10, 50, 100 µg/mL) or an irrelevant protein.

6.20 CELL PROLIFERATION ASSAY

Prostate cancer cells were seeded at a density of $5 \times 10^4$ cells/well in MEM media with 10% FBS and antibiotics and incubated (96-well cell culture plate) until the cells reached ~70% confluence. LnCAP cells were treated for up to 72 hr with different concentrations of PAI-1 (final concentrations in media: 1, 10, 50, 100 μg/mL) or an irrelevant protein or appropriate buffer in control samples. After treatment, the number of viable cells was determined using Promega's Cell-Titer 96 AQueous MTS Assay (Madison, Wis.) according to the manufacturer's instructions. Cell proliferation was determined as a fraction of the control sample and measured as absorbance at 540 nm. Each concentration or control results represent an average of 6 to 16 wells.

6.21 CELL VIABILITY

Viability of the cells was determined by trypan blue exclusion method.

6.22 REMOVAL OF CELL SURFACE-ASSOCIATED PROTEINS

An acid wash was performed in a manner similar to described in Jankun et al., 1991, Cancer Res. 51:1221-1226. Cells were treated with 3 mL of 50 mM glycine-HCl, 0.1 M NaCl, pH 3.0. Acid wash was quickly neutralized with 0.9 mL of 0.5 M Tris-HCl, pH 7.8. The samples were concentrated using Vivaspin 20 concentrators (10,000 MWCO from Vivascience Company, Inc.). The final concentration of total protein ranged from 1.0 to 2.6 mg/mL.

6.23 RESULTS

6.23.1 Purified VLHL

Modified PAI-1 molecules that exhibit extend half-life of the active form can be formed by the introduction of Cys mutations are described in Chorostowska-Wynimko et al., 2003, Mol. Cancer Ther. 2:19-28. U.S. Patent Application Publication No. 2005/0158295. As shown in FIG. 2, cysteines form bridges between the A3 and A5 strands, preventing collapse of the reactive loop into the PAI-1 molecule and consequently preclude conversion of the active form to the latent form. One of these mutants has half-life of over 700 hrs (VLHL PAI-1) in contrast to 2 hrs for the wild-type PAI-1 (Seiffert et al., 1991, Biochim. Biophys. Acta. 1078:23-30). To increase the yield, VLHL PAI-1 was expressed in baculovirus. All vectors encoding the modified PAI-1 molecules of the present invention have been sequenced, validating the sequences of modified PAI-1 molecules comprising linker, purification tag, and desired mutations.

The VLHL yielded ~95% pure protein (~18 mg/l) in a single-step purification as determined by PAGE gel densitometry (FIG. 4). VLHL was produced in high purity (+95%), predominantly in the active conformation.

6.23.2 UROKINASE INHIBITORY ACTIVITY OF THE MODIFIED PAI-1 MOLECULES

In order to measure the activity of the modified PAI-1 molecules of the present invention, urokinase inhibitory activities of VLHL and $VLHL_{NS}$ were determined. The active form of VLHL inhibits urokinase activity, as determined by a chromogenic assay with Spectrozyme®. The PAI-1 mutant with Arg369→Ala in the P1 position ($VLHL_{NS}$) shows no activity against uPA.

VLHL and $VLHL_{NS}$ were incubated with uPA and run on a PAGE gel. Active PAI-1 produces a band of protein of the molecular weight characteristic of PAI-1/uPA, while $VLHL_{NS}$ PAI-1 mutant (Arg369→Ala in the P1 position) does not. The protein band of uPA/VLHL was excised from gel and analyzed by MS-LC (FIG. 5)(Table 2). No other peptides but those of PAI-1 and uPA were identified, further confirming the formation of the uPA/PAI-1 complex and VLHL activity.

TABLE 1

Sequence of peptides extracted from band of uPA/PAI-1 complex on PAGE gel

| Protein Accession No. | Protein Names | Theoretical Mass | Observed Mass | Peptide Sequence |
|---|---|---|---|---|
| P05121 | Plasminogen activator inhibitor type one (PAI-1) | 1144.53 | 1144.84 | 200-209 TPFPDSSTHR |
| | | 859.46 | 859.54 | 178-185 GAVDQLTR |
| | | 1105.60 | 1105.26 | 42-51 VGQQVAQASK |
| | | 1684.75 | 1685.02 | 215-230 SDGSTVSVPmmAQTNK |
| | | 1108.52 | 1108.74 | 146-154 QVDFSEVER |
| | | 1583.75 | 1583.52 | 311-323 KPLENLGmTDmFR |
| | | 948.51 | 948k80 | 169-177 GmISNLLGK |
| | | 1494.74 | 1494.92 | 112-124 DEISTTDAIFVQR |
| | | 1208.61 | 1208.24 | 301-310 FSLETEVDLR |
| | | 1034.56 | 1034.86 | 157-164 FIINDWVK |
| P00749 | Urokinase plasminogeon Activator | 593.33 | 593.45 | 334-338 mTVVK |
| | | 935.49 | 935.14 | 404-411 DKPGVYTR |
| | | 1111.59 | 1111.94 | 156-165 KPSSPPEELK |
| | | 1198.60 | 1199.80 | 421-431 SHTKEENGLAL |
| | | 1001.56 | 1001.16 | 109-118 SDALQLGLGK |
| | | 1241.68 | 1241.92 | 254-263 FEVENLILHK |
| | | 1047.49 | 1047.94 | 350-358 [1]YYGSEVTTK | m, oxidized methionine;
[1]non-tryptic

Under oxidizing conditions when cysteines form disulfide bridges (Cys197 and Cys355), the RCL (reactive center loop) is immobilized and cannot be inserted into the PAI-1 molecule (FIG. 2). Consequently, reduction of the disulfide bond by reducing agent should restore A3, A5 and RCL mobility, making conversion of VLHL to the latent form possible. Purified VLHL and VLHL$_{NS}$ and wt PAI-1 were treated with DTT (10 to 65 mM) for up to three hours. DTT treated VLHL and VLHL$_{NS}$ did not form complexes and did not express any uPA inhibitory activity. VLHL and VLHL$_{NS}$ treated with DTT convert into the latent form, as wild-type PAI-1 does, and migrate as a single band corresponding to the latent form of VLHL (FIG. 6). This indicates that although disulfide bridges can be formed in the VLHL and VLHL$_{NS}$, these bridges can be reduced so that conversion to the latent form is possible. Once these modified PAI-1 molecules exhibit the latent form, they are inactive to uPA.

Also, as shown in FIG. 6, VLHL and VLHL$_{NS}$ were stained with a fluorescent dye to determine presence of free thiols in the modified PAI-1 molecule. VLHL in the active conformation showed no or very little fluorescence, while DTT treated, inactive VLHL in the latent conformation showed a strong signal of 5-1AF dye bound to the —SH of cysteine. The same was seen for VLHL$_{NS}$. The wild-type PAI-1 purified from HT1080 cells, containing the full sequence of amino acids including Cys9 (the only Cys in this protein), showed strong fluorescence in both active and latent forms. VLHL do not have this cysteine since the first 23 amino acids are truncated from the protein sequence. This shows that free thiols, which is indicative of the latent form, predominates in wild-type PAI-1 but not in VLHL and VLHL$_{NS}$.

Usually wild-type PAI-1 in the active form migrates on PAGE gel as the upper band and the latent and RCC (reactive center loop-cleaved) forms migrate below it. However, PAI-1 with cysteine mutations that form disulfide bonds migrates below its latent or RCC forms, which is completely contrary to the wild-type form of PAI-1 (FIG. 4). It is possible that in PAI-1s with Cys mutations in the A3 and A5 strands, the reactive loop that forms a bulge on the left side of PAI-1 (when facing this protein) is shifted to the right side resulting in a more spherical molecule that moves easier through the gel.

From these experiments, it is concluded that the disulfide bridge (Cys 197, 355) extended the half-life of the active form of the modified PAI-1 molecules of the invention. VLHL and VLHL$_{NS}$ are most likely in the active conformation despite one point mutation (R369A) that causes their differences in uPA inactivation.

6.23.3 TREATMENT OF HUMAN PROSTATE CANCER CELLS BY THE MODIFIED PAI-1 MOLECULES

In order to determine the effect of wild-type PAI-1 and the modified PAI-1 molecules on cancer cell proliferation, viability of LnCAP cells treated with wild-type PAI-1 and the modified PAI-1 molecules was measured. Four different forms of the modified PAI-1 molecules were used: VLHL and VLHL$_{NS}$ in the active conformation and VLHL and VLHL$_{NS}$ treated with DTT, which converted the VLHL and VLHL$_{NS}$ to the inactive conformation (DTT was removed by dialysis after treatment). As controls, appropriate buffer, hp-12-LOX as an inert protein and non-treated cells were used.

Promega's CellTiter assay showed a reduction of cell proliferation reaching 73% for LnCAP cells that are treated with VLHL and 58% for VLHL$_{NS}$ at the highest concentration. Also, inhibition of cell proliferation was concentration dependent but at lower concentrations, the data were not statistically significant. Different forms of the modified PAI-1 molecules also reduced cell viability as shown in Table 3; at the highest concentration, only ~80% of cells were viable. Thus, the modified PAI-1 molecules of the present invention may be used to reduce cancer cell proliferation.

TABLE 2

Viability of LnCAP cells treated with different forms of VLHL PAI-1s

| Cells treated with buffer or 100 µg/mL of PAI-1 | Viability in % |
|---|---|
| Control (buffer vs. non-treated) | 99.5 ± 0.4 |
| VLHL | 87.8 ± 0.5 |
| VLHL$_{NS}$ | 91.2 ± 2.5 |
| Latent VLHL (DTT treated) | 83.7 ± 3.8 |

All PAI-1-treated cells as early as 0.5-1 hour after addition of VLHL and VLHL$_{NS}$ start to detach from the surface of 96-well plates in the highest concentration. Later they start to aggregate, producing aggregates of several cells to several thousand cells in one cluster. FIG. 7 shows that human prostate cancer cell proliferation was observed in wells treated with wild type PAI-1 and the modified PAI-1 molecules. In subsequent experiments, detachment of cells and aggregation can be observed in concentrations of the modified PAI-1 molecules at or higher than 50 µg/mL of media. However, the morphology of the treated cells was altered below that value. LnCAP cells express very little uPA on the surface. Cells were detached after treated with PAI-1 in the active and latent conformation as well as by uPA-binding and non-uPA-binding PAI-1s. Furthermore, after detachment, the cells began to aggregate.

Cells that are treated with the modified PAI-1 molecules, VLHL and VLHL$_{NS}$, were harvested and ran on a SDS PAGE gel followed by Western Blot for the detection of ligands that bind to the modified PAI-1 molecules (e.g., vitronectin, LRP, uPAR, uPA or tPA) based on molecular weight and future LC-MS. Proteins that formed complexes with the modified PAI-1 molecules could be determined. On Western blot of control and treated samples, a thin band was observed at MW ~60 kDa. PAI-1 cannot bind to most of the known ligands and migrate in that region. The only ligand that is rarely reported in the literature is α-1-acid glycoprotein 2 precursor (Boncela et al. CS: Acute phase protein alpha 1-acid glycoprotein interacts with plasminogen activator inhibitor type 1 and stabilizes its inhibitory activity. *J. Biol. Chem.* 276:35305-35311, 2001). The combined molecular weight of this protein and the modified PAI-1 molecule could be detected in that region.

To analyze this phenomenon further, all three samples (VLHL, VLHL$_{NS}$ and control) were run on an SDS gel and the region corresponding to ~60+10 kDa was excised from the gel and analyzed on LC-MS. Several proteins have been identified, none of which are known PAI-1 ligands or a PAI-1 itself (Table 4).

TABLE 4

Proteins detected in ~60 kDa region

| Protein Accession Number | Protein Name | Theoretical MW kDa | Control | PAI-1 VLHL | PAI-1 VLHL$_{NS}$ |
|---|---|---|---|---|---|
| P04406 | GAPDH | 35.9 | − | − | + |
| P06576 | ATP synthase | 56.5 | + | + | + |
| P06733 | A-enolase | 47.0 | + | + | + |
| P07437 | Tubulin β-2 chain | 49.7 | + | − | − |
| P08418 | HSP70 | 69.9 | − | − | + |
| P27797 | Calregulin | 48.1 | + | + | + |
| P40926 | Malate dehydrogenase | 35.5 | − | + | − |
| P51648 | Aldehyde dehydrogenase | 54.8 | − | + | − |
| P60709 | B-actin | 41.7 | + | − | + |
| Q05639 | Elongation factor | 50.5 | + | + | + |
| Q13748 | A-tubulin 2 | 49.9 | + | − | + |
| Q15084 | Disulfide-isomerase | 48.1 | + | − | − |
| Q93081 | Histone | 15.3 | − | + | − |
| P04004 | Vitronectin | 54.3 | − | − | − |
| P00749 | uPA | 48.5 | − | − | − |
| P00750 | tPA | 62.9 | − | − | − |
| P05121 | PAI-1 | 45.0 | − | − | − |
| P19652 | α-1-acid glycoprotein 2 precursor | 23.6 | − | − | − |
| P30533 | Low density lipoprotein receptor | 41.5 | − | − | − |
| P10909 | Clusterin | 52.5 | − | − | − |
| Q03405 | CD87 | 37.0 | − | − | − |

+ Protein detected.
− Protein not detected.

6.23.4 ACIDIC WASH OF LnCAP CELLS TREATED WITH MODIFIED PAI-1 MOLECULES

In order to identify proteins that are associated with the modified PAI-1 molecules on the surface of the LnCAP cells. LnCAP cells that were treated with the modified PAI-1 molecules were washed with an acidic buffer to dissociate the complex formed between a protein and the modified PAI-1 molecule from the surface of LnCAP cells. As shown in FIG. 8, the protein gel showed a different pattern between control and PAI-1-treated cells. For cells treated with VLHL, two bands were observed in the ~40 kDa region, while for cells in control and treated VLHL$_{NS}$, these bands were in slightly different positions and in lesser amounts (bands 2 and 3 in FIG. 8). Based on LC-MS, these two bands contain several proteins, mainly bovine in origin and PAI-1. The signal from PAI-1 was strong; 5 to 9 peptides were identified in bands 2 and 3, respectively (Table 5). These could be endogenous active, latent or modified PAI-1 molecules. In the case of VLHL$_{NS}$, these bands were absent and LC-MS did not detect PAI-1, but some other proteins were detected, mostly bovine in origin. This shows that LnCAP cells bind modified PAI-1 molecules at the cell surface, most likely through uPA/uPAR and the LRP pathway.

TABLE 4

Proteins identified in acid wash of LnCAP cells treated with VLHL PAI-1s

| Protein Accession Number | Protein Name | Theoretical MW kDa | PAI-1 VLHL | PAI-1 VLHL$_{NS}$ |
|---|---|---|---|---|
| Band 1 | | | | |
| P34955 | A-1-antiprotease | 46.1 | ND | + |
| P02768 | BSA | 69.2 | ND | + |
| Q2KIF5 | Hypothetical | | ND | + |
| DQ452014 | IgG fragment | | ND | + |

TABLE 4-continued

Proteins identified in acid wash of LnCAP cells treated with VLHL PAI-1s

| Protein Accession Number | Protein Name | Theoretical MW kDa | PAI-1 VLHL | PAI-1 VLHL$_{NS}$ |
|---|---|---|---|---|
| P12763 | A-2-HS-protein | 38.5 | ND | + |
| Band 2 | | | | |
| P05121 | PAI-1 | 45.0 | + | − |
| P02769 | BSA | 69.3 | − | + |
| P04075 | Aldolase | 39.9 | + | − |
| P12763 | A-2-HS-protein | 38.5 | − | + |
| P34955 | Antitrypsin | 46.1 | − | + |
| Q5GN72 | A-acid glycoprotein | 33.5 | + | − |
| Q32PJ2 | Hypothetical | 21.7 | + | + |
| Q3SZR3 | Hypothetical | 43.0 | − | − |
| Band 3 | | | | |
| P05121 | PAI-1 | 45.0 | + | − |
| P02769 | BSA | 69.3 | − | + |
| P04406 | GAPDH | 35.9 | + | + |
| P00735 | Prothrombin | 70.5 | − | + |
| P12763 | A-2-HS-protein | 38.5 | − | + |
| Q5GN72 | A-acid glycoprotein | 21.7 | + | − |
| Q01105 | Protein SET | 33.5 | + | − |
| Q03247 | Apo-E | 36.0 | − | + |
| Q3SZR3 | Hypothetical | 43.3 | − | + |
| Q693V9 | C3d | 34.4 | − | + |

+ Protein detected.
− Protein not detected.
ND Not done.

SDS PAGE of the acid washed cells treated with VLHL$_{NS}$ also showed an additional band at ~130 kDa. This band was cut from the gel and analyzed by LC-MS. PAI-1, its ligands or complexes were not detected. All proteins detected were bovine in origin, some most likely dimerized (BSA) and some represented IgG fragments.

6.23.5 TWO DIMENSIONAL GEL ELECTROPHORESIS OF CELLS TREATED WITH DIFFERENT PAI-1s

Since only limited information could be derived from ID PAGE gels, VLHL PAI-1-treated LnCAP cells were analyzed by 2D PAGE. In a few places in the 2D gel of LnCAP cells treated with VLHL PAI-1, altered protein spots were detected. Cells treated with other forms of VLHL PAI-1 (inactive mutant or DTT treated PAI-1 converted into the latent form as well as wtPAI-1 that converts quickly into the latent form) produced virtually the same 2D gels with the exception of one spot. The detailed list is provided in Table 6 and protein spots are shown in FIG. 9.

Several proteins have been identified, but it seems that two of these are of importance in cancer. Both are downregulated; one in VLHL PM-1-treated cells, the other in all PAI-1-treated cells. Nucleophosmin (also known as NPM, nucleolar phosphoprotein B23, numatrin or nucleolar protein NO38) was detected in the typical region for this protein (~32 kDa) but in two different spots, which could be the phosphorylated and unphosphorylated forms of NPM (Grisendi et al., 2006, *Nat. Rev. Cancer* 6:493-505). Another downregulated protein was detected in second area in a much lower molecular weight (~20 kDa). All peptides detected by LC-MS from that region were in the proximity of the C-terminus of the NMP protein, suggesting that a truncated fragment of ~20 kDa contains part of the NPM C-terminus.

tumor progression (Grisendi et al., 2006, *Nat. Rev. Cancer* 6:493-505). It has been implicated that the main biological effects of nucleophosmin overexpression are increased cell growth, proliferation and the inhibition of apoptosis (Grisendi et al., 2006, *Nat. Rev. Cancer* 6:493-505). Nucleophosmin/ALK activates phosphatidylinositol 3-kinase (PI3K) and its downstream effector of the serine/threonine kinase (Akt) (Slupianek et al., 2001, *Cancer Res.* 61:2194-2199). Akt is a key regulator of cell survival events, which targets a number of different cytoplasmic proteins, resulting in inactivation of the proapoptotic pathway (Balsara et al., 2006, *J. Biol. Chem.* 281:22527-22536). Hyperactivation of Akt was observed in proliferating PAI-1$^{-/-}$ endothelial cells (EC). Also, exogenous PAI-1 diminished the levels of Akt, which is similar to the effect observed by us in the case of NPM. PAI-1 is a negative regulator of cell growth, exerting its effect on the Akt pathway and that the regulation of proliferation is dependent on its interaction with low-density lipoprotein receptor-related protein. Indeed, this event can depend on interaction with LRP, since changes in NPM levels were observed for PAI-1 that is able to bind to uPA and to form PAI-1/uPA/uPAR/LRP complexes.

The other protein attenuated after PAI-1 treatment and of importance in cancer is translationally controlled tumor protein (TCTP, also called p23, histamine-releasing factor-HRF or fortilin), MW 19.6 kDa species shown in Table 6 and FIG. 9. Contrary to NPM, this protein has been downregulated in all PAI-1-treated cells. TCTP is an anti-apoptotic protein, but

TABLE 6

Altered protein spots and their identified names as LNCaP cells were treated with different forms of PAI-1

| Protein Spot Number/ Protein Name | Protein Accession Number | VLHL PAI-1 | VLHL PAI-1 DTT | VLHL$_{NS}$ PAI-1 | wPAI-1 |
|---|---|---|---|---|---|
| Gel pI 4-7 | | | | | |
| 1. Nucleophosmin* | P06748 | ↓ | unaffected | unaffected | unaffected |
| 2. Nucleophosmin* | P06748 | ↓ | unaffected | unaffected | unaffected |
| 3. Peroxiredoxin-4, | Q13162 | ↓ | unaffected | unaffected | unaffected |
| Endopeptidase, | Q16740 | ↓ | unaffected | unaffected | unaffected |
| ATP12 Homolog | Q8N5M1 | ↓ | unaffected | unaffected | unaffected |
| 4. TCTP | P13693 | ↓ | ↓ | ↓ | ↓ |
| 5. Myosin RLC, | P19105 | ↓ | unaffected | unaffected | unaffected |
| DNA-directed RNA Polymerase II | O15514 | ↓ | unaffected | unaffected | unaffected |
| Gel pI 3-10 | | | | | |
| 6. Nucleophosmin*, ~20 kDa Fragment, | P06748 | ↓ | ND | ND | ND |
| Chromobox Protein Homolog 3 | Q13185 | ↓ | ND | ND | ND |
| 7. Nucleophosmin* ~20 kDa Fragment | P06748 | ↓ | ND | ND | ND |
| 8. RPLP1 Protein | Q6FG99 | ↓ | ND | ND | ND |

*Two spots of nucleophosmin have been identified, possibly unphosphorylated and phosphorylated form.
↓ Downregulated in comparison with control.
ND not done.

NPM is an abundant phosphoprotein that resides in nucleoli, although it shuttles rapidly between the nucleus and cytoplasm. NPM takes part in various cellular processes including the transport of pre-ribosomal particles and ribosome biogenesis, the response to stress stimuli such as UV irradiation and hypoxia and the DNA-repair processes. However, nucleophosmin is also overexpressed in a variety of cancers and it has been proposed as a marker for gastric, colon, ovarian and prostate malignancies. The level of its expression has been correlated in some cases with stages of is not related to the Bcl-2 family of proteins and protein inhibitors of apoptosis. The TCTP message is ubiquitous in normal tissues, but especially high in the liver, kidney and small intestine. Also, TCTP is elevated in cancerous cells compared to cell lines derived from normal tissue (Ii et al., 2006, *Exp. Biol. Med.* (Maywood) 231:20-27).

"Revertants" are cancer cells that were transformed with v-src (so called flat revertant factor) or chemically treated, which results in cells with decreased tumor-producing ability. By analyzing the gene expression profile between tumor cells and revertant counterparts, a significant downregulation of TCTP was found in the revertants (Ii et al., 2006, *Exp. Biol. Med.* (Maywood) 231:20-27; Tuynder et al., 2004, *Proc. Natl. Acad. Sci. USA* 101:15364-15369; Tuynder et al., 2002, *Proc. Natl. Acad. Sci. USA* 99:14976-14981). Furthermore, by transfecting cancer cells with antisense TCTP, the number of revertant cells was significantly increased (Tuynder et al., 2002, *Proc. Natl. Acad. Sci. USA* 99:14976-14981).

Collectively, these surprising and unexpected observations demonstrate that PAI-1 affect cells in diverse ways. PAI-1 may act as a negative regulator of cell proliferation and exert its effect on the NPM pathway, as well as in the independent TCTP pathway. The first one is most likely related to the nonproteolytic role of the uPAR/uPA/PAI-1/LRP complex, since both uPAR and LRP are involved in cellular signaling pathways (Zhang et al., 2004, *J. Am. Soc. Nephrol.* 15:2090-2102). The second described event is not related to uPAR/uPA/PAI-1/LRP complex formation as the inactive or latent forms of PAI-1 cannot bind to uPA.

6.24 STRUCTURAL ANALYSIS BETWEEN ACTIVE AND LATENT CONFORMATIONS OF PAI-1

During the conversion from the active to latent form, plasminogen activator inhibitor undergoes a substantial structural rearrangement. Since cell detachment and downregulation of TCTP were observed after treatment with wild-type PAI-1 or modified PAI-1 molecule regardless of its conformation or serin activity, the active and latent structures were analysed to find conserved regions of the PAI-1 molecule responsible for these events. Judging by the RMSD between the two different structures (1B3K, 1C5G), most conserved regions of PAI-1 are helices (hA, hB, hC, hD, hE, hH) and the loop between strand s1B and s2B. Thus, they constitute the most probable regions of PAI-1 responsible for the detachment of cells and downregulation of TCTP.

Treatment of LnCAP cells with various forms of PAI-1 shows that, first, the detachment of cells and their further aggregation and the downregulation of TCTP were unrelated to PAI-1 inhibitory capability or its latent or active conformation. These processes are driven by unknown mechanism(s) and in all probability involve a conserved part of the PAI-1 molecule. Second, downregulation of NPM was associated with active VLHL, suggesting a nonproteolytic function of the uPAR/uPA/PAI-1/LRP complex. Downregulation of NMP and TCTP by the modified PAI-1 molecules have not been reported and are novel observations that supplement anti-cancer activity of PAI-1.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties. Citations of references hereinabove shall not be construed as an admission that such references are prior art to the present invention.

---

What is claimed is:

1. A modified PAI-1 molecule comprising an active form, said modified PAI-1 molecule comprising a helix D region, an A3 strand, an A4 strand and an A5 strand, said molecule comprising an amino acid sequence which has at least about 90% identity to SEQ ID NO:2, said molecule comprises:
   (a) one or more pairs of amino acid residues not present in a corresponding wild-type PAI-1 protein wherein such one or more pairs of amino acid residues contain sulfhydryl groups, such that one or more disulfide bridges form between or within said helix D region, A3 strand, A4 strand and/or A5 strand of said modified PAI-1 molecule; and
   (b) one or more amino acid substitutions relative to the amino acid sequence of SEQ ID NO:2 at positions selected from the group consisting of: 146, 197, 352, 355 and 369, wherein the active form of said modified PAI-1 molecule displays:
   (i) a longer in vivo half-life; and
   (ii) one or more decreased of the following characteristics: (1) decreased binding activity to at least one of the following molecules: urokinase plasminogen activator (uPA), tissue plasminogen activator (tPA) and vitronectin (Vn); and (2) decreased specific activity against one of the following molecules: uPA, tPA and Vn, as compared to the active form of a corresponding wild-type PAI-1 protein.

2. The modified PAI-1 molecule of claim 1 wherein the one or more pairs of amino acid substitution are at positions:
   (i) 197, 355 and 369,
   (ii) 197, 355 and 146,
   (iii) 197, 355 and 352,
   (iv) 197, 355, 369 and 146,
   (iv) 197, 355, 369 and 352,
   (vi) 197, 355, 369, 146 and 352; and/or
   (vii) 197, 355 and 146,
   of the amino acid sequence of said wild-type PAI-1 protein using SEQ ID NO: 2 for numbering.

3. The modified PAI-1 molecule of claim 1 wherein the one or more amino acid substitutions are at amino acid positions of said wild-type PAI-1 protein using SEQ ID NO:2 for numbering, such amino acid substitutions are:

(i) Gln 146 substituted with amino acid residue Asn, Lys, Arg or His;
   (ii) Asn 352 substituted with amino acid residue Ala, Pro, Gly or Ser;
   (iii) Arg 369 substituted with amino acid residue Ala, Pro, Gly or Ser;
   (iv) Gln 197 substituted with amino acid residue Cys; and/or
   (v) Gly 355 substituted with amino acid residue Cys.

4. The modified PAI-1 molecule of claim 1 wherein said residue that contains a sulfhydryl group is cysteine.

5. The modified PAI-1 molecule of claim 1 wherein said functional activity is binding or inhibition of uPA, tPA or Vn.

6. The modified PAI-1 molecule of claim 1 wherein said functional activity comprises specific activity against Vn.

7. The modified PAI-1 molecule of claim 3 wherein said molecule is $VLHL_{NS}$, $VLHL_{NV}$, $VLHL_{NT}$, $VLHL_{NS, NV}$, $VLHL_{NS, NT}$, $VLHL_{NV, NT}$, or $VLHL_{NS, NV, NT}$.

8. A method of treating cancer, cardiovascular disease or a proliferative disease in a subject suffering therefrom, said method comprising administering the modified PAI-1 molecule of claim 1 to said subject.

9. The method of claim 8 wherein said cancer is selected from the group consisting of breast cancer, colon cancer, ovarian cancer, lung cancer, prostate cancer, melanoma, leukemia, skin cancer, pancreatic cancer, bladder cancer, sarcoma, and uterine cancer.

10. The modified PAI-1 molecule of claim 1 wherein said disulfide bridges comprise a bridge located at the Cys 197 and 355 positions of the amino acid sequence of said wild-type PAI-1 protein using SEQ ID NO: 2 for numbering.

11. The modified PAI-1 molecule of claim 1 wherein said amino acid sequence has at least about 95% or 98% identity to SEQ ID NO: 2.

12. A modified PAI-1 molecule of claim 1, comprising the amino acid sequence of SEQ ID NO:5, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 or SEQ ID NO:20.

* * * * *

SEQUENCE LISTING

```
<160> NUMBER OF SEQ ID NOS: 38

<210> SEQ ID NO 1
<211> LENGTH: 2876
<212> TYPE: DNA
<213> ORGANISM: Home sapiens
<220> FEATURE:
<221> NAME/KEY: CDS
<222> LOCATION: (76)...(1281)
<223> OTHER INFORMATION: human PAI-1 plus 5' and 3' sequence

<400> SEQUENCE: 1
gaattcctgc agctcagcag ccgccgccag agcaggacga accgccaatc gcaaggcacc     60
tctgagaact tcagg atg cag atg tct cca gcc ctc acc tgc cta gtc ctg    111
              Met Gln Met Ser Pro Ala Leu Thr Cys Leu Val Leu
                1               5                  10 ggc ctg gcc ctt gtc ttt ggt gaa ggg tct gct gtg cac cat ccc cca     159
Gly Leu Ala Leu Val Phe Gly Glu Gly Ser Ala Val His His Pro Pro
         15                  20                  25 tcc tac gtg gcc cac ctg gcc tca gac ttc ggg gtg agg gtg ttt cag     207
Ser Tyr Val Ala His Leu Ala Ser Asp Phe Gly Val Arg Val Phe Gln
     30                  35                  40 cag gtg gcg cag gcc tcc aag gac cgc aac gtg gtt ttc tca ccc tat     255
Gln Val Ala Gln Ala Ser Lys Asp Arg Asn Val Val Phe Ser Pro Tyr
 45                  50                  55                  60 ggg gtg gcc tcg gtg ttg gcc atg ctc cag ctg aca aca gga gga gaa     303
Gly Val Ala Ser Val Leu Ala Met Leu Gln Leu Thr Thr Gly Gly Glu
                 65                  70                  75 acc cag cag cag att caa gca gct atg gga ttc aag att gac gac aag     351
Thr Gln Gln Gln Ile Gln Ala Ala Met Gly Phe Lys Ile Asp Asp Lys
```

-continued

```
                  80                      85                      90
ggc atg gcc ccc gcc ctc cgg cat ctg tac aag gag ctc atg ggg cca      399
Gly Met Ala Pro Ala Leu Arg His Leu Tyr Lys Glu Leu Met Gly Pro
         95                     100                     105 tgg aac aag gat gag atc agc acc aca gac gcg atc ttc gtc cag cgg      447
Trp Asn Lys Asp Glu Ile Ser Thr Thr Asp Ala Ile Phe Val Gln Arg
110                     115                     120 gat ctg aag ctg gtc cag ggc ttc atg ccc cac ttc ttc agg ctg ttc      495
Asp Leu Lys Leu Val Gln Gly Phe Met Pro His Phe Phe Arg Leu Phe
    125                     130                     135                 140 cgg agc acg gtc aag caa gtg gac ttt tca gag gtg gag aga gcc aga      543
Arg Ser Thr Val Lys Gln Val Asp Phe Ser Glu Val Glu Arg Ala Arg
                145                     150                     155 ttc atc atc aat gac tgg gtg aag aca cac aca aaa ggt atg atc agc      591
Phe Ile Ile Asn Asp Trp Val Lys Thr His Thr Lys Gly Met Ile Ser
                160                     165                     170 aac ttg ctt ggg aaa gga gcc gtg gac cag ctg aca cgg ctg gtg ctg      639
Asn Leu Leu Gly Lys Gly Ala Val Asp Gln Leu Thr Arg Leu Val Leu
            175                     180                     185 gtg aat gcc ctc tac ttc aac ggc cag tgg aag act ccc ttc ccc gac      687
Val Asn Ala Leu Tyr Phe Asn Gly Gln Trp Lys Thr Pro Phe Pro Asp
        190                     195                     200 tcc agc acc cac cgc cgc ctc ttc cac aaa tca gac ggc agc act gtc      735
Ser Ser Thr His Arg Arg Leu Phe His Lys Ser Asp Gly Ser Thr Val
205                     210                     215                     220 tct gtg ccc atg atg gct cag acc aac aag ttc aac tat act gag ttc      783
Ser Val Pro Met Met Ala Gln Thr Asn Lys Phe Asn Tyr Thr Glu Phe
                    225                     230                     235 acc acg ccc gat ggc cat tac tac gac atc ctg gaa ctg ccc tac cac      831
Thr Thr Pro Asp Gly His Tyr Tyr Asp Ile Leu Glu Leu Pro Tyr His
            240                     245                     250 ggg gac acc ctc agc atg ttc att gct gcc cct tat gaa aaa gag gtg      879
Gly Asp Thr Leu Ser Met Phe Ile Ala Ala Pro Tyr Glu Lys Glu Val
        255                     260                     265 cct ctc tct gcc ctc acc aac att ctg agt gcc cag ctc atc agc cac      927
Pro Leu Ser Ala Leu Thr Asn Ile Leu Ser Ala Gln Leu Ile Ser His
270                     275                     280 tgg aaa ggc aac atg acc agg ctg ccc cgc ctc ctg gtt ctg ccc aag      975
Trp Lys Gly Asn Met Thr Arg Leu Pro Arg Leu Leu Val Leu Pro Lys
285                     290                     295                     300 ttc tcc ctg gag act gaa gtc gac ctc agg aag ccc cta gag aac ctg     1023
Phe Ser Leu Glu Thr Glu Val Asp Leu Arg Lys Pro Leu Glu Asn Leu
                    305                     310                     315 gga atg acc gac atg ttc aga cag ttt cag gct gac ttc acg agt ctt     1071
Gly Met Thr Asp Met Phe Arg Gln Phe Gln Ala Asp Phe Thr Ser Leu
                320                     325                     330 tca gac caa gag cct ctc cac gtc gcg cag gcg ctg cag aaa gtg aag     1119
Ser Asp Gln Glu Pro Leu His Val Ala Gln Ala Leu Gln Lys Val Lys
            335                     340                     345 atc gag gtg aac gag agt ggc acg gtg gcc tcc tca tcc aca gct gtc     1167
Ile Glu Val Asn Glu Ser Gly Thr Val Ala Ser Ser Ser Thr Ala Val
        350                     355                     360 ata gtc tca gcc cgc atg gcc ccc gag gag atc atc atg gac aga ccc     1215
Ile Val Ser Ala Arg Met Ala Pro Glu Glu Ile Ile Met Asp Arg Pro
365                     370                     375                     380 ttc ctc ttt gtg gtc cgg cac aac ccc aca gga aca gtc ctt ttc atg     1263
Phe Leu Phe Val Val Arg His Asn Pro Thr Gly Thr Val Leu Phe Met
                    385                     390                     395 ggc caa gtg atg gaa ccc tgaccctggg gaaagacgcc ttcatctggg            1311
Gly Gln Val Met Glu Pro
```

-continued

```
                400
acaaaactgg agatgcatcg ggaaagaaga aactccgaag aaaagaattt tagtgttaat    1371
gactctttct gaaggaagag aagacatttg cctttttgtta aaagatggta aaccagatct   1431
gtctccaaga ccttggcctc tccttggagg acctttaggt caaactccct agtctccacc    1491
tgagaccctg ggagagaagt ttgaagcaca actcccttaa ggtctccaaa ccagacggtg    1551
acgcctgcgg gaccatctgg ggcacctgct tccacccgtc tctctgccca ctcgggtctg    1611
cagacctggt tcccactgag gcccttttgca ggatggaact acggggctta caggagcttt   1671
tgtgtgcctg gtagaaacta tttctgttcc agtcacattg ccatcactct tgtactgcct    1731
gccaccgcgg aggaggctgg tgacaggcca aaggccagtg aagaaacac cctttcatct     1791 cagagtccac tgtggcactg ccacccctc cccagtacag gggtgctgca ggtggcagag     1851
tgaatgtccc ccatcatgtg gcccaactct cctggcctgg ccatctccct ccccagaaac    1911
agtgtgcatg ggtatttttg gagtgtaggt gacttgttta ctcattgaag cagatttctg    1971 cttccttttta tttttatagg aatagaggaa gaaatgtcag atgcgtgccc agctcttcac   2031
cccccaatct cttggtgggg agggtgtac ctaaatattt atcatatcct tgccccttgag    2091 tgcttgttag agagaaagag aactactaag gaaaataata ttatttaaac tcgctcctag    2151
tgtttctttg tggtctgtgt caccgtatct caggaagtcc agccacttga ctggcacaca    2211
cccctccgga catccagcgt gacggagccc acactgccac cttgtggccg cctgagaccc    2271
tcgcgccccc cgcgcccccc gcgccctct ttttcccctt gatggaaatt gaccatacaa     2331
tttcatcctc cttcagggga tcaaaaggac ggagtgggg gacagagact cagatgagga     2391
cagagtggtt tccaatgtgt tcaatagatt taggagcaga aatgcaaggg gctgcatgac    2451
ctaccaggac agaactttcc ccaattacag ggtgactcac agccgcattg gtgactcact    2511
tcaatgtgtc atttccggct gctgtgtgtg agcagtggac acgtgagggg ggggtgggtg    2571
agagagacag gcagctcgga ttcaactacc ttagataata tttctgaaaa cctaccagcc    2631
agagggtagg gcacaaagat ggatgtaatg cactttggga ggccaaggcg ggaggattgc    2691
ttgagcccag gagttcaaga ccagcctggg caacatacca agaccccgt ctcttttaaaa    2751 atatatatat tttaaatata cttaaatata tatttctaat atctttaaat atatatatat    2811 atttaaaga ccaattatg ggagaattgc acacagatgt gaaatgaatg taatctaata      2871
gaagc                                                                2876
```

<210> SEQ ID NO 2
<211> LENGTH: 402
<212> TYPE: PRT
<213> ORGANISM: Home sapiens
<220> FEATURE:
<223> OTHER INFORMATION: human PAI-1 amino acid sequence, including signal peptide

<400> SEQUENCE: 2

Met Gln Met Ser Pro Ala Leu Thr Cys Leu Val Leu Gly Leu Ala Leu
 1               5                  10                  15

Val Phe Gly Glu Gly Ser Ala Val His His Pro Ser Tyr Val Ala
                20                  25                  30

His Leu Ala Ser Asp Phe Gly Val Arg Val Phe Gln Gln Val Ala Gln
            35                  40                  45

Ala Ser Lys Asp Arg Asn Val Val Phe Ser Pro Tyr Gly Val Ala Ser
        50                  55                  60

Val Leu Ala Met Leu Gln Leu Thr Thr Gly Gly Glu Thr Gln Gln Gln

Ile Gln Ala Ala Met Gly Phe Lys Ile Asp Asp Lys Gly Met Ala Pro
65                  70                  75                  80

Ala Leu Arg His Leu Tyr Lys Glu Leu Met Gly Pro Trp Asn Lys Asp
            85                  90                  95

Glu Ile Ser Thr Thr Asp Ala Ile Phe Val Gln Arg Asp Leu Lys Leu
        100                 105                 110

Val Gln Gly Phe Met Pro His Phe Phe Arg Leu Phe Arg Ser Thr Val
    115                 120                 125

Lys Gln Val Asp Phe Ser Glu Val Glu Arg Ala Arg Phe Ile Ile Asn
130                 135                 140

Asp Trp Val Lys Thr His Thr Lys Gly Met Ile Ser Asn Leu Leu Gly
145                 150                 155                 160

Lys Gly Ala Val Asp Gln Leu Thr Arg Leu Val Leu Val Asn Ala Leu
            165                 170                 175

Tyr Phe Asn Gly Gln Trp Lys Thr Pro Phe Pro Asp Ser Ser Thr His
        180                 185                 190

Arg Arg Leu Phe His Lys Ser Asp Gly Ser Thr Val Ser Val Pro Met
    195                 200                 205

Met Ala Gln Thr Asn Lys Phe Asn Tyr Thr Glu Phe Thr Thr Pro Asp
210                 215                 220

Gly His Tyr Tyr Asp Ile Leu Glu Leu Pro Tyr His Gly Asp Thr Leu
225                 230                 235                 240

Ser Met Phe Ile Ala Ala Pro Tyr Glu Lys Glu Val Pro Leu Ser Ala
            245                 250                 255

Leu Thr Asn Ile Leu Ser Ala Gln Leu Ile Ser His Trp Lys Gly Asn
        260                 265                 270

Met Thr Arg Leu Pro Arg Leu Leu Val Leu Pro Lys Phe Ser Leu Glu
    275                 280                 285

Thr Glu Val Asp Leu Arg Lys Pro Leu Glu Asn Leu Gly Met Thr Asp
290                 295                 300

Met Phe Arg Gln Phe Gln Ala Asp Phe Thr Ser Leu Ser Asp Gln Glu
305                 310                 315                 320

Pro Leu His Val Ala Gln Ala Leu Gln Lys Val Lys Ile Glu Val Asn
            325                 330                 335

Glu Ser Gly Thr Val Ala Ser Ser Thr Ala Val Ile Val Ser Ala
        340                 345                 350

Arg Met Ala Pro Glu Glu Ile Ile Met Asp Arg Pro Phe Leu Phe Val
    355                 360                 365

Val Arg His Asn Pro Thr Gly Thr Val Leu Phe Met Gly Gln Val Met
370                 375                 380

Glu Pro
385

<210> SEQ ID NO 3
<211> LENGTH: 379
<212> TYPE: PRT
<213> ORGANISM: Home sapiens
<220> FEATURE:
<223> OTHER INFORMATION: human PAI-1 mature amino acid sequence

<400> SEQUENCE: 3

Val His His Pro Pro Ser Tyr Val Ala His Leu Ala Ser Asp Phe Gly
1               5                   10                  15

Val Arg Val Phe Gln Gln Val Ala Gln Ala Ser Lys Asp Arg Asn Val
            20                  25                  30

```
Val Phe Ser Pro Tyr Gly Val Ala Ser Val Leu Ala Met Leu Gln Leu
         35                  40                  45

Thr Thr Gly Gly Glu Thr Gln Gln Ile Gln Ala Ala Met Gly Phe
 50                  55                  60

Lys Ile Asp Asp Lys Gly Met Ala Pro Ala Leu Arg His Leu Tyr Lys
 65                  70                  75                  80

Glu Leu Met Gly Pro Trp Asn Lys Asp Glu Ile Ser Thr Thr Asp Ala
                 85                  90                  95

Ile Phe Val Gln Arg Asp Leu Lys Leu Val Gln Gly Phe Met Pro His
                100                 105                 110

Phe Phe Arg Leu Phe Arg Ser Thr Val Lys Gln Val Asp Phe Ser Glu
            115                 120                 125

Val Glu Arg Ala Arg Phe Ile Ile Asn Asp Trp Val Lys Thr His Thr
130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Gln Trp Lys
                165                 170                 175

Thr Pro Phe Pro Asp Ser Ser Thr His Arg Arg Leu Phe His Lys Ser
            180                 185                 190

Asp Gly Ser Thr Val Ser Val Pro Met Met Ala Gln Thr Asn Lys Phe
        195                 200                 205

Asn Tyr Thr Glu Phe Thr Thr Pro Asp Gly His Tyr Tyr Asp Ile Leu
    210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
                245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
        275                 280                 285

Pro Leu Glu Asn Leu Gly Met Thr Asp Met Phe Arg Gln Phe Gln Ala
    290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Gly Thr Val Ala Ser
                325                 330                 335

Ser Ser Thr Ala Val Ile Val Ser Ala Arg Met Ala Pro Glu Glu Ile
            340                 345                 350

Ile Met Asp Arg Pro Phe Leu Phe Val Val Arg His Asn Pro Thr Gly
        355                 360                 365

Thr Val Leu Phe Met Gly Gln Val Met Glu Pro
    370                 375

<210> SEQ ID NO 4
<211> LENGTH: 406
<212> TYPE: PRT
<213> ORGANISM: homo sapiens
<220> FEATURE:
<223> OTHER INFORMATION: VLHL sequence

<400> SEQUENCE: 4

Met His His His His His Asp Tyr Asp Ile Pro Thr Thr Glu Asn
 1               5                  10                  15

Leu Tyr Phe Gln Gly Ala Met Asp Pro Glu Phe Val His His Pro Pro
```

-continued

```
                20                  25                  30
Ser Tyr Val Ala His Leu Ala Ser Asp Phe Gly Val Arg Val Phe Gln
            35                  40                  45
Gln Val Ala Gln Ala Ser Lys Asp Arg Asn Val Val Phe Ser Pro Tyr
 50                  55                  60
Gly Val Ala Ser Val Leu Ala Met Leu Gln Leu Thr Thr Gly Gly Glu
 65                  70                  75                  80
Thr Gln Gln Gln Ile Gln Ala Ala Met Gly Phe Lys Ile Asp Asp Lys
                85                  90                  95
Gly Met Ala Pro Ala Leu Arg His Leu Tyr Lys Glu Leu Met Gly Pro
                100                 105                 110
Trp Asn Lys Asp Glu Ile Ser Thr Thr Asp Ala Ile Phe Val Gln Arg
                115                 120                 125
Asp Leu Lys Leu Val Gln Gly Phe Met Pro His Phe Phe Arg Leu Phe
                130                 135                 140
Arg Ser Thr Val Lys Gln Val Asp Phe Ser Glu Val Glu Arg Ala Arg
145                 150                 155                 160
Phe Ile Ile Asn Asp Trp Val Lys Thr His Thr Lys Gly Met Ile Ser
                165                 170                 175
Asn Leu Leu Gly Lys Gly Ala Val Asp Gln Leu Thr Arg Leu Val Leu
                180                 185                 190
Val Asn Ala Leu Tyr Phe Asn Gly Cys Trp Lys Thr Pro Phe Pro Asp
                195                 200                 205
Ser Ser Thr His Arg Arg Leu Phe His Lys Ser Asp Gly Ser Thr Val
                210                 215                 220
Ser Val Pro Met Met Ala Gln Thr Asn Lys Phe Asn Tyr Thr Glu Phe
225                 230                 235                 240
Thr Thr Pro Asp Gly His Tyr Tyr Asp Ile Leu Glu Leu Pro Tyr His
                245                 250                 255
Gly Asp Thr Leu Ser Met Phe Ile Ala Ala Pro Tyr Glu Lys Glu Val
                260                 265                 270
Pro Leu Ser Ala Leu Thr Asn Ile Leu Ser Ala Gln Leu Ile Ser His
                275                 280                 285
Trp Lys Gly Asn Met Thr Arg Leu Pro Arg Leu Leu Val Leu Pro Lys
                290                 295                 300
Phe Ser Leu Glu Thr Glu Val Asp Leu Arg Lys Pro Leu Glu Asn Leu
305                 310                 315                 320
Gly Met Thr Asp Met Phe Arg Gln Phe Gln Ala Asp Phe Thr Ser Leu
                325                 330                 335
Ser Asp Gln Glu Pro Leu His Val Ala Gln Ala Leu Gln Lys Val Lys
                340                 345                 350
Ile Glu Val Asn Glu Ser Cys Thr Val Ala Ser Ser Ser Thr Ala Val
                355                 360                 365
Ile Val Ser Ala Arg Met Ala Pro Glu Glu Ile Ile Met Asp Arg Pro
                370                 375                 380
Phe Leu Phe Val Val Arg His Asn Pro Thr Gly Thr Val Leu Phe Met
385                 390                 395                 400
Gly Gln Val Met Glu Pro
                405

<210> SEQ ID NO 5
<211> LENGTH: 406
<212> TYPE: PRT
<213> ORGANISM: homo sapiens
<220> FEATURE:
```

<223> OTHER INFORMATION: VLHL-NS sequence

<400> SEQUENCE: 5

```
Met His His His His His

<210> SEQ ID NO 6
<211> LENGTH: 379
<212> TYPE: PRT
<213> ORGANISM: homo sapiens
<220> FEATURE:
<223> OTHER INFORMATION: 1B3K sequence

<400> SEQUENCE: 6

```
Val His His Pro Pro Ser Tyr Val Ala His Leu Ala Ser Asp Phe Gly
                 5                  10                  15
Val Arg Val Phe Gln Gln Val Ala Gln Ala Ser Lys Asp Arg Asn Val
             20                  25                  30
Val Phe Ser Pro Tyr Gly Val Ala Ser Val Leu Ala Met Leu Gln Leu
         35                  40                  45
Thr Thr Gly Gly Glu Thr Gln Gln Ile Gln Ala Ala Met Gly Phe
     50                  55                  60
Lys Ile Asp Asp Lys Gly Met Ala Pro Ala Leu Arg His Leu Tyr Lys
 65                  70                  75                  80
Glu Leu Met Gly Pro Trp Asn Lys Asp Glu Ile Ser Thr Thr Asp Ala
                 85                  90                  95
Ile Phe Val Gln Arg Asp Leu Lys Leu Val Gln Gly Phe Met Pro His
            100                 105                 110
Phe Phe Arg Leu Phe Arg Ser Thr Val Lys Gln Val Asp Phe Ser Glu
        115                 120                 125
Val Glu Arg Ala Arg Phe Ile Ile Asn Asp Trp Val Lys Thr His Thr
    130                 135                 140
Lys Gly Met Ile Ser His Leu Leu Gly Thr Gly Ala Val Asp Gln Leu
145                 150                 155                 160
Thr Arg Leu Val Leu Val Asn Ala Leu Tyr Phe Asn Gly Gln Trp Lys
                165                 170                 175
Thr Pro Phe Pro Asp Ser Ser Thr His Arg Arg Leu Phe His Lys Ser
            180                 185                 190
Asp Gly Ser Thr Val Ser Val Pro Met Met Ala Gln Thr Asn Lys Phe
        195                 200                 205
Asn Tyr Thr Glu Phe Thr Thr Pro Asp Gly His Tyr Tyr Asp Ile Leu
    210                 215                 220
Glu Leu Pro Tyr His Gly Asp Thr Leu Ser Met Phe Ile Ala Ala Pro
225                 230                 235                 240
Tyr Glu Lys Glu Val Pro Leu Ser Ala Leu Thr Asn Ile Leu Ser Ala
                245                 250                 255
Gln Leu Ile Ser His Trp Lys Gly Asn Met Thr Arg Leu Pro Arg Leu
            260                 265                 270
Leu Val Leu Pro Lys Phe Ser Leu Glu Thr Glu Val Asp Leu Arg Lys
        275                 280                 285
Pro Leu Glu Asn Leu Gly Met Thr Asp Met Phe Arg Gln Phe Gln Ala
    290                 295                 300
Asp Phe Thr Ser Leu Ser Asp Gln Glu Pro Leu His Val Ala Leu Ala
305                 310                 315                 320
Leu Gln Lys Val Lys Ile Glu Val Asn Glu Ser Gly Thr Val Ala Ser
                325                 330                 335
Ser Ser Thr Ala Val Ile Val Ser Ala Arg Met Ala Pro Glu Glu Ile
            340                 345                 350
Ile Ile Asp Arg Pro Phe Leu Phe Val Val Arg His Asn Pro Thr Gly
        355                 360                 365
```

```
Thr Val Leu Phe Met Gly Gln Val Met Glu Pro
    370                 375
```

<210> SEQ ID NO 7
<211> LENGTH: 351
<212> TYPE: PRT
<213> ORGANISM: homo sapiens
<220> FEATURE:
<223> OTHER INFORMATION: mini-VLHL sequence

<400> SEQUENCE: 7

```
Met His His His His His Asp Tyr Asp Ile Pro Thr Thr Glu Asn
  1               5                  10                  15

Leu Tyr Phe Gln Gly Ala Met Asp Pro Glu Phe Val His His Pro Pro
             20                  25                  30

Ser Tyr Val Ala His Leu Ala Ser Asp Phe Gly Val Arg Val Phe Gln
             35                  40                  45

Gln Val Ala Gln Ala Ser Lys Asp Arg Asn Val Val Phe Ser Pro Tyr
         50                  55                  60

Gly Val Ala Ser Val Leu Ala Met Leu Gln Leu Thr Thr Gly Gly Glu
 65                  70                  75                  80

Thr Gln Gln Gln Ile Gln Ala Ala Met Gly Phe Lys Ile Asp Asp Lys
             85                  90                  95

Gly Met Ala Pro Ala Leu Arg His Leu Tyr Lys Glu Leu Met Gly Pro
            100                 105                 110

Trp Asn Lys Asp Glu Ile Ser Thr Thr Asp Ala Ile Phe Val Gln Arg
            115                 120                 125

Asp Leu Gln Leu Thr Arg Leu Val Leu Val Asn Ala Leu Tyr Phe Asn
        130                 135                 140

Gly Cys Trp Lys Thr Pro Phe Pro Asp Ser Ser Thr His Arg Arg Leu
145                 150                 155                 160

Phe His Lys Ser Asp Gly Ser Thr Val Ser Val Pro Met Met Ala Gln
            165                 170                 175

Thr Asn Lys Phe Asn Tyr Thr Glu Phe Thr Thr Pro Asp Gly His Tyr
            180                 185                 190

Tyr Asp Ile Leu Glu Leu Pro Tyr His Gly Asp Thr Leu Ser Met Phe
        195                 200                 205

Ile Ala Ala Pro Tyr Glu Lys Glu Val Pro Leu Ser Ala Leu Thr Asn
210                 215                 220

Ile Leu Ser Ala Gln Leu Ile Ser His Trp Lys Gly Asn Met Thr Arg
225                 230                 235                 240

Leu Pro Arg Leu Leu Val Leu Pro Lys Phe Ser Leu Glu Thr Glu Val
            245                 250                 255

Asp Leu Arg Lys Pro Leu Glu Asn Leu Gly Met Thr Asp Met Phe Arg
        260                 265                 270

Gln Phe Gln Ala Asp Phe Thr Ser Leu Ser Asp Gln Glu Pro Leu His
        275                 280                 285

Val Ala Gln Ala Leu Gln Lys Val Lys Ile Glu Val Asn Glu Ser Cys
        290                 295                 300

Thr Val Ala Ser Ser Ser Thr Ala Val Ile Val Ser Ala Arg Met Ala
305                 310                 315                 320

Pro Glu Glu Ile Ile Met Asp Arg Pro Phe Leu Phe Val Val Arg His
            325                 330                 335

Asn Pro Thr Gly Thr Val Leu Phe Met Gly Gln Val Met Glu Pro
            340                 345                 350
```

<210> SEQ ID NO 8
<211> LENGTH: 20
<212> TYPE: PRT
<213> ORGANISM: homo sapiens
<220> FEATURE:
<223> OTHER INFORMATION: linker sequence

<400> SEQUENCE: 8

Asp Tyr Asp Ile Pro Thr Thr Glu Asn Leu Tyr Phe Gln Gly Ala Met
1               5                   10                  15

Asp Pro Glu Phe
            20

<210> SEQ ID NO 9
<211> LENGTH: 23
<212> TYPE: PRT
<213> ORGANISM: homo sapiens
<220> FEATURE:
<223> OTHER INFORMATION: header sequence of human PAI-1

<400> SEQUENCE: 9

Met Gln Met Ser Pro Ala Leu Thr Cys Leu Val Leu Gly Leu Ala Leu
1               5                   10                  15

Val Phe Gly Glu Gly Ser Ala
            20

<210> SEQ ID NO 10
<211> LENGTH: 379
<212> TYPE: PRT
<213> ORGANISM: homo sapiens
<220> FEATURE:
<223> OTHER INFORMATION: VLHL without header sequence (aa 1-23)

<400> SEQUENCE: 10

Val His His Pro Pro Ser Tyr Val Ala His Leu Ala Ser Asp Phe Gly
1               5                   10                  15

Val Arg Val Phe Gln Gln Val Ala Gln Ala Ser Lys Asp Arg Asn Val
            20                  25                  30

Val Phe Ser Pro Tyr Gly Val Ala Ser Val Leu Ala Met Leu Gln Leu
        35                  40                  45

Thr Thr Gly Gly Glu Thr Gln Gln Gln Ile Gln Ala Ala Met Gly Phe
    50                  55                  60

Lys Ile Asp Asp Lys Gly Met Ala Pro Ala Leu Arg His Leu Tyr Lys
65                  70                  75                  80

Glu Leu Met Gly Pro Trp Asn Lys Asp Glu Ile Ser Thr Thr Asp Ala
                85                  90                  95

Ile Phe Val Gln Arg Asp Leu Lys Leu Val Gln Gly Phe Met Pro His
            100                 105                 110

Phe Phe Arg Leu Phe Arg Ser Thr Val Lys Gln Val Asp Phe Ser Glu
        115                 120                 125

Val Glu Arg Ala Arg Phe Ile Ile Asn Asp Trp Val Lys Thr His Thr
    130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Cys Trp Lys
                165                 170                 175

Thr Pro Phe Pro Asp Ser Ser Thr His Arg Arg Leu Phe His Lys Ser
            180                 185                 190

Asp Gly Ser Thr Val Ser Val Pro Met Met Ala Gln Thr Asn Lys Phe
        195                 200                 205

```
Asn Tyr Thr Glu Phe Thr Thr Pro Asp Gly His Tyr Tyr Asp Ile Leu
    210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
                245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
        275                 280                 285

Pro Leu Glu Asn Leu Gly Met Thr Asp Met Phe Arg Gln Phe Gln Ala
    290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Cys Thr Val Ala Ser
                325                 330                 335

Ser Ser Thr Ala Val Ile Val Ser Ala Arg Met Ala Pro Glu Glu Ile
            340                 345                 350

Ile Met Asp Arg Pro Phe Leu Phe Val Val Arg His Asn Pro Thr Gly
        355                 360                 365

Thr Val Leu Phe Met Gly Gln Val Met Glu Pro
    370                 375
```

<210> SEQ ID NO 11
<211> LENGTH: 379
<212> TYPE: PRT
<213> ORGANISM: homo sapiens
<220> FEATURE:
<223> OTHER INFORMATION: VLHL-NS without header sequence (aa 1-23)

<400> SEQUENCE: 11

```
Val His His Pro Pro Ser Tyr Val Ala His Leu Ala Ser Asp Phe Gly
  1               5                  10                  15

Val Arg Val Phe Gln Gln Val Ala Gln Ala Ser Lys Asp Arg Asn Val
                20                  25                  30

Val Phe Ser Pro Tyr Gly Val Ala Ser Val Leu Ala Met Leu Gln Leu
            35                  40                  45

Thr Thr Gly Gly Glu Thr Gln Gln Ile Gln Ala Ala Met Gly Phe
 50                  55                  60

Lys Ile Asp Asp Lys Gly Met Ala Pro Ala Leu Arg His Leu Tyr Lys
65                  70                  75                  80

Glu Leu Met Gly Pro Trp Asn Lys Asp Glu Ile Ser Thr Thr Asp Ala
                85                  90                  95

Ile Phe Val Gln Arg Asp Leu Lys Leu Val Gln Gly Phe Met Pro His
            100                 105                 110

Phe Phe Arg Leu Phe Arg Ser Thr Val Lys Gln Val Asp Phe Ser Glu
        115                 120                 125

Val Glu Arg Ala Arg Phe Ile Ile Asn Asp Trp Val Lys Thr His Thr
    130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Cys Trp Lys
                165                 170                 175

Thr Pro Phe Pro Asp Ser Ser Thr His Arg Arg Leu Phe His Lys Ser
            180                 185                 190
```

```
Asp Gly Ser Thr Val Ser Val Pro Met Met Ala Gln Thr Asn Lys Phe
            195                 200                 205

Asn Tyr Thr Glu Phe Thr Thr Pro Asp Gly His Tyr Tyr Asp Ile Leu
            210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
            245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
            275                 280                 285

Pro Leu Glu Asn Leu Gly Met Thr Asp Met Phe Arg Gln Phe Gln Ala
290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Cys Thr Val Ala Ser
            325                 330                 335

Ser Ser Thr Ala Val Ile Val Ser Ala Ala Met Ala Pro Glu Glu Ile
            340                 345                 350

Ile Asp Arg Pro Met Phe Leu Phe Val Val Arg His Asn Pro Thr Gly
            355                 360                 365

Thr Val Leu Phe Met Gly Gln Val Met Glu Pro
370                 375

<210> SEQ ID NO 12
<211> LENGTH: 406
<212> TYPE: PRT
<213> ORGANISM: Artificial sequence
<220> FEATURE:
<223> OTHER INFORMATION: VLHL(nt) PAI-1 mutant

<400> SEQUENCE: 12

Met His His His His His Asp Tyr Asp Ile Pro Thr Thr Glu Asn
  1               5                  10                  15

Leu Tyr Phe Gln Gly Ala Met Asp Pro Glu Phe Val His His Pro Pro
            20                  25                  30

Ser Tyr Val Ala His Leu Ala Ser Asp Phe Gly Val Arg Val Phe Gln
            35                  40                  45

Gln Val Ala Gln Ala Ser Lys Asp Arg Asn Val Val Phe Ser Pro Tyr
        50                  55                  60

Gly Val Ala Ser Val Leu Ala Met Leu Gln Leu Thr Thr Gly Gly Glu
65                  70                  75                  80

Thr Gln Gln Gln Ile Gln Ala Ala Met Gly Phe Lys Ile Asp Asp Lys
            85                  90                  95

Gly Met Ala Pro Ala Leu Arg His Leu Tyr Lys Glu Leu Met Gly Pro
            100                 105                 110

Trp Asn Lys Asp Glu Ile Ser Thr Thr Asp Ala Ile Phe Val Gln Arg
            115                 120                 125

Asp Leu Lys Leu Val Gln Gly Phe Met Pro His Phe Phe Arg Leu Phe
        130                 135                 140

Arg Ser Thr Val Lys Gln Val Asp Phe Ser Glu Val Glu Arg Ala Arg
145                 150                 155                 160

Phe Ile Ile Asn Asp Trp Val Lys Thr His Thr Lys Gly Met Ile Ser
            165                 170                 175

Asn Leu Leu Gly Lys Gly Ala Val Asp Gln Leu Thr Arg Leu Val Leu
```

-continued

```
                180                 185                 190
Val Asn Ala Leu Tyr Phe Asn Gly Cys Trp Lys Thr Pro Phe Pro Asp
            195                 200                 205

Ser Ser Thr His Arg Arg Leu Phe His Lys Ser Asp Gly Ser Thr Val
        210                 215                 220

Ser Val Pro Met Met Ala Gln Thr Asn Lys Phe Asn Tyr Thr Glu Phe
225                 230                 235                 240

Thr Thr Pro Asp Gly His Tyr Tyr Asp Ile Leu Glu Leu Pro Tyr His
            245                 250                 255

Gly Asp Thr Leu Ser Met Phe Ile Ala Ala Pro Tyr Glu Lys Glu Val
        260                 265                 270

Pro Leu Ser Ala Leu Thr Asn Ile Leu Ser Ala Gln Leu Ile Ser His
    275                 280                 285

Trp Lys Gly Asn Met Thr Arg Leu Pro Arg Leu Leu Val Leu Pro Lys
        290                 295                 300

Phe Ser Leu Glu Thr Glu Val Asp Leu Arg Lys Pro Leu Glu Asn Leu
305                 310                 315                 320

Gly Met Thr Asp Met Phe Arg Gln Phe Gln Ala Asp Phe Thr Ser Leu
            325                 330                 335

Ser Asp Gln Glu Pro Leu His Val Ala Gln Ala Leu Gln Lys Val Lys
        340                 345                 350

Ile Glu Val Pro Glu Ser Cys Thr Val Ala Ser Ser Thr Ala Val
        355                 360                 365

Ile Val Ser Ala Arg Met Ala Pro Glu Glu Ile Ile Met Asp Arg Pro
    370                 375                 380

Phe Leu Phe Val Val Arg His Asn Pro Thr Gly Thr Val Leu Phe Met
385                 390                 395                 400

Gly Gln Val Met Glu Pro
            405

<210> SEQ ID NO 13
<211> LENGTH: 406
<212> TYPE: PRT
<213> ORGANISM: Artificial sequence
<220> FEATURE:
<223> OTHER INFORMATION: VLHL(nv) PAI-1 mutant

<400> SEQUENCE: 13

Met His His His His His Asp Tyr Asp Ile Pro Thr Thr Glu Asn
1               5                   10                  15

Leu Tyr Phe Gln Gly Ala Met Asp Pro Glu Phe Val His His Pro Pro
            20                  25                  30

Ser Tyr Val Ala His Leu Ala Ser Asp Phe Gly Val Arg Val Phe Gln
        35                  40                  45

Gln Val Ala Gln Ala Ser Lys Asp Arg Asn Val Val Phe Ser Pro Tyr
    50                  55                  60

Gly Val Ala Ser Val Leu Ala Met Leu Gln Leu Thr Thr Gly Gly Glu
65                  70                  75                  80

Thr Gln Gln Gln Ile Gln Ala Ala Met Gly Phe Lys Ile Asp Asp Lys
            85                  90                  95

Gly Met Ala Pro Ala Leu Arg His Leu Tyr Lys Glu Leu Met Gly Pro
        100                 105                 110

Trp Asn Lys Asp Glu Ile Ser Thr Thr Asp Ala Ile Phe Val Gln Arg
    115                 120                 125

Asp Leu Lys Leu Val Gln Gly Phe Met Pro His Phe Phe Arg Leu Phe
130                 135                 140
```

```
Arg Ser Thr Val Lys Lys Val Asp Phe Ser Glu Val Glu Arg Ala Arg
145                 150                 155                 160

Phe Ile Ile Asn Asp Trp Val Lys Thr His Thr Lys Gly Met Ile Ser
                165                 170                 175

Asn Leu Leu Gly Lys Gly Ala Val Asp Gln Leu Thr Arg Leu Val Leu
            180                 185                 190

Val Asn Ala Leu Tyr Phe Asn Gly Cys Trp Lys Thr Pro Phe Pro Asp
        195                 200                 205

Ser Ser Thr His Arg Arg Leu Phe His Lys Ser Asp Gly Ser Thr Val
    210                 215                 220

Ser Val Pro Met Met Ala Gln Thr Asn Lys Phe Asn Tyr Thr Glu Phe
225                 230                 235                 240

Thr Thr Pro Asp Gly His Tyr Tyr Asp Ile Leu Glu Leu Pro Tyr His
                245                 250                 255

Gly Asp Thr Leu Ser Met Phe Ile Ala Ala Pro Tyr Glu Lys Glu Val
            260                 265                 270

Pro Leu Ser Ala Leu Thr Asn Ile Leu Ser Ala Gln Leu Ile Ser His
        275                 280                 285

Trp Lys Gly Asn Met Thr Arg Leu Pro Arg Leu Leu Val Leu Pro Lys
290                 295                 300

Phe Ser Leu Glu Thr Glu Val Asp Leu Arg Lys Pro Leu Glu Asn Leu
305                 310                 315                 320

Gly Met Thr Asp Met Phe Arg Gln Phe Gln Ala Asp Phe Thr Ser Leu
                325                 330                 335

Ser Asp Gln Glu Pro Leu His Val Ala Gln Ala Leu Gln Lys Val Lys
            340                 345                 350

Ile Glu Val Asn Glu Ser Cys Thr Val Ala Ser Ser Thr Ala Val
        355                 360                 365

Ile Val Ser Ala Arg Met Ala Pro Glu Glu Ile Ile Met Asp Arg Pro
    370                 375                 380

Phe Leu Phe Val Val Arg His Asn Pro Thr Gly Thr Val Leu Phe Met
385                 390                 395                 400

Gly Gln Val Met Glu Pro
                405

<210> SEQ ID NO 14
<211> LENGTH: 406
<212> TYPE: PRT
<213> ORGANISM: Artificial sequence
<220> FEATURE:
<223> OTHER INFORMATION: VLHL(ns,nv) PAI-1 mutant

<400> SEQUENCE: 14

Met His His His His His Asp Tyr Asp Ile Pro Thr Thr Glu Asn
1               5                   10                  15

Leu Tyr Phe Gln Gly Ala Met Asp Pro Glu Phe Val His His Pro Pro
                20                  25                  30

Ser Tyr Val Ala His Leu Ala Ser Asp Phe Gly Val Arg Val Phe Gln
            35                  40                  45

Gln Val Ala Gln Ala Ser Lys Asp Arg Asn Val Val Phe Ser Pro Tyr
        50                  55                  60

Gly Val Ala Ser Val Leu Ala Met Leu Gln Leu Thr Thr Gly Gly Glu
65                  70                  75                  80

Thr Gln Gln Gln Ile Gln Ala Ala Met Gly Phe Lys Ile Asp Asp Lys
                85                  90                  95
```

-continued

Gly Met Ala Pro Ala Leu Arg His Leu Tyr Lys Glu Leu Met Gly Pro
            100                 105                 110

Trp Asn Lys Asp Glu Ile Ser Thr Thr Asp Ala Ile Phe Val Gln Arg
        115                 120                 125

Asp Leu Lys Leu Val Gln Gly Phe Met Pro His Phe Arg Leu Phe
    130                 135                 140

Arg Ser Thr Val Lys Lys Val Asp Phe Ser Glu Val Glu Arg Ala Arg
145                 150                 155                 160

Phe Ile Ile Asn Asp Trp Val Lys Thr His Thr Lys Gly Met Ile Ser
                165                 170                 175

Asn Leu Leu Gly Lys Gly Ala Val Asp Gln Leu Thr Arg Leu Val Leu
            180                 185                 190

Val Asn Ala Leu Tyr Phe Asn Gly Cys Trp Lys Thr Pro Phe Pro Asp
        195                 200                 205

Ser Ser Thr His Arg Arg Leu Phe His Lys Ser Asp Gly Ser Thr Val
    210                 215                 220

Ser Val Pro Met Met Ala Gln Thr Asn Lys Phe Asn Tyr Thr Glu Phe
225                 230                 235                 240

Thr Thr Pro Asp Gly His Tyr Tyr Asp Ile Leu Glu Leu Pro Tyr His
                245                 250                 255

Gly Asp Thr Leu Ser Met Phe Ile Ala Ala Pro Tyr Glu Lys Glu Val
            260                 265                 270

Pro Leu Ser Ala Leu Thr Asn Ile Leu Ser Ala Gln Leu Ile Ser His
        275                 280                 285

Trp Lys Gly Asn Met Thr Arg Leu Pro Arg Leu Leu Val Leu Pro Lys
    290                 295                 300

Phe Ser Leu Glu Thr Glu Val Asp Leu Arg Lys Pro Leu Glu Asn Leu
305                 310                 315                 320

Gly Met Thr Asp Met Phe Arg Gln Phe Gln Ala Asp Phe Thr Ser Leu
                325                 330                 335

Ser Asp Gln Glu Pro Leu His Val Ala Gln Ala Leu Gln Lys Val Lys
            340                 345                 350

Ile Glu Val Asn Glu Ser Cys Thr Val Ala Ser Ser Thr Ala Val
        355                 360                 365

Ile Val Ser Ala Ala Met Ala Pro Glu Glu Ile Ile Met Asp Arg Pro
    370                 375                 380

Phe Leu Phe Val Val Arg His Asn Pro Thr Gly Thr Val Leu Phe Met
385                 390                 395                 400

Gly Gln Val Met Glu Pro
                405

<210> SEQ ID NO 15
<211> LENGTH: 406
<212> TYPE: PRT
<213> ORGANISM: Artificial sequence
<220> FEATURE:
<223> OTHER INFORMATION: VLHL(ns, nt) PAI-1 mutant

<400> SEQUENCE: 15

Met His His His His His Asp Tyr Asp Ile Pro Thr Thr Glu Asn
1               5                   10                  15

Leu Tyr Phe Gln Gly Ala Met Asp Pro Glu Phe Val His His Pro Pro
            20                  25                  30

Ser Tyr Val Ala His Leu Ala Ser Asp Phe Gly Val Arg Val Phe Gln
        35                  40                  45

Gln Val Ala Gln Ala Ser Lys Asp Arg Asn Val Val Phe Ser Pro Tyr

```
                50                  55                  60
Gly Val Ala Ser Val Leu Ala Met Leu Gln Leu Thr Thr Gly Gly Glu
 65                  70                  75                  80

Thr Gln Gln Gln Ile Gln Ala Ala Met Gly Phe Lys Ile Asp Asp Lys
                 85                  90                  95

Gly Met Ala Pro Ala Leu Arg His Leu Tyr Lys Glu Leu Met Gly Pro
                100                 105                 110

Trp Asn Lys Asp Glu Ile Ser Thr Thr Asp Ala Ile Phe Val Gln Arg
                115                 120                 125

Asp Leu Lys Leu Val Gln Gly Phe Met Pro His Phe Phe Arg Leu Phe
130                 135                 140

Arg Ser Thr Val Lys Gln Val Asp Phe Ser Glu Val Glu Arg Ala Arg
145                 150                 155                 160

Phe Ile Ile Asn Asp Trp Val Lys Thr His Thr Lys Gly Met Ile Ser
                165                 170                 175

Asn Leu Leu Gly Lys Gly Ala Val Asp Gln Leu Thr Arg Leu Val Leu
                180                 185                 190

Val Asn Ala Leu Tyr Phe Asn Gly Cys Trp Lys Thr Pro Phe Pro Asp
                195                 200                 205

Ser Ser Thr His Arg Arg Leu Phe His Lys Ser Asp Gly Ser Thr Val
210                 215                 220

Ser Val Pro Met Met Ala Gln Thr Asn Lys Phe Asn Tyr Thr Glu Phe
225                 230                 235                 240

Thr Thr Pro Asp Gly His Tyr Tyr Asp Ile Leu Glu Leu Pro Tyr His
                245                 250                 255

Gly Asp Thr Leu Ser Met Phe Ile Ala Ala Pro Tyr Glu Lys Glu Val
                260                 265                 270

Pro Leu Ser Ala Leu Thr Asn Ile Leu Ser Ala Gln Leu Ile Ser His
                275                 280                 285

Trp Lys Gly Asn Met Thr Arg Leu Pro Arg Leu Leu Val Leu Pro Lys
290                 295                 300

Phe Ser Leu Glu Thr Glu Val Asp Leu Arg Lys Pro Leu Glu Asn Leu
305                 310                 315                 320

Gly Met Thr Asp Met Phe Arg Gln Phe Gln Ala Asp Phe Thr Ser Leu
                325                 330                 335

Ser Asp Gln Glu Pro Leu His Val Ala Gln Ala Leu Gln Lys Val Lys
                340                 345                 350

Ile Glu Val Pro Glu Ser Cys Thr Val Ala Ser Ser Ser Thr Ala Val
                355                 360                 365

Ile Val Ser Ala Ala Met Ala Pro Glu Glu Ile Ile Met Asp Arg Pro
370                 375                 380

Phe Leu Phe Val Val Arg His Asn Pro Thr Gly Thr Val Leu Phe Met
385                 390                 395                 400

Gly Gln Val Met Glu Pro
                405

<210> SEQ ID NO 16
<211> LENGTH: 406
<212> TYPE: PRT
<213> ORGANISM: Artificial sequence
<220> FEATURE:
<223> OTHER INFORMATION: VLHL(nv, nt) PAI-1 mutant

<400> SEQUENCE: 16

Met His His His His His Asp Tyr Asp Ile Pro Thr Thr Glu Asn
 1               5                  10                  15
```

```
Leu Tyr Phe Gln Gly Ala Met Asp Pro Glu Phe Val His His Pro Pro
            20                  25                  30

Ser Tyr Val Ala His Leu Ala Ser Asp Phe Gly Val Arg Val Phe Gln
            35                  40                  45

Gln Val Ala Gln Ala Ser Lys Asp Arg Asn Val Val Phe Ser Pro Tyr
 50                  55                  60

Gly Val Ala Ser Val Leu Ala Met Leu Gln Leu Thr Thr Gly Gly Glu
 65                  70                  75                  80

Thr Gln Gln Gln Ile Gln Ala Ala Met Gly Phe Lys Ile Asp Asp Lys
                 85                  90                  95

Gly Met Ala Pro Ala Leu Arg His Leu Tyr Lys Glu Leu Met Gly Pro
            100                 105                 110

Trp Asn Lys Asp Glu Ile Ser Thr Thr Asp Ala Ile Phe Val Gln Arg
            115                 120                 125

Asp Leu Lys Leu Val Gln Gly Phe Met Pro His Phe Phe Arg Leu Phe
130                 135                 140

Arg Ser Thr Val Lys Lys Val Asp Phe Ser Glu Val Glu Arg Ala Arg
145                 150                 155                 160

Phe Ile Ile Asn Asp Trp Val Lys Thr His Thr Lys Gly Met Ile Ser
                165                 170                 175

Asn Leu Leu Gly Lys Gly Ala Val Asp Gln Leu Thr Arg Leu Val Leu
            180                 185                 190

Val Asn Ala Leu Tyr Phe Asn Gly Cys Trp Lys Thr Pro Phe Pro Asp
            195                 200                 205

Ser Ser Thr His Arg Arg Leu Phe His Lys Ser Asp Gly Ser Thr Val
210                 215                 220

Ser Val Pro Met Met Ala Gln Thr Asn Lys Phe Asn Tyr Thr Glu Phe
225                 230                 235                 240

Thr Thr Pro Asp Gly His Tyr Tyr Asp Ile Leu Glu Leu Pro Tyr His
                245                 250                 255

Gly Asp Thr Leu Ser Met Phe Ile Ala Ala Pro Tyr Glu Lys Glu Val
            260                 265                 270

Pro Leu Ser Ala Leu Thr Asn Ile Leu Ser Ala Gln Leu Ile Ser His
            275                 280                 285

Trp Lys Gly Asn Met Thr Arg Leu Pro Arg Leu Leu Val Leu Pro Lys
290                 295                 300

Phe Ser Leu Glu Thr Glu Val Asp Leu Arg Lys Pro Leu Glu Asn Leu
305                 310                 315                 320

Gly Met Thr Asp Met Phe Arg Gln Phe Gln Ala Asp Phe Thr Ser Leu
                325                 330                 335

Ser Asp Gln Glu Pro Leu His Val Ala Gln Ala Leu Gln Lys Val Lys
            340                 345                 350

Ile Glu Val Pro Glu Ser Cys Thr Val Ala Ser Ser Ser Thr Ala Val
            355                 360                 365

Ile Val Ser Ala Arg Met Ala Pro Glu Glu Ile Ile Met Asp Arg Pro
            370                 375                 380

Phe Leu Phe Val Val Arg His Asn Pro Thr Gly Thr Val Leu Phe Met
385                 390                 395                 400

Gly Gln Val Met Glu Pro
                405

<210> SEQ ID NO 17
<211> LENGTH: 406
<212> TYPE: PRT
```

<213> ORGANISM: Artificial sequence
<220> FEATURE:
<223> OTHER INFORMATION: VLHL(ns, nv nt) PAI-1 mutant

<400> SEQUENCE: 17

```
Met His His His His His Asp Tyr Asp Ile Pro Thr Thr Glu Asn
 1               5                  10                  15

Leu Tyr Phe Gln Gly Ala Met Asp Pro Glu Phe Val His His Pro Pro
            20                  25                  30

Ser Tyr Val Ala His Leu Ala Ser Asp Phe Gly Val Arg Val Phe Gln
                35                  40                  45

Gln Val Ala Gln Ala Ser Lys Asp Arg Asn Val Val Phe Ser Pro Tyr
 50                  55                  60

Gly Val Ala Ser Val Leu Ala Met Leu Gln Leu Thr Thr Gly Gly Glu
 65                  70                  75                  80

Thr Gln Gln Gln Ile Gln Ala Ala Met Gly Phe Lys Ile Asp Asp Lys
                85                  90                  95

Gly Met Ala Pro Ala Leu Arg His Leu Tyr Lys Glu Leu Met Gly Pro
            100                 105                 110

Trp Asn Lys Asp Glu Ile Ser Thr Thr Asp Ala Ile Phe Val Gln Arg
            115                 120                 125

Asp Leu Lys Leu Val Gln Gly Phe Met Pro His Phe Phe Arg Leu Phe
130                 135                 140

Arg Ser Thr Val Lys Lys Val Asp Phe Ser Glu Val Glu Arg Ala Arg
145                 150                 155                 160

Phe Ile Ile Asn Asp Trp Val Lys Thr His Thr Lys Gly Met Ile Ser
                165                 170                 175

Asn Leu Leu Gly Lys Gly Ala Val Asp Gln Leu Thr Arg Leu Val Leu
            180                 185                 190

Val Asn Ala Leu Tyr Phe Asn Gly Cys Trp Lys Thr Pro Phe Pro Asp
            195                 200                 205

Ser Ser Thr His Arg Arg Leu Phe His Lys Ser Asp Gly Ser Thr Val
            210                 215                 220

Ser Val Pro Met Met Ala Gln Thr Asn Lys Phe Asn Tyr Thr Glu Phe
225                 230                 235                 240

Thr Thr Pro Asp Gly His Tyr Tyr Asp Ile Leu Glu Leu Pro Tyr His
                245                 250                 255

Gly Asp Thr Leu Ser Met Phe Ile Ala Ala Pro Tyr Glu Lys Glu Val
            260                 265                 270

Pro Leu Ser Ala Leu Thr Asn Ile Leu Ser Ala Gln Leu Ile Ser His
            275                 280                 285

Trp Lys Gly Asn Met Thr Arg Leu Pro Arg Leu Leu Val Leu Pro Lys
            290                 295                 300

Phe Ser Leu Glu Thr Glu Val Asp Leu Arg Lys Pro Leu Glu Asn Leu
305                 310                 315                 320

Gly Met Thr Asp Met Phe Arg Gln Phe Gln Ala Asp Phe Thr Ser Leu
                325                 330                 335

Ser Asp Gln Glu Pro Leu His Val Ala Gln Ala Leu Gln Lys Val Lys
            340                 345                 350

Ile Glu Val Pro Glu Ser Cys Thr Val Ala Ser Ser Thr Ala Val
            355                 360                 365

Ile Val Ser Ala Ala Met Ala Pro Glu Glu Ile Ile Met Asp Arg Pro
            370                 375                 380

Phe Leu Phe Val Val Arg His Asn Pro Thr Gly Thr Val Leu Phe Met
385                 390                 395                 400
```

```
Gly Gln Val Met Glu Pro
                405

<210> SEQ ID NO 18
<211> LENGTH: 351
<212> TYPE: PRT
<213> ORGANISM: Artificial Sequence
<220> FEATURE:
<223> OTHER INFORMATION: mini-VLHL(ns)

<400> SEQUENCE: 18

Met His His His His His Asp Tyr Asp Ile Pro Thr Thr Glu Asn
 1               5                  10                  15

Leu Tyr Phe Gln Gly Ala Met Asp Pro Glu Phe Val His His Pro Pro
                20                  25                  30

Ser Tyr Val Ala His Leu Ala Ser Asp Phe Gly Val Arg Val Phe Gln
                35                  40                  45

Gln Val Ala Gln Ala Ser Lys Asp Arg Asn Val Val Phe Ser Pro Tyr
            50                  55                  60

Gly Val Ala Ser Val Leu Ala Met Leu Gln Leu Thr Thr Gly Gly Glu
65                  70                  75                  80

Thr Gln Gln Gln Ile Gln Ala Ala Met Gly Phe Lys Ile Asp Asp Lys
                85                  90                  95

Gly Met Ala Pro Ala Leu Arg His Leu Tyr Lys Glu Leu Met Gly Pro
                100                 105                 110

Trp Asn Lys Asp Glu Ile Ser Thr Thr Asp Ala Ile Phe Val Gln Arg
            115                 120                 125

Asp Leu Gln Leu Thr Arg Leu Val Leu Val Asn Ala Leu Tyr Phe Asn
            130                 135                 140

Gly Cys Trp Lys Thr Pro Phe Pro Asp Ser Ser Thr His Arg Arg Leu
145                 150                 155                 160

Phe His Lys Ser Asp Gly Ser Thr Val Ser Val Pro Met Met Ala Gln
                165                 170                 175

Thr Asn Lys Phe Asn Tyr Thr Glu Phe Thr Thr Pro Asp Gly His Tyr
                180                 185                 190

Tyr Asp Ile Leu Glu Leu Pro Tyr His Gly Asp Thr Leu Ser Met Phe
            195                 200                 205

Ile Ala Ala Pro Tyr Glu Lys Glu Val Pro Leu Ser Ala Leu Thr Asn
        210                 215                 220

Ile Leu Ser Ala Gln Leu Ile Ser His Trp Lys Gly Asn Met Thr Arg
225                 230                 235                 240

Leu Pro Arg Leu Leu Val Leu Pro Lys Phe Ser Leu Glu Thr Glu Val
                245                 250                 255

Asp Leu Arg Lys Pro Leu Glu Asn Leu Gly Met Thr Asp Met Phe Arg
            260                 265                 270

Gln Phe Gln Ala Asp Phe Thr Ser Leu Ser Asp Gln Glu Pro Leu His
            275                 280                 285

Val Ala Gln Ala Leu Gln Lys Val Lys Ile Glu Val Asn Glu Ser Cys
        290                 295                 300

Thr Val Ala Ser Ser Ser Thr Ala Val Ile Val Ser Ala Ala Met Ala
305                 310                 315                 320

Pro Glu Glu Ile Ile Met Asp Arg Pro Phe Leu Phe Val Val Arg His
                325                 330                 335

Asn Pro Thr Gly Thr Val Leu Phe Met Gly Gln Val Met Glu Pro
                340                 345                 350
```

<210> SEQ ID NO 19
<211> LENGTH: 351
<212> TYPE: PRT
<213> ORGANISM: Artificial Sequence
<220> FEATURE:
<223> OTHER INFORMATION: mini-VLHL(nt)

<400> SEQUENCE: 19

```
Met His His His His His Asp Tyr Asp Ile Pro Thr Thr Glu Asn
 1               5                  10                  15

Leu Tyr Phe Gln Gly Ala Met Asp Pro Glu Phe Val His His Pro Pro
             20                  25                  30

Ser Tyr Val Ala His Leu Ala Ser Asp Phe Gly Val Arg Val Phe Gln
             35                  40                  45

Gln Val Ala Gln Ala Ser Lys Asp Arg Asn Val Val Phe Ser Pro Tyr
     50                  55                  60

Gly Val Ala Ser Val Leu Ala Met Leu Gln Leu Thr Thr Gly Gly Glu
 65                  70                  75                  80

Thr Gln Gln Gln Ile Gln Ala Ala Met Gly Phe Lys Ile Asp Asp Lys
                 85                  90                  95

Gly Met Ala Pro Ala Leu Arg His Leu Tyr Lys Glu Leu Met Gly Pro
            100                 105                 110

Trp Asn Lys Asp Glu Ile Ser Thr Thr Asp Ala Ile Phe Val Gln Arg
            115                 120                 125

Asp Leu Gln Leu Thr Arg Leu Val Leu Val Asn Ala Leu Tyr Phe Asn
        130                 135                 140

Gly Cys Trp Lys Thr Pro Phe Pro Asp Ser Ser Thr His Arg Arg Leu
145                 150                 155                 160

Phe His Lys Ser Asp Gly Ser Thr Val Ser Val Pro Met Met Ala Gln
                165                 170                 175

Thr Asn Lys Phe Asn Tyr Thr Glu Phe Thr Thr Pro Asp Gly His Tyr
            180                 185                 190

Tyr Asp Ile Leu Glu Leu Pro Tyr His Gly Asp Thr Leu Ser Met Phe
        195                 200                 205

Ile Ala Ala Pro Tyr Glu Lys Glu Val Pro Leu Ser Ala Leu Thr Asn
    210                 215                 220

Ile Leu Ser Ala Gln Leu Ile Ser His Trp Lys Gly Asn Met Thr Arg
225                 230                 235                 240

Leu Pro Arg Leu Leu Val Leu Pro Lys Phe Ser Leu Glu Thr Glu Val
                245                 250                 255

Asp Leu Arg Lys Pro Leu Glu Asn Leu Gly Met Thr Asp Met Phe Arg
            260                 265                 270

Gln Phe Gln Ala Asp Phe Thr Ser Leu Ser Asp Gln Glu Pro Leu His
        275                 280                 285

Val Ala Gln Ala Leu Gln Lys Val Lys Ile Glu Val Pro Glu Ser Cys
    290                 295                 300

Thr Val Ala Ser Ser Ser Thr Ala Val Ile Val Ser Ala Arg Met Ala
305                 310                 315                 320

Pro Glu Glu Ile Ile Met Asp Arg Pro Phe Leu Phe Val Val Arg His
                325                 330                 335

Asn Pro Thr Gly Thr Val Leu Phe Met Gly Gln Val Met Glu Pro
            340                 345                 350
```

<210> SEQ ID NO 20
<211> LENGTH: 351
<212> TYPE: PRT

<213> ORGANISM: Artificial Sequence
<220> FEATURE:
<223> OTHER INFORMATION: mini-VLHL(nt, ns)

<400> SEQUENCE: 20

```
Met His His His His His Asp Tyr Asp Ile Pro Thr Thr Glu Asn
 1               5                  10                  15

Leu Tyr Phe Gln Gly Ala Met Asp Pro Glu Phe Val His His Pro Pro
            20                  25                  30

Ser Tyr Val Ala His Leu Ala Ser Asp Phe Gly Val Arg Val Phe Gln
            35                  40                  45

Gln Val Ala Gln Ala Ser Lys Asp Arg Asn Val Val Phe Ser Pro Tyr
 50                  55                  60

Gly Val Ala Ser Val Leu Ala Met Leu Gln Leu Thr Thr Gly Gly Glu
 65                  70                  75                  80

Thr Gln Gln Gln Ile Gln Ala Ala Met Gly Phe Lys Ile Asp Asp Lys
                85                  90                  95

Gly Met Ala Pro Ala Leu Arg His Leu Tyr Lys Glu Leu Met Gly Pro
                100                 105                 110

Trp Asn Lys Asp Glu Ile Ser Thr Thr Asp Ala Ile Phe Val Gln Arg
            115                 120                 125

Asp Leu Gln Leu Thr Arg Leu Val Leu Val Asn Ala Leu Tyr Phe Asn
130                 135                 140

Gly Cys Trp Lys Thr Pro Phe Pro Asp Ser Ser Thr His Arg Arg Leu
145                 150                 155                 160

Phe His Lys Ser Asp Gly Ser Thr Val Ser Val Pro Met Met Ala Gln
                165                 170                 175

Thr Asn Lys Phe Asn Tyr Thr Glu Phe Thr Thr Pro Asp Gly His Tyr
            180                 185                 190

Tyr Asp Ile Leu Glu Leu Pro Tyr His Gly Asp Thr Leu Ser Met Phe
            195                 200                 205

Ile Ala Ala Pro Tyr Glu Lys Glu Val Pro Leu Ser Ala Leu Thr Asn
210                 215                 220

Ile Leu Ser Ala Gln Leu Ile Ser His Trp Lys Gly Asn Met Thr Arg
225                 230                 235                 240

Leu Pro Arg Leu Leu Val Leu Pro Lys Phe Ser Leu Glu Thr Glu Val
                245                 250                 255

Asp Leu Arg Lys Pro Leu Glu Asn Leu Gly Met Thr Asp Met Phe Arg
            260                 265                 270

Gln Phe Gln Ala Asp Phe Thr Ser Leu Ser Asp Gln Glu Pro Leu His
            275                 280                 285

Val Ala Gln Ala Leu Gln Lys Val Lys Ile Glu Val Pro Glu Ser Cys
290                 295                 300

Thr Val Ala Ser Ser Ser Thr Ala Val Ile Val Ser Ala Ala Met Ala
305                 310                 315                 320

Pro Glu Glu Ile Ile Met Asp Arg Pro Phe Leu Phe Val Val Arg His
                325                 330                 335

Asn Pro Thr Gly Thr Val Leu Phe Met Gly Gln Val Met Glu Pro
            340                 345                 350
```

<210> SEQ ID NO 21
<211> LENGTH: 10
<212> TYPE: PRT
<213> ORGANISM: Artificial sequence
<220> FEATURE:
<223> OTHER INFORMATION: uPA peptide which binds to PAI-1

```
<400> SEQUENCE: 21

Thr Pro Phe Pro Asp Ser Ser Thr His Arg
 1               5                  10

<210> SEQ ID NO 22
<211> LENGTH: 8
<212> TYPE: PRT
<213> ORGANISM: Artificial sequence
<220> FEATURE:
<223> OTHER INFORMATION: uPA peptide which binds to PAI-1

<400> SEQUENCE: 22

Gly Ala Val Asp Gln Leu Thr Arg
 1               5

<210> SEQ ID NO 23
<211> LENGTH: 10
<212> TYPE: PRT
<213> ORGANISM: Artificial sequence
<220> FEATURE:
<223> OTHER INFORMATION: uPA peptide which binds to PAI-1

<400> SEQUENCE: 23

Val Gly Gln Gln Val Ala Gln Ala Ser Lys
 1               5                  10

<210> SEQ ID NO 24
<211> LENGTH: 16
<212> TYPE: PRT
<213> ORGANISM: Artificial sequence
<220> FEATURE:
<223> OTHER INFORMATION: uPA peptide which binds to PAI-1
<220> FEATURE:
<221> NAME/KEY: mutation
<222> LOCATION: 10, 11
<223> OTHER INFORMATION: Xaa = oxidized methionine

<400> SEQUENCE: 24

Ser Asp Gly Ser Thr Val Ser Val Pro Xaa Xaa Ala Gln Thr Asn Lys
 1               5                  10                  15

<210> SEQ ID NO 25
<211> LENGTH: 9
<212> TYPE: PRT
<213> ORGANISM: Artificial sequence
<220> FEATURE:
<223> OTHER INFORMATION: uPA peptide which binds to PAI-1

<400> SEQUENCE: 25

Gln Val Asp Phe Ser Glu Val Glu Arg
 1               5

<210> SEQ ID NO 26
<211> LENGTH: 13
<212> TYPE: PRT
<213> ORGANISM: Artificial sequence
<220> FEATURE:
<223> OTHER INFORMATION: uPA peptide which binds to PAI-1
<220> FEATURE:
<221> NAME/KEY: VARIANT
<222> LOCATION: 8, 11
<223> OTHER INFORMATION: Xaa = oxidized methionine

<400> SEQUENCE: 26

Lys Pro Leu Glu Asn Leu Gly Xaa Thr Asp Xaa Phe Arg
 1               5                  10

<210> SEQ ID NO 27
```

```
<211> LENGTH: 9
<212> TYPE: PRT
<213> ORGANISM: Artificial sequence
<220> FEATURE:
<223> OTHER INFORMATION: uPA peptide which binds to PAI-1
<220> FEATURE:
<221> NAME/KEY: VARIANT
<222> LOCATION: 2
<223> OTHER INFORMATION: Xaa = oxidized methionine

<400> SEQUENCE: 27

Gly Xaa Ile Ser Asn Leu Leu Gly Lys
 1               5

<210> SEQ ID NO 28
<211> LENGTH: 13
<212> TYPE: PRT
<213> ORGANISM: Artificial sequence
<220> FEATURE:
<223> OTHER INFORMATION: uPA peptide which binds to PAI-1

<400> SEQUENCE: 28

Asp Glu Ile Ser Thr Thr Asp Ala Ile Phe Val Gln Arg
 1               5                  10

<210> SEQ ID NO 29
<211> LENGTH: 10
<212> TYPE: PRT
<213> ORGANISM: Artificial sequence
<220> FEATURE:
<223> OTHER INFORMATION: uPA peptide which binds to PAI-1

<400> SEQUENCE: 29

Phe Ser Leu Glu Thr Glu Val Asp Leu Arg
 1               5                  10

<210> SEQ ID NO 30
<211> LENGTH: 8
<212> TYPE: PRT
<213> ORGANISM: Artificial sequence
<220> FEATURE:
<223> OTHER INFORMATION: uPA peptide which binds to PAI-1

<400> SEQUENCE: 30

Phe Ile Ile Asn Asp Trp Val Lys
 1               5

<210> SEQ ID NO 31
<211> LENGTH: 5
<212> TYPE: PRT
<213> ORGANISM: Artificial sequence
<220> FEATURE:
<223> OTHER INFORMATION: uPA peptide which binds to PAI-1
<220> FEATURE:
<221> NAME/KEY: VARIANT
<222> LOCATION: 1
<223> OTHER INFORMATION: Xaa = oxidized methionine

<400> SEQUENCE: 31

Xaa Thr Val Val Lys
 1               5

<210> SEQ ID NO 32
<211> LENGTH: 8
<212> TYPE: PRT
<213> ORGANISM: Artificial sequence
<220> FEATURE:
<223> OTHER INFORMATION: uPA peptide which binds to PAI-1

<400> SEQUENCE: 32
```

```
Asp Lys Pro Gly Val Tyr Thr Arg
1               5
```

<210> SEQ ID NO 33
<211> LENGTH: 10
<212> TYPE: PRT
<213> ORGANISM: Artificial sequence
<220> FEATURE:
<223> OTHER INFORMATION: uPA peptide which binds to PAI-1

<400> SEQUENCE: 33

```
Lys Pro Ser Ser Pro Glu Glu Leu Lys
1               5                   10
```

<210> SEQ ID NO 34
<211> LENGTH: 11
<212> TYPE: PRT
<213> ORGANISM: Artificial sequence
<220> FEATURE:
<223> OTHER INFORMATION: uPA peptide which binds to PAI-1

<400> SEQUENCE: 34

```
Ser His Thr Lys Glu Glu Asn Gly Leu Ala Leu
1               5                   10
```

<210> SEQ ID NO 35
<211> LENGTH: 10
<212> TYPE: PRT
<213> ORGANISM: Artificial sequence
<220> FEATURE:
<223> OTHER INFORMATION: uPA peptide which binds to PAI-1

<400> SEQUENCE: 35

```
Ser Asp Ala Leu Gln Leu Gly Leu Gly Lys
1               5                   10
```

<210> SEQ ID NO 36
<211> LENGTH: 10
<212> TYPE: PRT
<213> ORGANISM: Artificial sequence
<220> FEATURE:
<223> OTHER INFORMATION: uPA peptide which binds to PAI-1

<400> SEQUENCE: 36

```
Phe Glu Val Glu Asn Leu Ile Leu His Lys
1               5                   10
```

<210> SEQ ID NO 37
<211> LENGTH: 9
<212> TYPE: PRT
<213> ORGANISM: Artificial sequence
<220> FEATURE:
<223> OTHER INFORMATION: uPA peptide which binds to PAI-1
<220> FEATURE:
<221> NAME/KEY: VARIANT
<222> LOCATION: 1
<223> OTHER INFORMATION: Xaa = non-tryptic Tyrosine

<400> SEQUENCE: 37

```
Xaa Tyr Gly Ser Glu Val Thr Thr Lys
1               5
```

<210> SEQ ID NO 38
<211> LENGTH: 10
<212> TYPE: PRT
<213> ORGANISM: Artificial Sequence
<220> FEATURE:
<223> OTHER INFORMATION: artificial purification tag

```
<400> SEQUENCE: 38

Met Ser Ser Tyr His His His His His His
1               5                   10
```